(12) United States Patent
Valenta et al.

(10) Patent No.: US 9,638,694 B2
(45) Date of Patent: May 2, 2017

(54) METHOD FOR DIAGNOSING A RHINOVIRUS INFECTION

(75) Inventors: Rudolf Valenta, Theresienfeld (AT); Katarzyna Niespodziana, Vienna (AT); Johanna Edlmayr, Munich (DE); Dieter Blaas, Vienna (AT); Verena Niederberger-Leppin, Vienna (AT); Nikos Papadopoulos, Greece (GR); Theresia Popow-Kraupp, Vienna (AT)

(73) Assignee: Viravaxx GmbH, Vienna (AT)

( * ) Notice: Subject to any disclaimer, the term of this patent is extended or adjusted under 35 U.S.C. 154(b) by 411 days.

(21) Appl. No.: 13/504,766

(22) PCT Filed: Nov. 2, 2010

(86) PCT No.: PCT/AT2010/000416
§ 371 (c)(1),
(2), (4) Date: Apr. 27, 2012

(87) PCT Pub. No.: WO2011/050384
PCT Pub. Date: May 5, 2011

(65) Prior Publication Data
US 2012/0213820 A1  Aug. 23, 2012

(30) Foreign Application Priority Data
Oct. 30, 2009  (EP) .................................... 09174613

(51) Int. Cl.
*C12Q 1/02* (2006.01)
*C12Q 1/04* (2006.01)
*C12Q 1/70* (2006.01)
*A61K 39/12* (2006.01)
*G01N 33/569* (2006.01)

(52) U.S. Cl.
CPC ....... *G01N 33/56983* (2013.01); *A61K 39/12* (2013.01); *C12Q 1/02* (2013.01); *C12Q 1/04* (2013.01); *C12Q 1/70* (2013.01); *C12N 2770/32734* (2013.01); *G01N 2333/095* (2013.01); *G01N 2469/20* (2013.01)

(58) Field of Classification Search
CPC .............. C07K 14/005; C07K 16/1009; C07K 2319/40; C07K 2319/735; C07K 2317/21; C07K 2317/33; C12N 2770/32722; C12N 2770/32734; C12N 7/00; C12N 2770/32011; C12N 2770/32711; A61K 39/00; A61K 38/00; A61K 39/125; A61K 2039/525; G06F 19/22; G01N 2333/095; G01N 2469/20; G01N 33/56983; C12Q 1/00
See application file for complete search history.

(56) References Cited

FOREIGN PATENT DOCUMENTS

| WO | WO 97/22701 A1 | 6/1997 |
|---|---|---|
| WO | WO 02/055697 A2 | 7/2002 |
| WO | WO 2006/078648 A2 | 7/2006 |
| WO | WO 2007/140505 A2 | 12/2007 |
| WO | WO 2008/016594 A1 | 2/2008 |
| WO | WO 2008/057158 A2 | 5/2008 |
| WO | WO 2008/104953 A2 | 9/2008 |

OTHER PUBLICATIONS

GenBank submission ADP00763.1 (Oct. 4, 2010).*
Katpally et al., Journal of Virology, 2009, 83(14):7040-7048.*
Prchla et al., Virus-mediated Release of Endosomal Content in Vitro: Different Behavior of Adenovirus and Rhinovirus Serotype 2, The Journal of Cell Biology, 131: 111-123 (1995).
Wang et al., Capsid structure and dynamics of a human rhinovirus probed by hydrogen exchange mass spectrometry, Protein Science, 14: 1661-1672 (2005).
Ledford et al., VP1 sequencing of all human rhinovirus serotypes: Insights into genus phylogeny and susceptibility to antiviral capsid-binding compounds, Journal of Virology, 78: 3663-3674 (2004).
Edlmayr et al., Antibodies induced with recombinant VP1 from human rhinovirus exhibit cross-neutralisation, European Respiratory Journal, 37: 44-52 (Jun. 2010).
Hastings et al., Neutralizing Antibodies to Human Rhinovirus Produced in Laboratory Animals and Humans that Recognize a Linear Sequence from VP2, Journal of General Virology, 71: 3055-3059 (1990).
Edlmayr et al., A Combination Vaccine for Allergy and Rhinovirus Infections Based on Rhinovirus-Derived Surface Protein VP1 and a Nonallergenic Peptide of the Major Timothy Grass Pollen Allargen Ph1 p. 1, Journal of Immunology, 182: 6298-6306 (2009).
Bardin, P.G., Vaccination for asthma exacerbations, Internal Medicine Journal, 34: 358-360 (2004).
Francis et al., Immunological properties of hepatitis B core antigen fusion proteins, Proceedings of the National Academy of Sciences USA, 87: 2545-2549 (1990).
Johnson et al., Molecular Adjuvants and Immunomodulators: New Approaches to Immunization, Clinical Microbiology Reviews, 7: 277-289 (1994).
McCray et al., Different rhinovirus serotypes neutralized by antipeptide antibodies, Nature, 329: 736-738 (1987).
Prchla et al., Virus-mediated Release of Endosomal Content in Vitro: Dependence on the Activity of the Vacuolar Proton ATPase (V-ATPase), Molecular Biology of the Cell, 5: 192a (1994).
Stott et al., Some Improved Techniques for the Study of Rhinovirus Using HeLa Cells, Archives of Virology, 23: 236-244 (1968).
Gupta et al., Adjuvants—a balance between toxicity and adjuvanticity, Vaccine, 11: 293-306 (1993).
Brown et al., Foreign epitopes in immunodominant regions of hepatitis B core particles are highly immunogenic and conformationally restricted, Vaccine, 9: 595-601 (1991).
European Search Report for Appl. No. 09174613.1, Oct. 13, 2010, European Patent Office.

* cited by examiner

*Primary Examiner* — Nicole Kinsey White
(74) *Attorney, Agent, or Firm* — Nevrivy Patent Law Group P.L.L.C.

(57) ABSTRACT

The present invention relates to a pharmaceutical composition comprising at least one peptide consisting of a minimum of 8 and a maximum of 50 amino acid residues comprising amino acid residues 1 to 8 of a rhinovirus capsid protein selected from the group consisting of VP1, VP2, VP3 and VP4.

5 Claims, 19 Drawing Sheets

Fig. 3
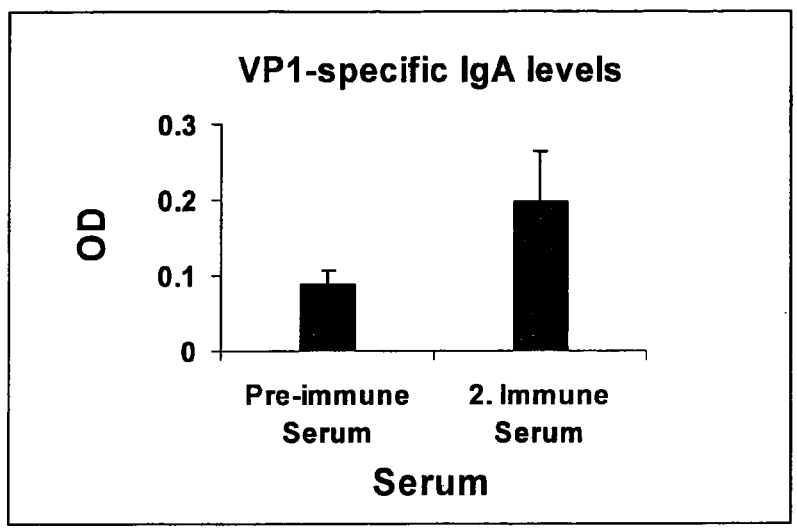
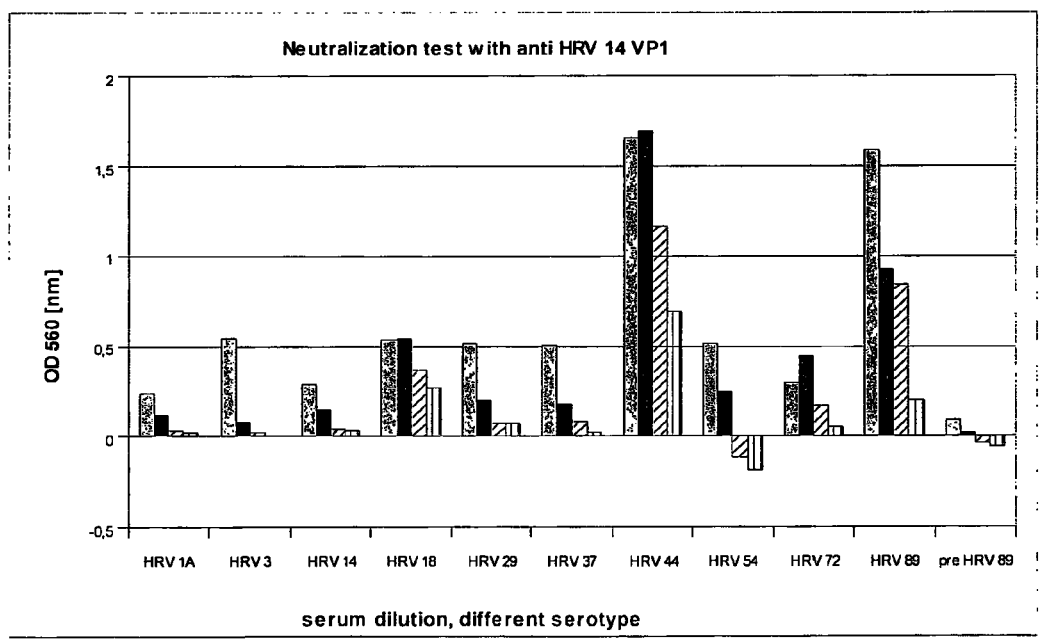
Fig. 4

Fig. 5
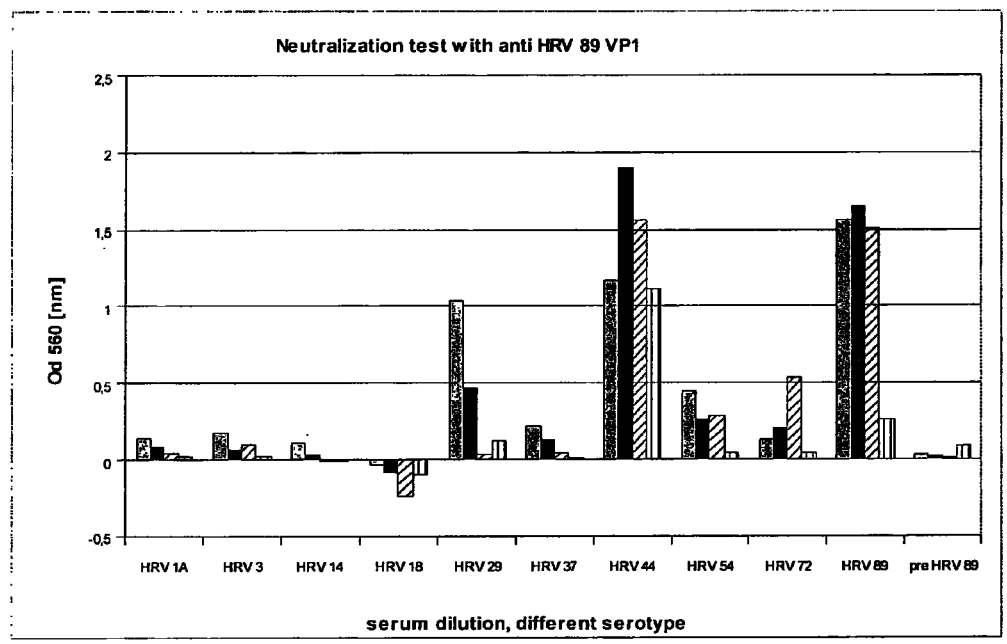
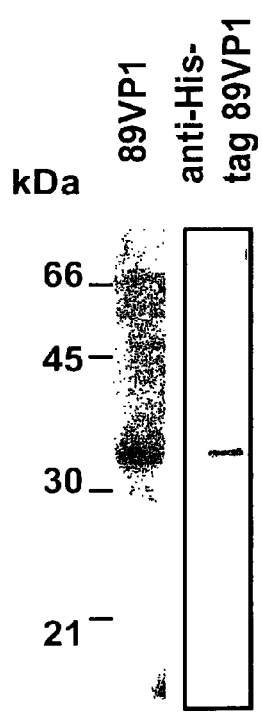
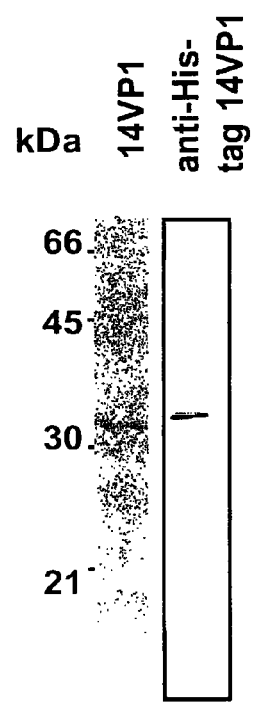
Fig. 6

EPITOPE_1

```
HRV_89  NPVENYIDSVLNEVLVVPNIQPSTSVSSHAAPALDAAETGHTSSVQPEDMIETRYVITDQFRDETSIESFLGRSGCIAMIEFNTSSD-KTEHDKIGKGPK    99
HRV_37  GLGDELEEV..EKTKQTLASIS.GPKH.QSV.T.T.N...A.MPTN.S.N....TTYMHFNGS..D........AA..H.T.IENKNSTG.VNH.SD.L.N   100
HRV_18  ........E..........NE.HA...NS............N.........Q.S.....M...C........H.SKLVVHYE-DYNAETR--N.V        97
HRV_54  ....R...E..........RE.HPA..NS............G.....T....Q.S.....M.........A...HESTITIQN--DV.Y.DH--H..      97
HRV_1A  ........E..........KE.HHT..NS..L..........N.....A.......S.....M...........H.SRIKVDYT-DYNGQD.--N.T       97
HRV_29  ........E..........RE.HPS..NS..I..........N.....T.....Q.SH....M...........H.STIKAN-----.AHDA--K.D       93
HRV_44  ........E..........RE.HPSI.NS..I..........N.....T.....Q.S.....M...........H.STIK.N-----.AHNT--K.D       93
HRV_3   GLSDELEEV..EKTKQTLASVS.GPKH.QSV....T.N...A.LPTR.S.N....TTYMHFNGS..D........AA..H.T.IKNKNAAGLDNH.KEGL.N  100
HRV_14  GLGDELEEV..EKTKQTVASIS.GPKH.QKV.I.T.N...A.MP.L.S.S....TTYMHFNGS..D..C.....AA..H.T.IQNKDATGIDNH.EA.L.N   100
HRV_72  GLNDELEEV..EKTKQTLASIS.GPKY.QSV.T.T.N...A.MPTL.S.N....TTYMHFNGS..D..C.....AA..H.T.IENKNPNGISNH.AE.L.N   100
```

EPITOPE_2

```
HRV_89  TWKVSLQEMAQIRRKYELFTYTRFDSEITIVTAAAA--QGNDSGHIVLQFMYVPPGAPVPEKRDDYTWQSGTNASVFWQEGQPYPRFTIPFMSIASAYYMFY   199
HRV_37  D...N.SS.V.....L.....V.....Y.....AT.SQPSKS.YASN...A.........N.KEW........A..P....KV.DTA-.......G....NC..  201
HRV_18  K.Q.N..............V........PSV..--K...I............KT...A..........H..T.........................     197
HRV_54  K.D............F...V........PCI.G--K.V.I............K...........S..P.....H..A.....................   196
HRV_1A  K..................V........PCI.G--R...I............S.......M.....H..............................    197
HRV_29  K.N.N..............V........PCI.G--R...I.............ND..H.A........H.............................    193
HRV_44  K.N.N..............V........PCI.G--R...I.............DD.IH.A....N....H.............................   193
HRV_3   D...N.SS.V.....L.....V.....Y.....AT.SQPEASSY.SN.T..A.........N.KEW........A..P....KV.TS-........G....NC..  201
HRV_14  D...N.SS.V.....L.....V.....Y.....AT.SQPDSA.Y.SN....A.........N.KEW........A..P....KV.DTS-.......G....NC..  201
HRV_72  D.....SS.V.....L.....V.....Y.....AT.SQPDTA.Y.SN....A.........N.VEW........A..P....KV.DTS-.......G....NC..  201
```

EPITOPE_3

```
HRV_89  DGYDGDSAASKYGSVVTNDMGTICVRIVTSNQKHDLNIVCRIYHKAKHIKANCPRPPRAVAYQNTHSTNYIPSNGEATTQIKTRP-DVFTVTNV   292   SEQ ID NO:27
HRV_37  ...SH.DEN.P...IT.L.H....AF...NEHDA.TTL.KI.........E...I..A....P..AIGK...-..RM--I.PV..K.D-..T.Y---       288   SEQ ID NO:21
HRV_18  ......QTS.....A........S....DKH.NE.E.TT..............E.T...V...K.KE.REK.A.VP.A-R.TMA---                 287   SEQ ID NO:16
HRV_54  ......APG.....S....H....S....DK...P.E.TT.............A....P.T..R.....RE.DP.IF..H.T-...V.A---           286   SEQ ID NO:23
HRV_1A  ......NPS...............S....EK...S.V.TTH........T..........P.T...V....ET.DV..A.VR.N-T.T.A---          287   SEQ ID NO:8
HRV_29  .....GDHTAT....T.V.R........GK.A....Q.TTS.............V.P.KYVGL....TLKE--ED.V.E....-S.M.A---           281   SEQ ID NO:19
HRV_44  .....GDHTAT....T.V.R........GK.A....Q.TTS.............V.P.KYVGL....TLKE--TD.V.EP.H-S.M.A---            281   SEQ ID NO:22
HRV_3   ...SH.DPD.P...IT.L.H....AF...NEHDV.TTL.KI.........E...I..A....P.VSIGR...-..R.--SK.I..K.T-..K.Y---       288   SEQ ID NO:11
HRV_14  ...SH.D.E.Q...IT.L.H....AF...NEHDE.KTL.KI.........E...I..A....P..TEPV..K.KG..K.Y---                     289   SEQ ID NO:13
HRV_72  ...SH.D.E.Q...IS.L.H....AF...NEHDT.RTL.KI.........E...V..A....P.TSIGR...-..K.--PKPV..K.EG..K.Y---       289   SEQ ID NO:24
```

■ Major group genus A

■ K-type (major group) genus A

■ Major group genus B

■ Minor group genus A

METHOD FOR DIAGNOSING A RHINOVIRUS INFECTION

REFERENCE TO A SEQUENCE LISTING SUBMITTED ELECTRONICALLY VIA EFS-WEB

The content of the sequence listing (Name: Seq_listing_ST25.txt, Size: 78,195 bytes; and Date of Creation: Apr. 27, 2012) electronically submitted via EFS-Web is incorporated by reference in its entirety.

The present invention relates to a pharmaceutical composition for the treatment and prevention of a rhinovirus infection.

Rhinoviruses are nonenveloped viruses containing a single-strand RNA genome within an icosahedral capsid. Rhinoviruses belong to the family of Picornaviridae, which includes the genera *Enterovirus* (polioviruses, coxsackieviruses groups A and B, echoviruses, numbered enteroviruses, parechoviruses) and *Hepatovirus* (hepatitis A virus). More than 110 serotypes have been identified.

Rhinoviruses are usually transmitted by aerosol or direct contact. The primary site of inoculation is the nasal mucosa, although the conjunctiva may be involved to a lesser extent. Rhinovirus attaches to respiratory epithelium and locally spreads, wherein the major human rhinovirus receptor is inter-cellular adhesion molecule-1 (ICAM-1). The natural response of the human defense system to injury involves ICAM-1, which supports the binding between endothelial cells and leukocytes. Rhinovirus takes advantage of the ICAM-1 by using it as a receptor for attachment.

A local inflammatory response to the virus in the respiratory tract may lead to nasal discharge, nasal congestion, sneezing, and throat irritation. Damage to the nasal epithelium does not occur, and inflammation is mediated by the production of cytokines and other mediators.

Histamine concentrations in nasal secretions do not increase. By days 3-5 of the illness, nasal discharge may become mucopurulent from polymorphonuclear leukocytes that have migrated to the infection site in response to chemoattractants, such as interleukin-8. Nasal mucociliary transport is markedly reduced during the illness and may be impaired for weeks. Both secretory immunoglobulin A and serum antibodies are involved in resolving the illness and protecting from reinfection.

Common colds caused by rhinovirus infection are most frequent from September to April in temperate climates. Rhinovirus infections, which are present throughout the year, account for the initial increase in cold incidence during the fall and for a second incidence peak at the end of the spring season. Several studies demonstrate the incidence of the common cold to be highest in preschool- and elementary school-aged children. An average of 3-8 colds per year is observed in this age group, with an even higher incidence in children who attend daycare and preschool. Because of the numerous viral agents involved and the many serotypes of rhinoviruses, younger children having new colds each month during the winter season is not unusual. Adults and adolescents typically have 2-4 colds per year.

The most common manifestation of rhinovirus, the common cold, is mild and self-limited. However, severe respiratory disease, including bronchiolitis and pneumonia, may occur rarely.

Since early attempts to prevent rhinovirus infections by vaccination have not been successful (Mc Cray et al. Nature 329: 736-738 (1987); Brown et al. Vaccine 9: 595-601 (1991); Francis et al. PNAS USA 87: 2545-2549 (1990)), the current rhinovirus treatment is limited to a symptomatic treatment with analgesics, decongestants, antihistamines and antitussives. Due to the diversity of rhinovirus serotypes and the lack of cross-protection during reinfection with heterologous serotypes a successful prevention by vaccination is considered impossible (Bardin P G, Intern. Med. J. 34 (2004): 358-360). Therefore, the development of respective pharmaceutical compounds is mainly focused on the development of antiviral molecules, such as interferons and synthetic anti-rhinovirus compounds, which could be used therapeutically as well as prophylactically.

WO 2008/057158 relates to vaccines comprising rhinovirus neutralizing immunogen peptides derived from the C-terminal region of the capsid protein VP1 of human rhinovirus. However, some of the peptides disclosed therein are able to induce the formation of antibodies directed to a broad member of rhinovirus serotypes.

In the EP 0 358 485 T cell epitope containing peptides of the VP2 capsid protein of rhinovirus serotype 2 having less than 40 amino acid residues are disclosed.

It is an object of the present invention to provide for the first time a pharmaceutical formulation to be used as vaccine for the treatment or prevention of rhinovirus infections.

The present invention relates to a pharmaceutical composition comprising at least one peptide consisting of a minimum of 8 and a maximum of 50 amino acid residues comprising amino acid residues 1 to 8 of a rhinovirus capsid protein selected from the group consisting of VP1, VP2, VP3 and VP4.

It turned out that peptides derived from rhinovirus capsid proteins VP1, VP2, VP3 and VP4 which comprise the first 8 N-terminal amino acid residues of said capsid proteins are able to induce the in vivo formation of antibodies directed to rhinovirus particles. The at least one peptide may comprise in total 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 amino acid residues. Thus, the at least one peptide comprises amino acid residues 1 to 8, preferably 1 to 9, 1 to 10, 1 to 11, 1 to 12, 1 to 13, 1 to 14, 1 to 15, 1 to 16, 1 to 17, 1 to 18, 1 to 19, 1 to 20, 1 to 21, 1 to 22, 1 to 23, 1 to 24, 1 to 25, 1 to 26, 1 to 27, 1 to 28, 1 to 29, 1 to 30, 1 to 31, 1 to 32, 1 to 33, 1 to 34, 1 to 35, 1 to 36, 1 to 37, 1 to 38, 1 to 39, 1 to 40, 1 to 41, 1 to 42, 1 to 43, 1 to 44, 1 to 45, 1 to 46, 1 to 47, 1 to 48, 1 to 49 or 1 to 50 of rhinovirus capsid proteins VP1, VP2, VP3 or VP4.

These peptides can be used in a respective composition in preventing and/or treating a rhinovirus infection.

Another aspect of the present invention relates to a pharmaceutical composition comprising at least one polypeptide (protein) comprising an amino acid sequence consisting of a stretch of at least 80 consecutive amino acid residues of at least one full-length capsid protein of a rhinovirus for preventing and/or treating a rhinovirus infection.

It surprisingly turned out that the administration of at least one polypeptide comprising an amino acid sequence consisting of a stretch of at least 80 consecutive amino acid residues of at least one full-length capsid protein of a rhinovirus induces in an individual the formation of antibodies directed to rhinoviruses, in particular to the capsid proteins of rhinoviruses.

The polypeptides and peptides of the composition of the present invention induce—as mentioned above—the formation of antibodies, in particular, the formation of IgA. IgA plays an important role in mucosal immunity. More IgA is produced in mucosal linings than all other types of antibody combined. In its secretory form, IgA is the main immunoglobulin found in mucous secretions, including tears, saliva, intestinal juice and secretions from the respiratory epithelium. It is also found in small amounts in blood. It was surprisingly found that antibodies of the IgA class are predominantly formed (compared to other antibody classes) when the peptides according to the present invention are administered to an individual. This shows that the peptides of the present invention allow a superior protection against rhinovirus infections since the primary infection route of rhinoviruses is the respiratory tract, in particular the mucous membranes thereof, and IgA is known to play a critical role in mucosal immunity. The stretch of consecutive amino acid residues may preferably consist of at least 90, 100, 110, 120, 150, 200, 250, 260, 270, 280, 290, or even of all amino acid residues of the at least one full-length capsid protein. In a particular preferred embodiment of the present invention the stretch of consecutive amino acid residues comprises at least 90, in particular 100, amino acid residues.

Rhinoviruses are composed of a capsid that contains four viral proteins VP1, VP2, VP3 and VP4. VP1, VP2, and VP3 form the major part of the protein capsid. Therefore, the preferred capsid protein is VP1, VP2 or VP3.

In a particular preferred embodiment the rhinovirus capsid protein is VP1, preferably VP1 of human rhinovirus 89. A particular preferred polypeptide to be used in the composition of the present invention consists of or comprises the following amino acid sequence: M N P V E N Y I D S V L N E V L V V P N I Q P S T S V S S H A A P A L D A A E T G H T S S V Q P E D M I E T R Y V I T D Q T R D E T S I E S F L G R S G C I A M I E F N T S S D K T E H D K I G K G F K (SEQ ID NO:7)(amino acid residues 1 to 100 of VP1 of human rhinovirus 89).

Exemplary capsid proteins to be used according to the present invention include VP1 proteins of human rhinovirus strains 1, in particular 1A and 1B, 2, 3, 6, 14, 15, 16, 18, 23, 25, 29, 35, 37, 44, 54, 72, 83, 86, 89, 92 and C. The respective amino acid sequences are identified in the following table:

TABLE A

| No. | Human Rhinovirus (HRV) | GenBank | Amino Acid Sequence | |
|---|---|---|---|---|
| 1 | HRV_1A | AAQ19855.1 | NPVENYIDEV LNEVLVVPNI KESHHTTSNS APLLDAAETG HTSNVQPEDA IETRYVITSQ TRDEMSIESF LGRSGCVHIS RIKVDYTDYN GQDINFTKWK ITLQEMAQIR RKFELFTYVR FDSEITLVPC IAGRGDDIGH IVMQYMYVPP GAPIPSKRND FSWQSGTNMS IFWQHGQPFP RFSLPFLSIA SAYYMFYDGY DGDNTSSKYG SVVTNDMGTI CSRIVTEKQK HSVVITTHIY HKAKHTKAWC PRPPRAVPYT HSHVTNYMPE TGDVTTAIVR RNTITTA | (SEQ ID NO: 8) |
| 2 | HRV_1B | AAQ19856.1 | NPVENYIDEV LNEVLVVPNI KESHHTTSNS APLLDAAETG HTSNVQPEDA IETRYVMTSQ TRDEMSIESF LGRSGCVHIS RIKVDYNDYN GVNKNFTTWK ITLQEMAQIR RKFELFTYVR FDSEVTLVPC IAGRGDDIGH VVMQYMYVPP GAPIPKTRND FSWQSGTNMS IFWQHGQPFP RFSLPFLSIA SAYYMFYDGY DGDNSSSKYG SIVTNDMGTI CSRIVTEKQE HPVVITTHIY HKAKHTKAWC PRPPRAVPYT HSRVTNYVPK TGDVTTAIVP RASMKTV | (SEQ ID NO: 9) |
| 3 | HRV_2 | AAQ19857.1 | NPVENYIDEV LNEVLVVPNI NSSNPTTSNS APALDAAETG HTSSVQPEDV IETRYVQTSQ TRDEMSLESF LGRSGCIHES KLEVTLANYN KENFTVWAIN IQEMAQIRRK FELFTYTRFD SEITLVPCIS ALSQDIGHIT MQYMYVPPGA PVPNSRDDYA WQSGTNASVF WQHGQAYPRF SLPFLSVASA YYMFYDGYDE QDQNYGTAST NNMGSLCSRI VTEKHIHKVH IMTRIYHKAK HVKAWCPRPP RALEYTRAHR TNFKIEDRSI QTAIVTRPII TTA | (SEQ ID NO: 10) |
| 4 | HRV_3 | AAQ19858.1 | GLSDELEEVI VEKTKQTLAS VSSGPKHTQS VPALTANETG ATLPTRPSDN VETRTTYMHF NGSETDVESF LGRAACVHVT EIKNKNAAGL DNHRKEGLFN DWKINLSSLV QLRKKLELFT YVRFDSEYTI LATASQPEAS SYSSNLTVQA MYVPPGAPNP KEWDDYTWQS ASNPSVFFKV GETSRFSVPF VGIASAYNCF YDGYSHDDPD TPYGITVLNH MGSMAFRVVN EHDVHTTIVK IRVYHRAKHV EAWIPRAPRA LPYVSIGRTN YPRDSKTIIK KRTNIKTY | (SEQ ID NO: 11) |
| 5 | HRV_6 | AAQ19861.1 | GLGDELEEVI VEKTKQTLAS VSSGPKHTQS VPILTANETG ATMPTNPSDN VETRTTYMHF NGSETDVESF LGRAACVHIT EIENKNPADI QNQKEEKLFN DWKINFSSLV QLRKKLELFT YIRFDSEYTI LATASQPKSN YASNLVVQAM YVPPGAPNPE KWDDFTWQSA SNPSVFFKVG | |

TABLE A-continued

| No. | Human Rhinovirus (HRV) | GenBank | Amino Acid Sequence |
|---|---|---|---|
| | | | DTSRFSVPFV GLASAYNCFY DGYSHDDKDT PYGITVLNHM GSIAFRVVNE HDAHKTLVKI RVYHRAKHVE AWIPRAPRAL PYETIGRTNY PKKNKIVPVI KKRENITTY (SEQ ID NO: 12) |
| 6 | HRV_14 | AAQ19869.1 | GLGDELEEVI VEKTKQTVAS ISSGPKHTQK VPILTANETG ATMPVLPSDS IETRTTYMHF NGSETDVECF LGRAACVHVT EIQNKDATGI DNHREAKLFN DWKINLSSLV QLRKKLELFT YVRFDSEYTI LATASQPDSA NYSSNLVVQA MYVPPGAPNP KEWDDYTWQS ASNPSVFFKV GDTSRFSVPY VGLASAYNCF YDGYSHDDAE TQYGITVLNH MGSMAFRIVN EHDEHKTLVK IRVYHRAKHV EAWIPRAPRA LPYTSIGRTN YPKNTEPVIK KRKGDIKSY (SEQ ID NO: 13) |
| 7 | HRV_15 | AAQ19870.1 | NPVENYIDEV LNEVLVVPNI KESHSSTSNS APALDAAETG HTSSVQPEDM IETRYVQTSQ TRDEMSIESF LGRSGCVHIS DLKIHYEDYN KDGKNFTKWQ INLKEMAQIR RKFELFTYVR FDSEITLVPC IAAKSDNIGH VVMQYMYVPP GAPLPNKRND YTWQSGTNAS VFWQHGQPYP RFSLPFLSIA SAYYMFYDGY DGDSTESHYG TVVTNDMGTL CSRIVTEEHG TRVEITTRVY HKAKHVKAWC PRPPRAVEYT HTHVTNYKPQ DGDVTTVIPT RENVRAIVNV (SEQ ID NO: 14) |
| 8 | HRV_16 | AAQ19871.1 | NPVERYVDEV LNEVLVVPNI NESHPTTSNA APVLDAAETG HTNKIQPEDT IETRYVQSSQ TLDEMSVESF LGRSGCIHES VLDIVDNYND QSFTKWKINL QEMAQIRRKF EMFTYARFDS EITMVPSVAA KDGHIGHIVM QYMYVPPGAP IPTTRNDYAW QSGTNASVFW QHGQPFPRFS LPFLSIASAY YMFYDGYDGD TYKSRYGTVV TNDMGTLCSR IVTSEQLHKV KVVTRIYHKA KHTKAWCPRP PRAVQYSHTH TTNYKLSSEV HNDVAIRPRT NLTTV (SEQ ID NO: 15) |
| 9 | HRV_18 | ACK37374.1 | NPVE NYIDEVLNEV LVVPNVNESH AITSNSAPAL DAAETGHTSN VQPEDMIETR YVQTSQTRDE MSIESFLGRS GCIHISKLVV HYEDYNAETR NFVKWQINLQ EMAQIRRKFE MFTYVRFDSE ITLVPSVAAK GDDIGHIVMQ YMYVPPGAPI PKTRDDFAWQ SGTNASIFWQ HGQTYPRFSL PFLSIASAYY MFYDGYDGDQ TSSRYGTVAT NDMGTLCSRI VTDKHKNEVE ITTRIYHKAK HVKAWCPRPP RAVEYTHTHV TNYKPKEGRE KTAIVPRARI TMA (SEQ ID NO: 16) |
| 10 | HRV_23 | AAQ19878.1 | NPIENYVDEV LNEVLVVPNI NSSHPTTSNS APAL-DAAETG HTSNVQPEDV IETRYVQTSQ TRDEMSLESF LGRSGCIHES KLKVEIGNYD ENNFNTWNIN LQEMAQIRRK FELFTYTRFD SEITLVPCIS ALSQDIGHIT MQYMYVPPGA PIPES-RNDYA WQSGTNASIF WQHGQTYPRF SLPFLSVASA YMFYDGYNE KGTHYGTVST NNMGTLCSRV VTEKHIHDMR IMTRVYHKAK HVKAWCPRPP RALEYTRAHR TNFKIEGENV KSRVAHRPAV ITA (SEQ ID NO: 17) |
| 11 | HRV_25 | ACK37379.1 | NPIENYV DQVLNEVLVV PNIKESHPST SNSAPILDAA ETGHTSNVQP EDTIETRYVQ TTQTRDEMSI ESFLGRSGCV HTSTIETKLK HDERFKTWNI NLQEMAQIRR KFEMFTYVRF DSEITLVPSI AGRGADIGHI VMQYMYVPPG APLPTDRKHF AWQSSTNASI FWQHGQPFPR FSLPFLSVAS AYYMFYDGYN GDDHTARYGT TVVNRMGALC MRIVTNKQVH DVEVTTNIYH KAKHVKAWCP RPPRAVPYKY VDFNNYAASD NVDIFIQPRN SLKTA (SEQ ID NO: 18) |
| 12 | HRV_29 | ACK37381.1 | NPVENYV DEVLNEVLVV PNIRESHPST SNSAPILDAA ETGHTSNVQP EDTIETRYVQ TSHTRDEMSI ESFLGRSGCI HVSTIKANQA HDAKFDKWNV NLQEMAQIRR KFEMFTYVRF DSEITLVPCI AGRGNDIGHI VMQYMYVPPG |

TABLE A-continued

| Human Rhinovirus No.(HRV) | | GenBank | Amino Acid Sequence |
|---|---|---|---|
| | | | APVPNDRNHF AWQSGTNASI FWQHGQPFPR FSLPFLSVAS AYYMFYDGYN GGDHTATYGT TVVNRMGTLC VRIVTGKQAH DVQVTTSIYH KAKHVKAWCP RPPRVVPYKY VGLTNYTLKE EDTVVESRPS LMTA (SEQ ID NO: 19) |
| 13 | HRV_35 | ACK37443.1 | GLGEELEEV IVEKTKQTVA SIASGSKHTQ SVPTLTANET GASMPVXPSD SVETRLTYMH FKGSETDVES FLGRAACVHM TEIVNKNPAX STNQKQDKLF NDWRINLSSL VQFRKKLELF TYVRFDSEYT ILATASQPDN SKYSSNLTVQ AMYVPPGAPN PEAWNDYTWQ SASNPSVFFK VGDTSRFSVP FVGLASAYNC FYDGYSHDDE NTPYGITVLN HMGSMAFRIV NDHDVHTTLV KIRVYHRAKH VQAWIPRAPR ALPYVSIGRS NYDKSAKPVI KRREQITKY (SEQ ID NO: 20) |
| 14 | HRV_37 | AAQ19892.1 | GLGDELEEVI VEKTKQTLAS ISSGPKHTQS VPTLTANETG ATMPTNPSDN VETRTTYMHF NGSETDIESF LGRAACVHIT EIENKNSTGS VNHKSDKLFN DWKINLSSLV QLRKKLELFT YVRFDSEYTI LATASQPSKS NYASNLVVQA MYVPPGAPNP KEWNDFTWQS ASNPSVFFKV GDTARFSVPF VGLASAYNCF YDGYSHDDEN TPYGITVLNH MGSMAFRVVN EHDAHTTLVK IRVYHRAKHV EAWIPRAPRA LPYEAIGKTN YPKMITPVIK KRDNITTY (SEQ ID NO: 21) |
| 15 | HRV_44 | AAQ19899.1 | NPVENYVDEV LNEVLVVPNI RESHPSISNS APIL-DAAETG HTSNVQPEDT IETRYVQTSQ TRDEMSIESF LGRSGCIHVS TIKTNQAHNT KFDKWNINLQ EMAQIRRKFE MFTYVRFDSE ITLVPCIAGR GDDIGHIVMQ YMYVPPGAPV PDDRIHFAWQ SGNNASIFWQ HGQPFPRFSL PFLSVASAYY MFYDGYNGGD HTATYGTTVV NRMGTLCVRI VTGKQAHDVQ VTTSIYHKAK HVKAWCPRPP RVVPYKYVGL TNYTLKETDT VVEPRHSIMT A (SEQ ID NO: 22) |
| 16 | HRV_54 | ACK37394.1 | NPVERYVD EVLNEVLVVP NIRESHPATS NSAPALDAAE TGHTSGIQPE DTIETRFVQT SQTRDEMSIE SFLGRAGCIH ESTITIQNDV EYNDHHFKKW DITLQEMAQI RRKFEFFTYV RFDSEITLVP CIAGKGVDIG HIVMQFMYVP PGAPKPEKRN DYTWESSTNP SIFWQHGQAY PRFSLPFLSI ASAYYMFYDG YDGDAPGSRY GTSVTNHMGT LCSRVVTGKQ KHPVEITTRV YH-KAKHIRAW CPRAPRAVFY THTRSTNYMP REGDPTIFLK HRTNLVTA (SEQ ID NO: 23) |
| 17 | HRV_72 | ACK37409.1 | LN DELEEVIVEK TKQTLASISS GPKYTQSVPT LTANETGATM PTLPSDNVET RTTYMHFNGS ETDIECFLGR AACVHVTEIE NKNPNGISNH KAEKLFNDWK ISLSSLVQLR KKLELFTYVR FDSEYTILAT ASQPDTANYS SNLVVQAMYV PPGAPNPVEW DDYTWQSASN PSVFFKVGDT SRFSVPYVGL ASAYNCFYDG YSHDDAETQY GISVLNHMGS MAFRIVNEHD THRTLVKIRV YHRA-KHIEAW VPRAPRALPY TSIGRTNYPK NPKPVIKKRE GDIKTY (SEQ ID NO: 24) |
| 18 | HRV_83 | ACK37417.1 | GLNDELEEV IVEKTRQTLA SVASGPKHTQ SVPILTANET GATMPTQPSD NVETRTTYMH FNGSETDIES FLGRAACVHM VEIVNKNPLN IKNQKREKLF NEWRINLSSL VQLRKKLELF TYARFDSEYT ILATASQPTN SSYSSDLTVQ AMYVPPGAPN PTKWDDYTWQ SASNPSVFFK VGDTARFSVP FVGLASAYNC FYDGYSHDDE DTPYGITVLN HMGSMAFRVV NEHDAHTTEV KIRVY-HRAKH VQVWVPRAPR ALPYVSIGRT NYERQNIKPV IEKRTSIKQY (SEQ ID NO: 25) |
| 19 | HRV_86 | ACK37420.1 | LG DELEEVIVEK TKQTLASVAT GSKYTQKVPS LTANETGATM PTVPSDNIET RTTYMNFTGS ETDVECFLGR AACVHITEIE NKDPTDIENQ KEAKLFNDWK INLSSLVQLR KKLELFTYVR |

TABLE A-continued

| Human Rhinovirus No. (HRV) | GenBank | Amino Acid Sequence |
|---|---|---|
| | | FDSEYTILAT ASQPTQSSYS SNLTVQAMYV PPGAPNPKTW NDYTWQSASN PSVFFKVGDT ARFSVPFVGL ASAYSCFYDG YSHDNEDTPY GITVLNHMGS IAFRVVNDHD LHKTVVKIRV YHRA-KHIQTW IPRAPRALPY ETIGRTNFPR NPPKIIKKRD TINTY (SEQ ID NO: 26) |
| 20 HRV_89 | AAQ19944.1 | NPVENYIDSV LNEVLVVPNI QPSTSVSSHA APALDAAETG HTSSVQPEDM IETRYVITDQ TRDETSIESF LGRSGCIAMI EFNTSSDKTE HDKIGKGFKT WKVSLQEMAQ IRRKYELFTY TRFDSEITIV TAAAAQGNDS GHIVLQFMYV PPGAPVPEKR DDYTWQSGTN ASVFWQEGQP YPRFTIPFMS IASAYYMFYD GYDGDSAASK YGSVVTNDMG TICVRIVTSN QKHDLNIVCR IYHKAKHIKA WCPRPPRAVA YQHTHSTNYI PSNGEATTQI KTRPDVFTVT NV (SEQ ID NO: 27) |
| 21 HRV_92 | ACK37425.1 | GLNDELEEV IVEKTKQTLA SITSGPKHTQ SVPTLTANET GATMPTQPSD NVETRTTYMH FNGSETDVEN FLGRAACVHM VEIVNKNPEG LENQKEHKLF NDWRINLSSL VQLRKKLELF TYVRFDSEYT ILATASQPTS SKYSSSLTVQ AMYVPPGAPN PTKWDDYTWQ SASNPSVFFK VGDTARFSVP FVGLASAYNC FYDGYSHDDE DTPYGITVLN HMGSMAFRIV NEHDAHTTEV KIRVYHRAKH VEAWIPRAPR ALPYVSIGRT NYNKQAIVPV IKKRSLITNY (SEQ ID NO: 28) |
| 22 HRV_C | ACN94256.1 | NPVEQFVDNV LEEVLVVPNT QPSGPIHTTK PTAL-SAMEIG ASSDVKPEDM IETRYVVNSR TNDEATIENF LGRSALWANV NMTDGYATWS ITYQGNAQIR KKLELFTYVR FDLEITIITS SSDLIQIMYV PPGANTPRSN NATEWNTASN PSIFFQPGNG FPRFTIPFTG LGSAYYMFYD GYDIVSHENG IYGISTTNDM GSLCFRTPNN SSGTEIIRVF GKPKHTRAWI PRPPRATG (SEQ ID NO: 29) |
| 23 HRV_C | YP_001552435.1 | NPVEDYIDKVVDTVLQVPNTQPSGPQHSIQPSALGAM EIGASSITIPGDLIETRYVINSNINSEALIENFMGRSAL WAKIQVANGFAKWDINFQEHAQVRKKFEMFTYARFD MEVIVVINNTGLVQIMFVPPGIDAPDSIDSRLWDSASN PSVFYQPKSGFPRFTIPFTGLGSAYYMFYDGYDVPRN KSNAVYGITSTNDMGTLCFRAMEDTNEHSIRVFVKPK HTIAWIPRPPRATQYTHKFSTNYHVKKPDDTTGL-LIQKHFINHRTDIKTA (SEQ ID NO: 45) |

The most preferred capsid proteins are derived from human rhinovirus 89.

According to a preferred embodiment of the present invention the rhinovirus is a rhinovirus strain selected from the group consisting of rhinovirus strain 89 and rhinovirus strain 14.

Of course, in order to further enhance the crossreactivity of the vaccine of the present invention, one or more other capsid proteins of one or more other rhinovirus serotypes can be used in said vaccine (e.g. VP1 of human rhinovirus 89 in combination with VP1 of human rhinovirus 14).

The capsid proteins of rhinovirus strain 89 and rhinovirus strain 14 show cross reactivity with most of the about 100 known rhinovirus strains. The administration of a polypeptide of the present invention derived from one of said rhinovirus strains induces the formation of antibodies, in particular of IgA, directed against most of the human rhinovirus serotypes. Therefore, it is especially preferred to use polypeptides derived from the capsid proteins of said rhinovirus strains.

According to a particular preferred embodiment the capsid protein is of human rhinovirus 89 and comprises the following amino as well as nucleic acid sequence:

VP1 of human rhinovirus 89:

(SEQ ID NOS: 30 and 59)

```
ATG AAC CCG GTG GAA AAC TAT ATT GAT AGC GTG
     N   P   V   E   N   Y   I   D   S   V

CTG AAC GAA GTG CTG GTG GTG CCG AAC ATT CAG CCG
 L   N   E   V   L   V   V   P   N   I   Q   P

AGC ACC AGC GTG AGC AGC CAT GCG GCG CCG GCG CTG
 S   T   S   V   S   S   H   A   A   P   A   L

GAT GCG GCG GAA ACC GGC CAT ACC AGC AGC GTG CAG
 D   A   A   E   T   G   H   T   S   S   V   Q

CCG GAA GAT ATG ATT GAA ACC CGT TAT GTG ATT ACC
 P   E   D   M   I   E   T   R   Y   V   I   T
```

-continued

```
GAT CAG ACC CGT GAT GAA ACC AGC ATT GAA AGC TTT
 D   Q   T   R   D   E   T   S   I   E   S   F
CTG GGC CGT AGC GGC TGC ATT GCG ATG ATT GAA TTT
 L   G   R   S   G   C   I   A   M   I   E   F
AAC ACC AGC AGC GAT AAA ACC GAA CAT GAT AAA ATT
 N   T   S   S   D   K   T   E   H   D   K   I
GGC AAA GGC TTT AAA ACC TGG AAA ATT AGC CTG CAG
 G   K   G   F   K   T   W   K   I   S   L   Q
GAA ATG GCG CAG ATT CGT CGT AAA TAT GAA CTG TTT
 E   M   A   Q   I   R   R   K   Y   E   L   F
ACC TAT ACC CGT TTT GAT AGC GAA ATT ACC ATT GTG
 T   Y   T   R   F   D   S   E   I   T   I   V
ACC GCG GCG GCG GCG CAG GGC GAT GAT AGC GGC CAT
 T   A   A   A   A   Q   G   D   D   S   G   H
ATT GTG CTG CAG TTT ATG TAT GTG CCG CCG GGC GCG
 I   V   L   Q   F   M   Y   V   P   P   G   A
CCG GTG CCG GAA AAA CGT GAT GAT TAT ACC TGG CAG
 P   V   P   E   K   R   D   D   Y   T   W   Q
AGC GGC ACC AAC GCG AGC GTG TTT TGG CAG GAA GGC
 S   G   T   N   A   S   V   F   W   Q   E   G
CAG CCG TAT CCG CGT TTT ACC ATT CCG TTT ATG AGC
 Q   P   Y   P   R   F   T   I   P   F   M   S
ATT GCG AGC GCG TAT TAT ATG TTT TAT GAT GGC TAT
 I   A   S   A   Y   Y   M   F   Y   D   G   Y
GAT GGC GAT AGC GCG GCG AGC AAA TAT GGC AGC GTG
 D   G   D   S   A   A   S   K   Y   G   S   V
GTG ACC AAC GAT ATG GGC ACC ATT TGC GTG CGT ATT
 V   T   N   D   M   G   T   I   C   V   R   I
GTG ACC AGC AAC CAG AAA CAT GAT CTG AAC ATT GTG
 V   T   S   N   Q   K   H   D   L   N   I   V
TGC CGT ATT TAT CAT AAA GCG AAA CAT ATT AAA GCG
 C   R   I   Y   H   K   A   K   H   I   K   A
TGG TGC CCG CGT CCG CCG CGT GCG GTG GCG TAT CAG
 W   C   P   R   P   P   R   A   V   A   Y   Q
CAT ACC CAT AGC ACC AAC TAT ATT CCG AGC AAC GGC
 H   T   H   S   T   N   Y   I   P   S   N   G
GAA GCG ACC ACC CAG ATT AAA ACC CGT CCG GAT GTG
 E   A   T   T   Q   I   K   T   R   P   D   V
```

-continued

```
TTT ACC GGC ACC AAC GTG
 F   T   G   T   N   V
TAA
stop
3'
```

VP2 of human rhinovirus 89:
(SEQ ID NOS: 31 and 32)

```
5'
ATG AGC CCA ACC GTG GAA GCG TGC GGT TAC AGC
     S   P   T   V   E   A   C   G   Y   S
GAC CGT CTG ATC CAG ATT ACC CGT GGT GAC AGT ACT
 D   R   L   I   Q   I   T   R   G   D   S   T
ATT ACT TCT CAG GAT ACG GCG AAC GCG GTT GTT GCA
 I   T   S   Q   D   T   A   N   A   V   V   A
TAC GGT GTT TGG CCG AGC TAT CTG ACG CCG GAT GAT
 Y   G   V   W   P   S   Y   L   T   P   D   D
GCT ACT GCA ATT GAT AAA CCT ACC CAG CCT GAT ACT
 A   T   A   I   D   K   P   T   Q   P   D   T
AGC AGC AAC CGT TTC TAT ACC CTG GAC TCT CGC AGC
 S   S   N   R   F   Y   T   L   D   S   R   S
TGG ACG AGT GCC AGC AGC GGG TGG TGG TGG AAA CTG
 W   T   S   A   S   S   G   W   W   W   K   L
CCA GAC GCA CTG AAG AAT ATG GGT ATC TTT GGT GAA
 P   D   A   L   K   N   M   G   I   F   G   E
AAT ATG TTT TAT CAT TTT CTG GGT CGT TCT GGC TAT
 N   M   F   Y   H   F   L   G   R   S   G   Y
ACG ATC CAC GTA CAG TGC AAT AGC AGC AAA TTT CAT
 T   I   H   V   Q   C   N   S   S   K   F   H
CAG GGC CTG CTG ATC GTG GCG GCT ATT CCG GAG CAT
 Q   G   L   L   I   V   A   A   I   P   E   H
CAG CTG GCC AGC GCT ACC AGC GGT AAT GTA AGC GTG
 Q   L   A   S   A   T   S   G   N   V   S   V
GGT TAC AAT CAT ACA CAT CCA GGT GAA CAG GGC CGC
 G   Y   N   H   T   H   P   G   E   Q   G   R
GAG GTA GTG CCG TCT CGC ACC AGT AGT GAT AAC AAG
 E   V   V   P   S   R   T   S   S   D   N   K
CGT CCG TCT GAT GAT TCT TGG CTG AAT TTT GAT GGC
 R   P   S   D   D   S   W   L   N   F   D   G
ACG CTG CTG GGC AAC CTG CCA ATT TAC CCG CAC CAG
 T   L   L   G   N   L   P   I   Y   P   H   Q
TAT ATC AAT CTG CGC ACC AAC AAC AGC GCC ACA CTG
 Y   I   N   L   R   T   N   N   S   A   T   L
```

-continued

```
ATC CTG CCT TAT GTC AAC GCC GTG CCT ATG GAC TCT
 I   L   P   Y   V   N   A   V   P   M   D   S

ATG CTG CGC CAC AAC AAT TGG TCT CTG GTG ATT ATC
 M   L   R   H   N   N   W   S   L   V   I   I

CCG ATT TGT CCG CTG CAA GTT CAA CCA GGT GGC ACA
 P   I   C   P   L   Q   V   Q   P   G   G   T

CAA TCT ATT CCG ATC ACC GTT TCT ATT AGT CCG ATG
 Q   S   I   P   I   T   V   S   I   S   P   M

TTC AGT GAG TTC AGT GGC CCA CGT AGT AAG GTC GTC
 F   S   E   F   S   G   P   R   S   K   V   V

TTC AGT ACA ACC CAA
 F   S   T   T   Q

TAA
stop
3'

VP3 of human rhinovirus 89:
                                  (SEQ ID NOS: 33 and 34)
    ATG GGC CTG CCA GTG ATG CTG ACA CCG GGG AGT
         G   L   P   V   M   L   T   P   G   S
GGT CAG TTC CTG ACG ACA GAC GAT ACC CAA AGC CCG
 G   Q   F   L   T   T   D   D   T   Q   S   P
AGT GCA TTC CCG TAT TTT CAT CCA ACA ACA AAG GAA ATC
 S   A   F   P   Y   F   H   P   T   K   E   I
TTT ATT CCG GGG CAG GTT CGT AAC CTG ATT GAG ATG
 F   I   P   G   Q   V   R   N   L   I   E   M
TGT CAA GTA GAC ACT CTG ATC CCG GTG AAC AAC ACT
 C   Q   V   D   T   L   I   P   V   N   N   T
CAG GAA AAC GTG CGC AGC GTG AAT ATG TAC ACG GTC
 Q   E   N   V   R   S   V   N   M   Y   T   V
GAT CTG CGC ACT CAG GTA GAC CTG GCA AAG GAG GTG
 D   L   R   T   Q   V   D   L   A   K   E   V
TTC TCT ATC CCG GTG GAT ATT GCG AGC CAA CCA CTG
 F   S   I   P   V   D   I   A   S   Q   P   L
GCG ACG ACC CTG ATC GGC GAA CTG GCG AGC TAT TAC
 A   T   T   L   I   G   E   L   A   S   Y   Y
ACT CAT TGG ACG GGT AGT CTG CGT TTT AGT TTC ATG
 T   H   W   T   G   S   L   R   F   S   F   M
TTT TGT GGC TCT GCA AGT AGC ACT CTG AAA CTG CTG
 F   C   G   S   A   S   S   T   L   K   L   L
ATT GCG TAC ACC CCG CCG GGT GTC GGT AAA CCA AAG
 I   A   Y   T   P   P   G   V   G   K   P   K
AGC CGC CGC GAA GCT ATG CTG GGT ACG CAT CTG GTG
 S   R   R   E   A   M   L   G   T   H   L   V
TGG GAT GTA GGC CTG CAA AGT ACG GCT TCT CTG GTA
 W   D   V   G   L   Q   S   T   A   S   L   V
GTC CCT TGG GTC TCT GCG AGC CAC TTT CGT TTC ACC
 V   P   W   V   S   A   S   H   F   R   F   T
ACA CCG GAC ACC TAT TCT TCT GCC GGC TAT ATT ACC
 T   P   D   T   Y   S   S   A   G   Y   I   T
TGT TGG TAT CAG ACC AAT TTT GTG GTT CCT GAT AGC
 C   W   Y   Q   T   N   F   V   V   P   D   S
ACC CCT GAT AAT GCC AAA ATG GTT TGC ATG GTT AGC
 T   P   D   N   A   K   M   V   C   M   V   S
GCC TGC AAA GAT TTC TGC CTG CGT CTG GCC CGT GAC
 A   C   K   D   F   C   L   R   L   A   R   D
ACC AAT CTG CAC ACA CAG GAA GGC GTT CTG ACC CAA
 T   N   L   H   T   Q   E   G   V   L   T   Q
TAA
stop
3'

VP4 of human rhinovirus 89:
                                  (SEQ ID NOS: 46 and 47)
5'
CAT ATG GGC GCC CAG GTG TCT CGT CAG AAC GTC GGC
 NdeI  G   A   Q   V   S   R   Q   N   V   G
```

```
ACG CAT AGC ACG CAG AAC AGT GTG TCC AAC GGC TCG
 T   H   S   T   Q   N   S   V   S   N   G   S

TCG CTG AAC TAC TTC AAC ATC AAC TAT TTT AAA GAT
 S   L   N   Y   F   N   I   N   Y   F   K   D

GCA GCC AGC TCT GGT GCG AGC CGT CTG GAT TTT AGT
 A   A   S   S   G   A   S   R   L   D   F   S

CAG GAC CCG TCC AAA TTC ACC GAC CCG GTC AAA GAT
 Q   D   P   S   K   F   T   D   P   V   K   D

GTC CTG GAA AAA GGT ATC CCG ACC CTG CAA CAC CAC
 V   L   E   K   G   I   P   T   L   Q   H   H

CAC CAC CAC CAC TAA CTC CAG
 H   H   H   H  stop XhoI 3'
```

According to a preferred embodiment of the present invention the amino acid residues 1 to 8 of the rhinovirus capsid protein VP1 have amino acid sequence NPVENYID (SEQ ID NO:50).

The sequence information given herein and known in the prior art allows to determine the peptides preferably used in the present invention. The respective amino acid ranges are mentioned above.

According to a particularly preferred embodiment of the present invention the at least one peptide is selected from the group consisting of NPVENYIDSVLNEVLVVPNIQPSTS-VSSHAA (SEQ ID NO:48) and NPVENYIDSVLNEVLV-VPNIQ (SEQ ID NO:49).

According to another preferred embodiment of the present invention the peptide according to the present invention is fused or coupled to a carrier.

Suitable carriers include but are not limited to *Limulus polyphemus* hemocyanin (LPH), *Tachypleus tridentatus* hemocyanin (TTH), and bovine serum albumin (BSA), tetanus toxoid and diphtheria toxin, DHBcAg, polyribotol ribosyl phosphate (PRP), PncPD11, Maltose Binding Proteins (MBP) and nanoparticle formulations. In one embodiment, a suitable immunogenic carrier protein is Keyhole Limpet Hemocyanin (KLH).

In order to stimulate the immune system and to increase the response to a vaccine, the composition of the present invention comprises at least one at least one pharmaceutical excipient and/or adjuvant.

According to a particularly preferred embodiment of the present invention the adjuvant is alum, preferably aluminum phosphate or aluminum hydroxide, or carbohydrate based particles (CBP).

In order to increase the efficacy of the formulation according to the present invention, all kinds of adjuvants may be used. Preferred adjuvants are, however, aluminum based compounds. Other usable adjuvants include lipid-containing compounds or inactivated mycobacteria. PBC are known, for instance, from the EP 1 356 826.

Alum is known as a Th2 driving adjuvant resulting in the formation of IgG molecules. However, it was surprisingly found that the use of alum in combination with the at least one polypeptide of the present invention results in an induction of IgA rather than IgG. The induction of IgA is particularly advantageous, because IgA is a secretory immunoglobulin found in mucosal secretions and is therefore a first line of defense against an incoming virus.

Generally, adjuvants may be of different forms, provided that they are suitable for administration to human beings. Further examples of such adjuvants are oil emulsions of mineral or vegetal origin, mineral compounds, such as aluminium phosphate or hydroxide, or calcium phosphate, bacterial products and derivatives, such as P40 (derived from the cell wall of *Corynebacterium granulosum*), monophosphoryl lipid A (MPL, derivative of LPS) and muramyl peptide derivatives and conjugates thereof (derivatives from mycobacterium components), alum, incomplete Freund's adjuvant, liposyn, saponin, squalene, etc. (see, e.g., Gupta R. K. et al. (Vaccine 11:293-306 (1993)) and Johnson A. G. (Clin. Microbiol. Rev. 7:277-289)).

According to another preferred embodiment of the present invention said formulation comprises 10 ng to 1 g, preferably 100 ng to 10 mg, especially 0.5 µg to 200 µg of said polypeptide. The polypeptide of the present invention is administered to a mammal in these amounts. However, the amount of polypeptide applied is dependent on the constitution of the subject to be treated (e.g. weight). Furthermore, the amount to be applied is also dependent on the route of administration.

According to a further preferred embodiment of the present invention the composition is adapted for intradermal, intramuscular, subcutaneous, oral, rectal, vaginal or epicutaneous administration.

Preferred ways of administration of the formulation of the present invention include all standard administration regimes described and suggested for vaccination in general (oral, transdermal, intraveneous, intranasal, via mucosa, rectal, etc). However, it is particularly preferred to administer the molecules and proteins according to the present invention subcutaneously or intramuscularly.

Another aspect of the present invention relates to a peptide as defined above. In short, the peptide of the present invention consists of a minimum of 8 and a maximum of 50 amino acid residues comprising amino acid residues 1 to 8 of a rhinovirus capsid protein selected from the group consisting of VP1, VP2, VP3 and VP4.

A further aspect of the present invention relates to the use of a polypeptide or peptide as defined above for the manufacture of a medicament for the prevention and/or treatment of a rhinovirus infection.

The medicament is preferably administered intradermally, intramuscularly, subcutaneously, orally, rectally, vaginally or epicutaneously by applying for instance patches.

Human rhinoviruses (HRVs) are the primary cause of acute respiratory tract illness (ARTI) and upper respiratory tract (URT) infections, generally known as the common cold. However, this virus can also replicate in the lower respiratory tract contributing to more severe airway dysfunctions. A significant and increasing body of evidence demonstrates that HRV is responsible for ~50% of asthma exacerbations and is one of the factors that can direct an infant immune system toward an asthmatic phenotype. Further evidence for HRV involvement in asthma is based on the seasonality of exacerbations. HRV infections occur throughout the year but usually with peaks in spring and autumn. Strong correlations have also been found between seasonal patterns of upper respiratory infections and hospital admissions for asthma.

There is no obvious pattern to the symptoms of HRV infections, so it devolves to the diagnostic laboratory only in order to confirm the presence of HRVs. Disappointingly, the routine screening for HRV strains occurs infrequently because testing is not always available or HRV infection is considered to be harmless. Currently the diagnosis of rhinovirus infections is mainly performed by direct detection of virus by PCR-based methods but positive results are seldom characterized beyond the genus level and are usually reported as 'respiratory picornaviruses'. The commonly used serodiagnosis based on the strain-specific neutralization of the infection is also impractical for large population studies. Therefore, there exists a need for improving serological techniques for the diagnosis of HRV infections and to determine whether other respiratory diseases such as asthma have been triggered by human rhinoviruses.

Therefore, another aspect of the present invention relates to a method for diagnosing in vitro a rhinovirus infection in a mammal comprising the steps of:

providing an antibody comprising sample of a mammal, contacting said sample with at least one peptide consisting of a minimum of 8 and a maximum of 50 amino acid residues comprising amino acid residues 1 to 8 of a rhinovirus capsid protein selected from the group consisting of VP1, VP2, VP3 and VP4 of rhinovirus strain 89 or rhinovirus strain 14, diagnosing a rhinovirus infection when the binding of antibodies to said at least one polypeptide is detected.

Yet another aspect of the present invention relates to a method for diagnosing in vitro a rhinovirus infection in a mammal comprising the steps of:

providing a sample of a mammal, contacting said sample with at least one polypeptide comprising an amino acid sequence consisting of a stretch of at least 80 consecutive amino acid residues of full-length capsid protein of rhinovirus strain 89 and/or rhinovirus strain 14, diagnosing a rhinovirus infection when the binding of immunoglobulins to said at least one polypeptide is detected.

Antibodies directed to the capsid proteins (in particular to VP1) of rhinovirus strains 89 and 14 are surprisingly able also to bind to capsid proteins of a broad variety of rhinovirus strains. This surprising fact is used to diagnose a rhinovirus infection caused by any rhinovirus strain in a mammal, preferably in a human. Therefore, the method of the present invention allows to diagnose a rhinovirus infection independent from a specific serotype. The at least one polypeptide has the characteristics as defined above.

The at least one polypeptide according to the present invention is preferably immobilized on a solid support. This allows to bind the antibodies binding to said at least one polypeptide to a solid support and to detect whether the sample analyzed comprises antibodies directed to rhinoviral capsid proteins. The presence of such antibodies allows the diagnosis of a rhinovirus infection.

In the method according to the present invention IgA, IgG, IgM and/or IgE are preferably measured.

According to a preferred embodiment of the present invention the sample is a blood sample, preferably serum or plasma, a sputum sample, neural lavage fluid sample or tear sample.

According to a particularly preferred embodiment of the present invention the capsid protein is VP1, VP2, VP3 or VP4.

Another aspect of the present invention relates to a method for diagnosing in vitro a respiratory disease associated with a rhinovirus infection in a mammal comprising the steps of:

providing an antibody comprising sample of a mammal, contacting said sample with a VP1, VP2, VP3 and VP4 polypeptide of a rhinovirus or a fragment thereof, determining the class of the antibodies binding to said polypeptide, and diagnosing bronchiolitis when VP3- and VP4-specific IgG1 and VP3-specific IgM antibodies are detected, asthma when VP4-specific IgG1 and VP1- and VP2-specific IgA antibodies are detected, croup when VP4-specific IgG1 antibodies are detected, convulsions when VP1-specific IgM antibodies are detected, double viral infection (HRV/Influenza) when VP1-, VP2-, VP3- and VP4-specific IgA are detected.

It was found that the presence of antibodies of a specific class/isotype directed to rhinovirus VP1, VP2, VP3 and VP4 polypeptide indicates what kind of respiratory disease an individual may suffer from. Therefore the determination of the antibody class and the antibody specificity allows to diagnose a respiratory disease in an individual. Means and methods for determining the presence of antibodies binding to a specific target are known in the art. Also the determination of the isotype/class of an antibody is known to a person skilled in the art.

According to a preferred embodiment of the present invention the sample is a blood sample, preferably serum or plasma, a sputum sample, neural lavage fluid sample or tear sample.

The fragment of the VP1, VP2, VP3 and/or VP4 polypeptide consists preferably of a minimum of 8 and a maximum of 50 amino acid residues comprising amino acid residues 1 to 8 of a rhinovirus capsid protein selected from the group consisting of VP1, VP2, VP3 and VP4.

According to another preferred embodiment of the present invention the rhinovirus is rhinovirus strain 89 and the capsid protein is VP1.

The amino acid residues 1 to 8 of the rhinovirus capsid protein have preferably amino acid sequence NPVENYID (SEQ ID NO:50).

The fragment is preferably selected from the group consisting of NPVENYIDSVLNEVLVVPNIQPSTSVSSHAA (SEQ ID NO:48) and NPVENYIDSVLNEVLVVPNIQ (SEQ ID NO:49).

The present invention is further illustrated by the following figures and examples, yet, without being restricted thereto.

FIG. 1 shows the seasonality of IgA response to VP1 in human sera taken over a period of one year. Sera from 8 allergic and 6 non-allergic patients were taken in winter, spring, summer and autumn and titers of IgA antibodies specific for VP1 were determined by ELISA and are expressed as optical value (OD 405 nm) on the y-axis. The optical values correspond to the level of antibody in the human sera. The results are shown in box plots, where 50% of the values are within the boxes and non-outliers between the bars. The line within the boxes indicates the median values.

FIG. 2 shows the VP1-specific IgA levels in a vaccinated individual over the study period. The VP1-specific IgA titers were measured by ELISA. The day of the blood donation is applied on x-axis, the optical density (OD) on y-axis. The optical value corresponds to the level of IgA antibody in human sera.

FIG. 3 shows VP1-specific IgA response in mice. Groups of mice were immunized with VP1 antigen. VP1-specific IgA titers were measured by ELISA and are expressed as optical value (OD 405 nm) on the y-axis. The optical value corresponds to the level of IgA antibody in mouse sera.

FIG. 4 shows a neutralization test with VP1 of human rhinovirus serotype 14.

FIG. 5 shows a neutralization test with VP1 of human rhinovirus serotype 89.

FIG. 6 shows the purification of recombinant VP1 proteins. (A) 89VP1 and (B) 14VP1 were stained with Coomassie blue after SDS-PAGE (left) and with an anti-His6 antibody (right) after blotting on nitrocellulose. Molecular weights in kDa are indicated at the left.

Figure 7A:
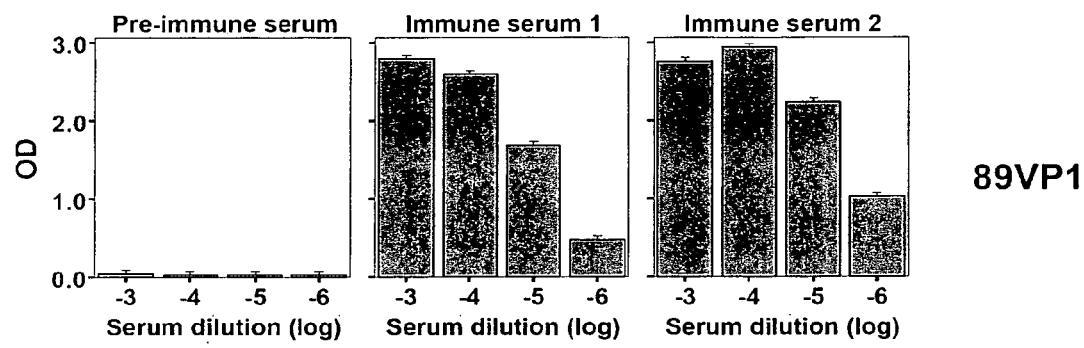
Figure 7A:
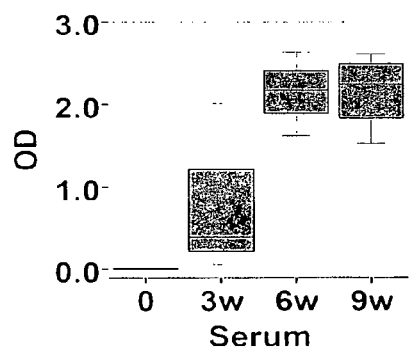

FIG. 7 shows VP1-specific immune responses of immunized rabbits and mice. (A) 89VP1- and 14VP1-specific IgG responses in rabbits. Rabbits were immunized with 89VP1 or 14VP1. Serum samples were taken on the day of the first immunization (pre-immune serum) and after the second and third injection in 3-4 weeks intervals (top of the box: Immune serum 1; Immune serum 2). Dilutions of the sera (rabbitα89VP1; rabbitα14VP1) are presented on the x-axis ($10^{-3}$-$10^{-6}$ indicated as log). IgG reactivities to the immunogens (89VP1, 14VP1) are displayed as bars. (B) A group of five mice was immunized with 89VP1. Serum samples were taken on the day of the first immunization (0) and in three weeks intervals (w3-w9) (x-axis). IgG1 reactivities are displayed for the group as box plot where 50% of the values are within the boxes and non-outliers between the bars. The lines within the boxes indicate the median values. IgG1 levels specific for 89VP1 are displayed as optical density values (y-axis).

FIG. 8 shows that anti-VP1 antibody raised against recombinant VP1 react with rhinovirus-derived VP1 and whole virus. (A) Nitrocellulose-blotted HRV14 protein extract and recombinant 14VP1 were incubated with anti-14VP1 antibodies and the corresponding pre-immune serum (pre-IS). Molecular weights in kDa are indicated at the left. (B) Electron micrographs of labelled virus preparations after negative staining. Immobilized HRV89 was incubated with anti-89VP1 IgG antibodies and the binding sites were visualized by a secondary IgG antibody probe coupled to colloidal gold particles with a diameter of 10 nm. The left micrograph gives a detail from a virus particle (VP) connected with four gold particles (GP). The right micrograph shows the control preparation using the pre-immune Ig. Bars: left micrograph, 50 nm; right micrograph, 100 nm.

Figure 9:
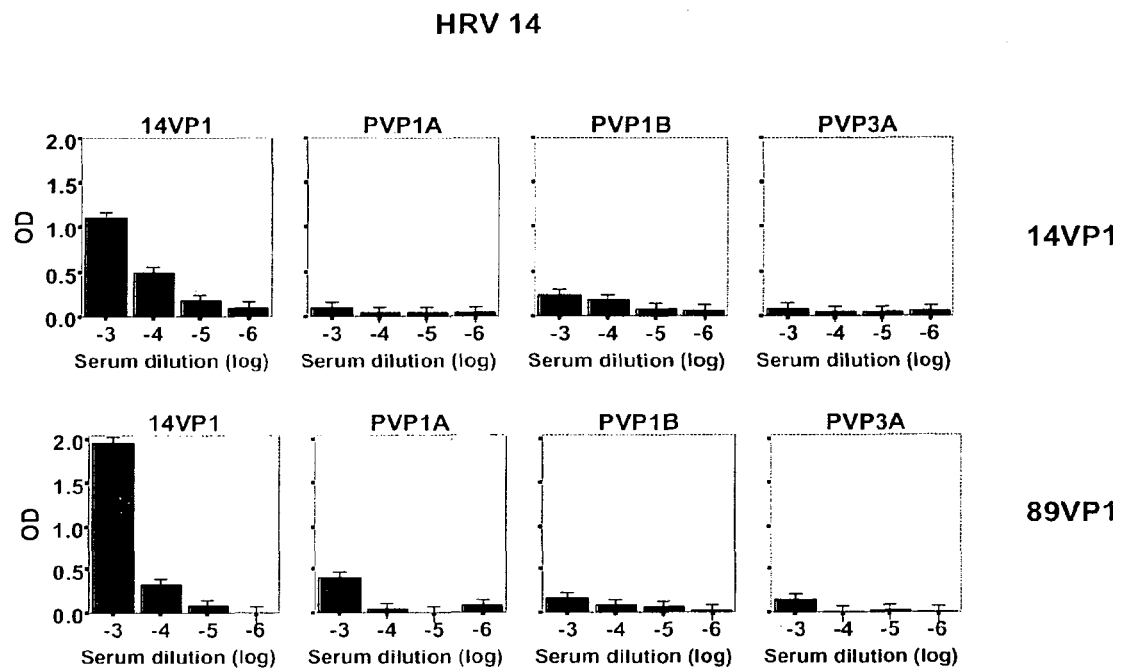

FIG. 9 shows the reactivity of rabbit antisera raised against recombinant 14VP1 protein or 14VP1-derived peptides. Rabbits were immunized with recombinant 14VP1, PVP1A, PVP1B or PVP3A (top of the box) and sera exposed to 14VP1 (top) or 89VP1 (bottom). The dilutions of the sera are displayed on the x-axis ($10^{-3}$-$10^{-6}$ indicated as log). IgG levels specific for 14VP1 and 89VP1 correspond to the optical density values (bars: y-axis).

Figure 10:
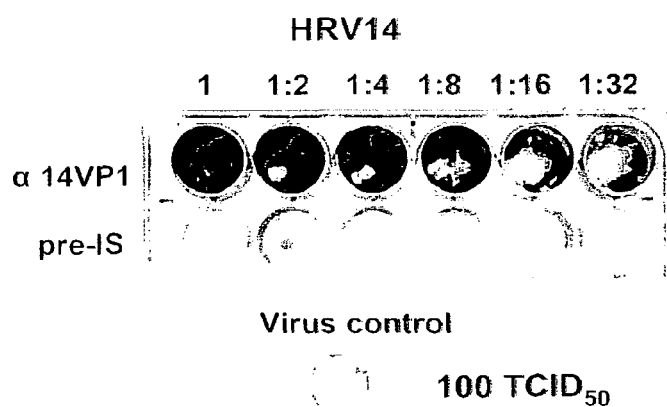

FIG. 10 shows that HRV14 is neutralized by anti-14VP1 antibodies. HRV14 at 100 $TCID_{50}$ was preincubated with serial dilutions of antiserum as indicated for 2 h at 37° C. and the mixture was added to subconfluent HeLa cells in 24 well plates. After 4 days at 34° C. remaining cells were stained with crystal violet. Pre-IS, pre-immune serum used as a control.

FIG. 11 shows (A) Phylogenetic tree of the VP1 sequences of the HRVs investigated. VP1 sequences were retrieved from the data bank and their similarity was analyzed with ClustalW. (B) Inhibition of HRV infections by the respective VP1-specific antibodies. HRVs at 100 $TCID_{50}$ were pre-incubated with twofold serial dilutions of the respective antisera at 1:2 (a) to 1:16 (d) for 3 hours at 37° C. and the mixtures were applied to subconfluent HeLa cells in 96 well plates. After incubation for 3 days at 34° C., cells were stained with crystal violet, washed, the stain was dissolved, and the OD was read at 560 nm. Mean±standard error of four independent experiments is shown.

Figure 12:
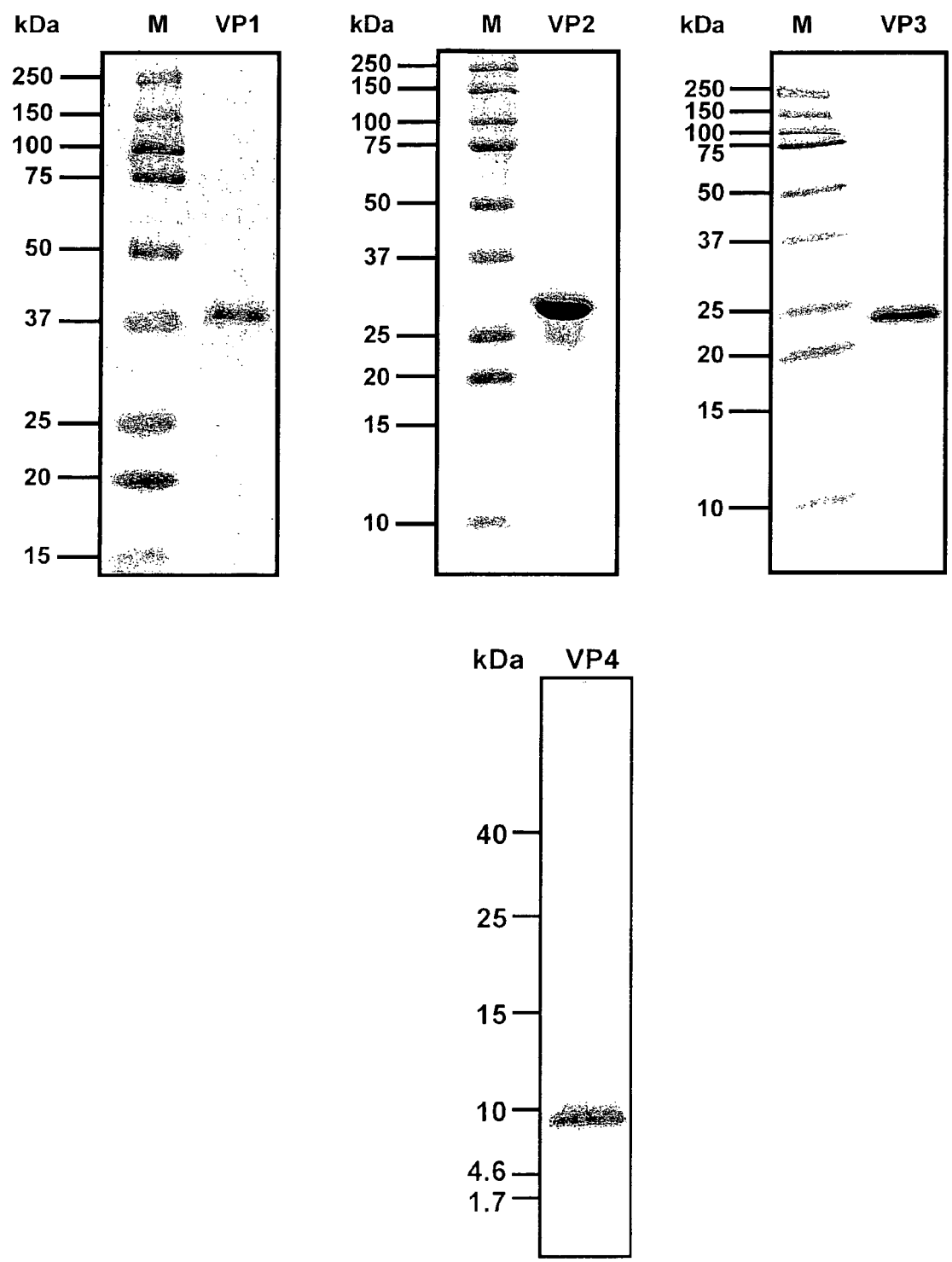

FIG. 12 shows a Coomassie blue stained 12.5% SDS-PAGE gels containing purified VP1, VP2, VP3 and VP4 his-tagged proteins (Lane 1: 5 µl molecular marker; Lane 2: 10 µl VP1; 10 µl VP2; 10 µl VP3; 10 µl VP4, respectively).

Figure 13:
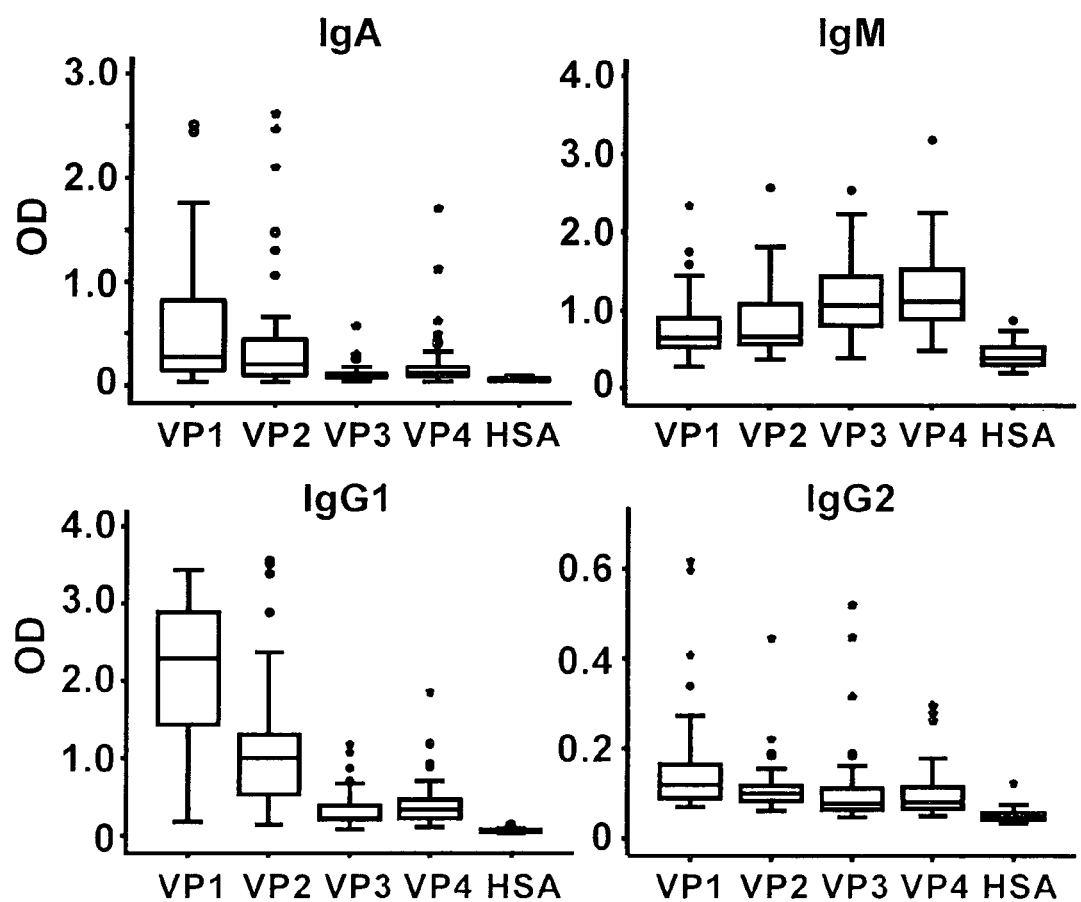

FIG. 13 shows IgA, IgM, $IgG_1$ and $IgG_2$ responses to VP1, VP2, VP3 and VP4 detected in human blood from patients with positive HRV-specific PCR test results. Fifty seven patient's sera were tested for the presence of four antibodies specific for rhinovirus-derived capsid proteins. Titers were measured by ELISA and are expressed as optical value (OD 405 nm) on the y-axis. The optical values correspond to the levels of antibodies in the human sera. The results are shown in box plots, where 50% of the values are within the boxes and non-outliers between the bars. The line within the boxes indicates the median values.

FIG. 14A shows the multiple alignment of the VP1 amino acid sequences of HRV prototype strains. Sequences were retrieved from Protein Database and aligned with GeneDoc followed by manual editing. They represent HRV serotypes belonging to different species and different receptor group: HRV37 and 89 are the major group genus A, HRV3, 14 and 72 are the major group genus B, HRV1A, 18 and 54 are the K-types and HRV1A, HRV29 and 44 are the minor group genus A. The black squares denote three epitopes derived from VP1 of the HRV89 strain.

Figure 14B:
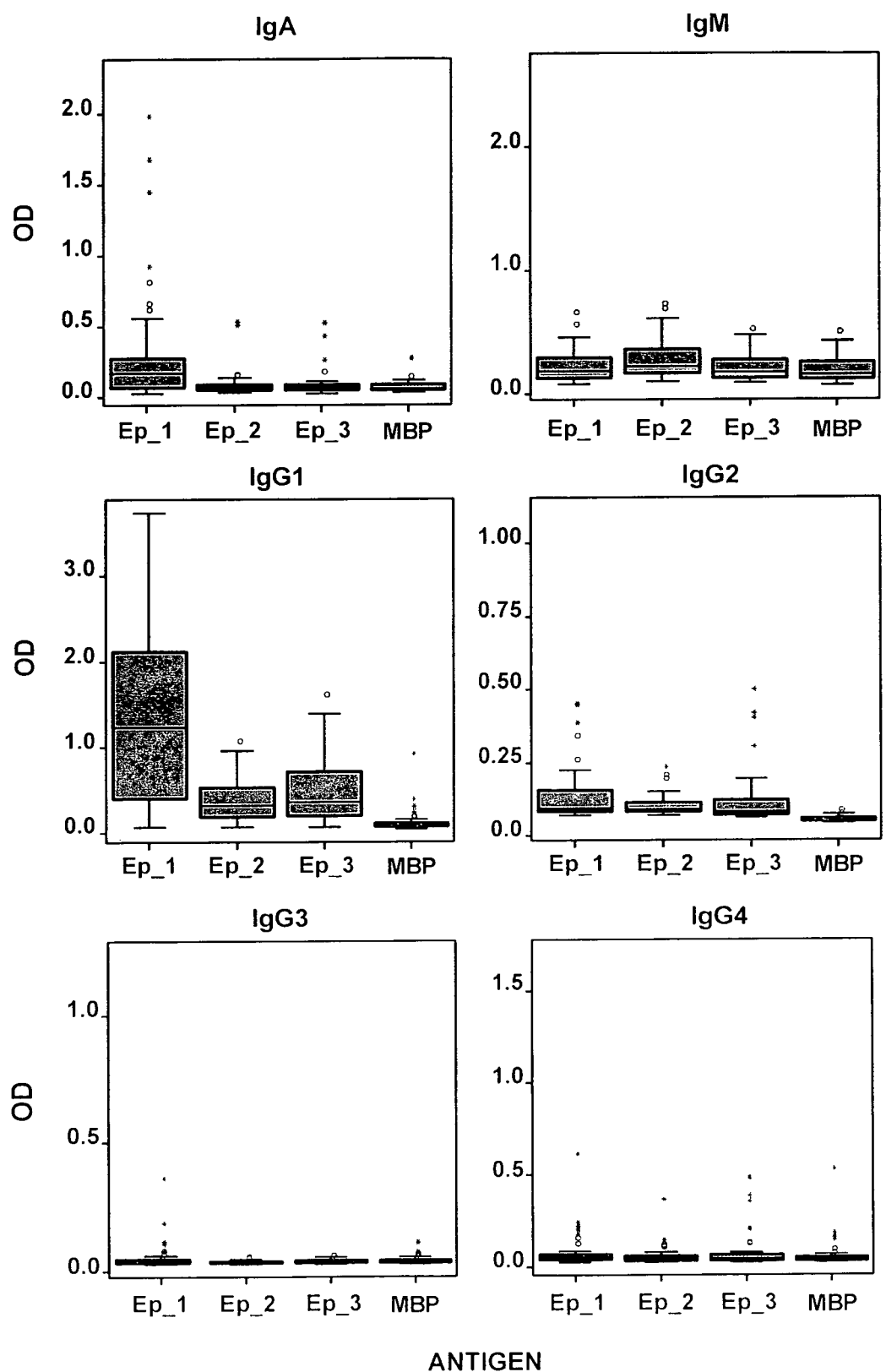

FIG. 14B shows IgA, IgM, IgG1, IgG2, IgG3 and IgG4 responses to Ep_1, Ep_2 and Ep_3 detected in human blood from patients with positive HRV-specific PCR test results. Fifty seven patients' sera were tested for six antibodies specific for VP1-derived epitopes. Titers were measured by ELISA and are expressed as optical value (OD 405 nm) on the y-axis. The optical values correspond to the level of antibody in the human blood. The results are shown in box plots, where 50% of the values are within the boxes and non-outliers between the bars. The line within the boxes indicates the median values.

Figure 15:
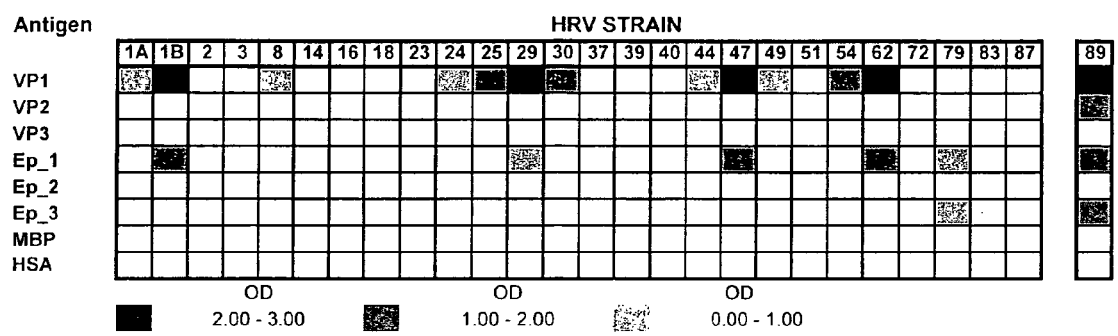

FIG. 15 shows the cross-reactivity of guinea pig IgG to recombinant VP1, VP2, VP3 and VP1-derived epitopes. However, this regards only to the recognition of the antigens (to be used for diagnosis). It is not a proof for the neutralization of each virus but indicates cross-protection. Nutralization of different HRV strains is shown in FIG. 11B. Because the data correlate we might assume that antibodies against VP1 or VP1-derived N-terminal fragment from HRV89 will also neutralize other strains when tested by neutralization tests.

Figure 16:
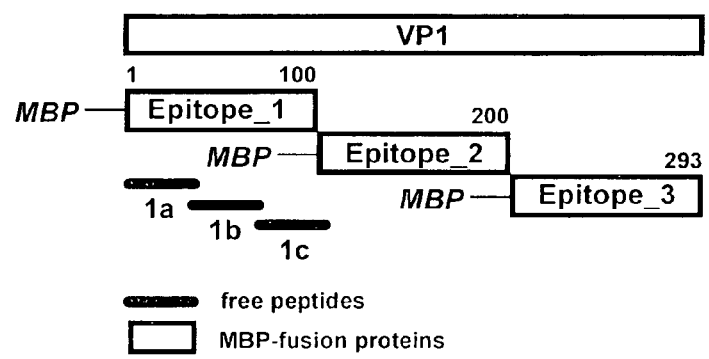

FIG. 16 shows epitope mapping of the major capsid protein VP1.

Figure 17:
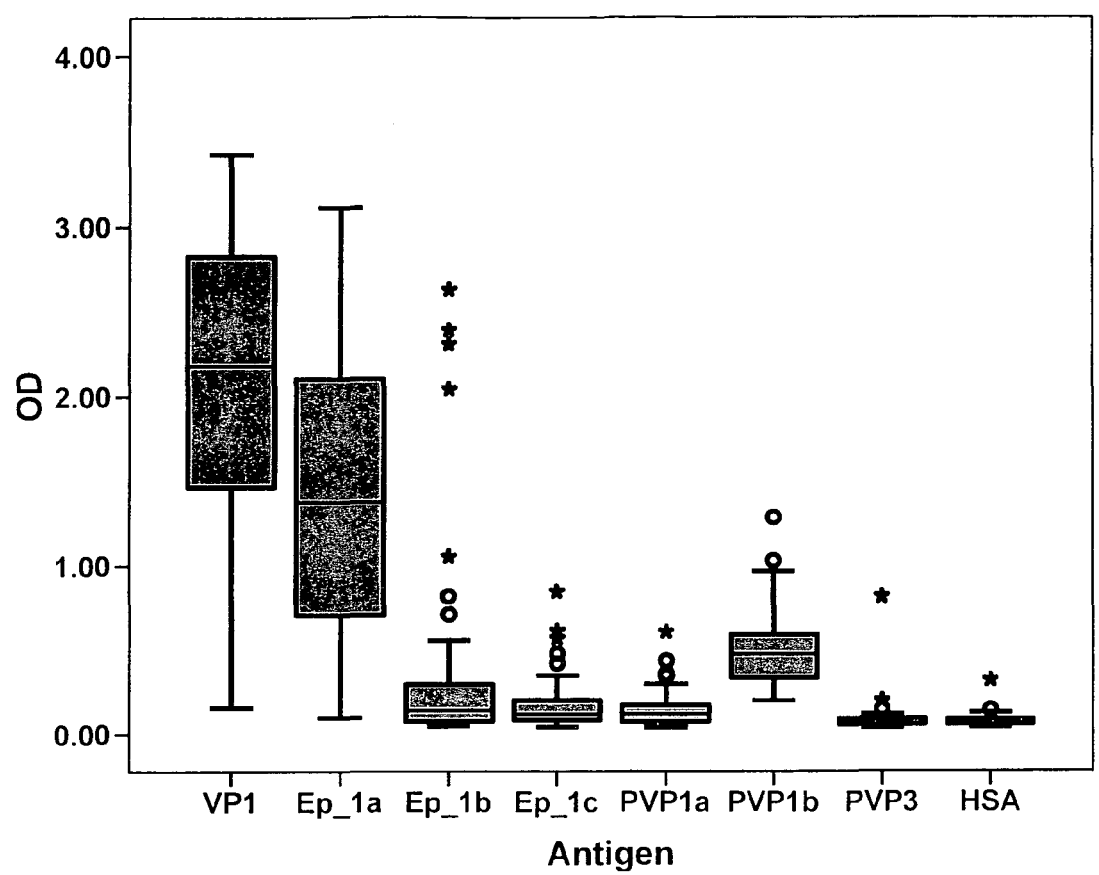

FIG. 17 shows $IgG_1$ immune response to synthetic peptides derived from N-terminal epitope of VP1 in comparison to peptides previously described (Mc Cray et al., Nature 329 (1987): 736-738) detected in human blood from patients with positive HRV-specific PCR test results.

Figure 18:
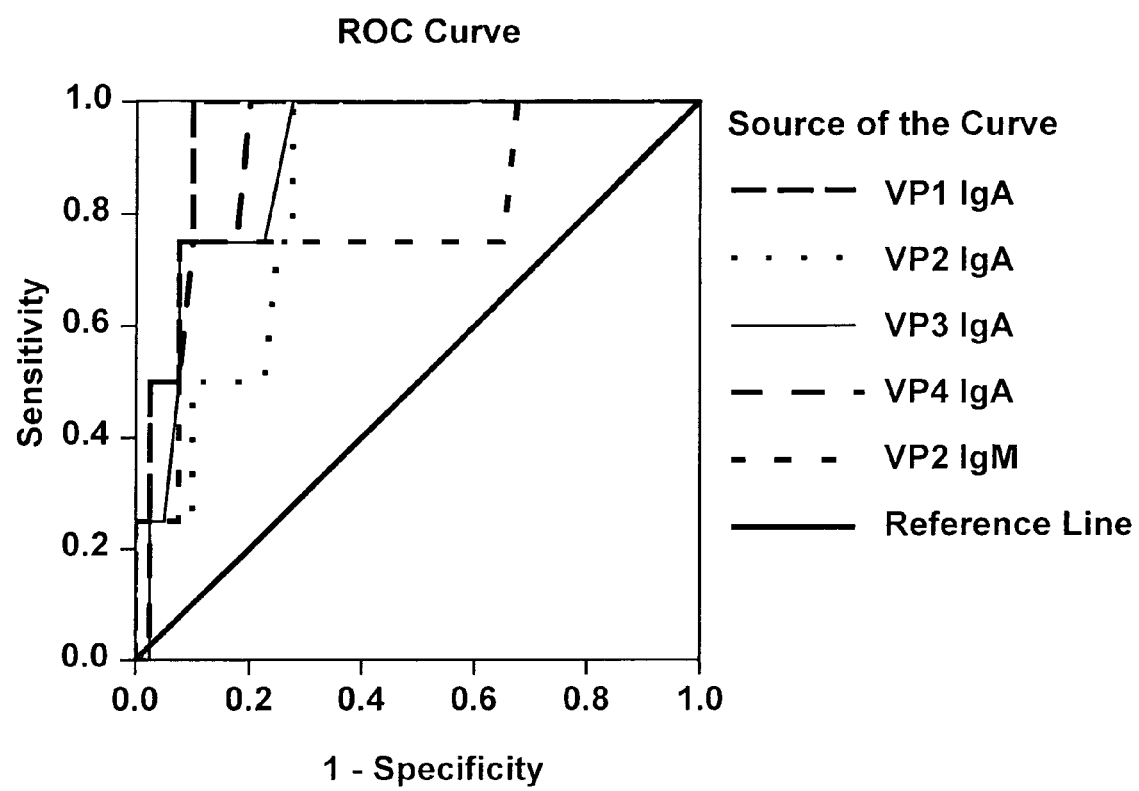

FIG. 18 shows a ROC curve for the antibody values in patients with HRV/Influenza double infection.

Figure 19A:
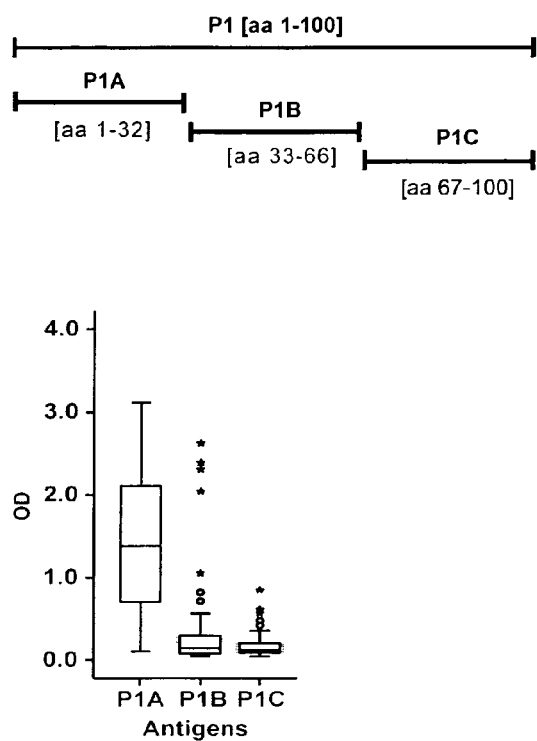
Figure 19B:
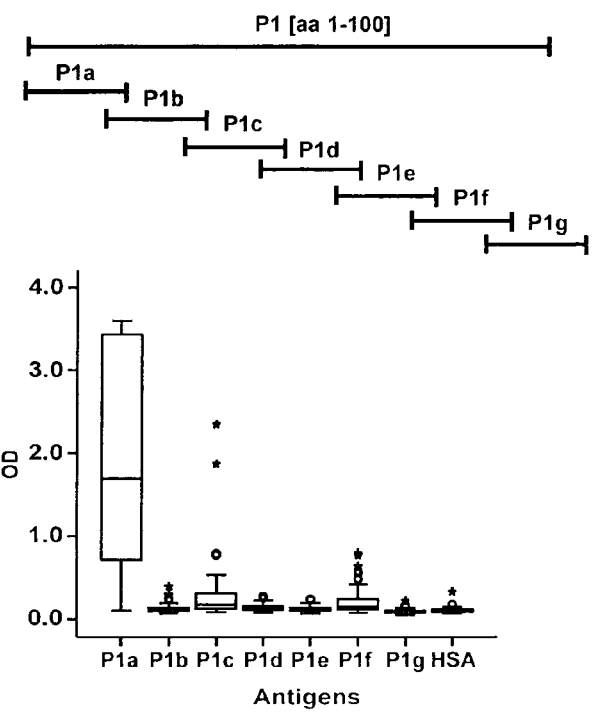

FIG. 19 shows $IgG_1$ responses to P1-derived peptides, each comprising approximately 30 (FIG. 19A) or 20 (FIG. 19B) amino acids, or P1A-derived peptides (B), each comprising 20 amino acids, detected in human blood from fifty seven patients with positive HRV-specific PCR test results. $IgG_1$ reactivities were measured by ELISA and are expressed as optical value (OD 405 nm) on the yaxis. The optical values correspond to the levels of antibodies in the human sera. The results are shown in box plots, where 50% of the values are within the boxes and non-outliers between the bars. The line within the boxes indicates the median values.

Figure 20A:
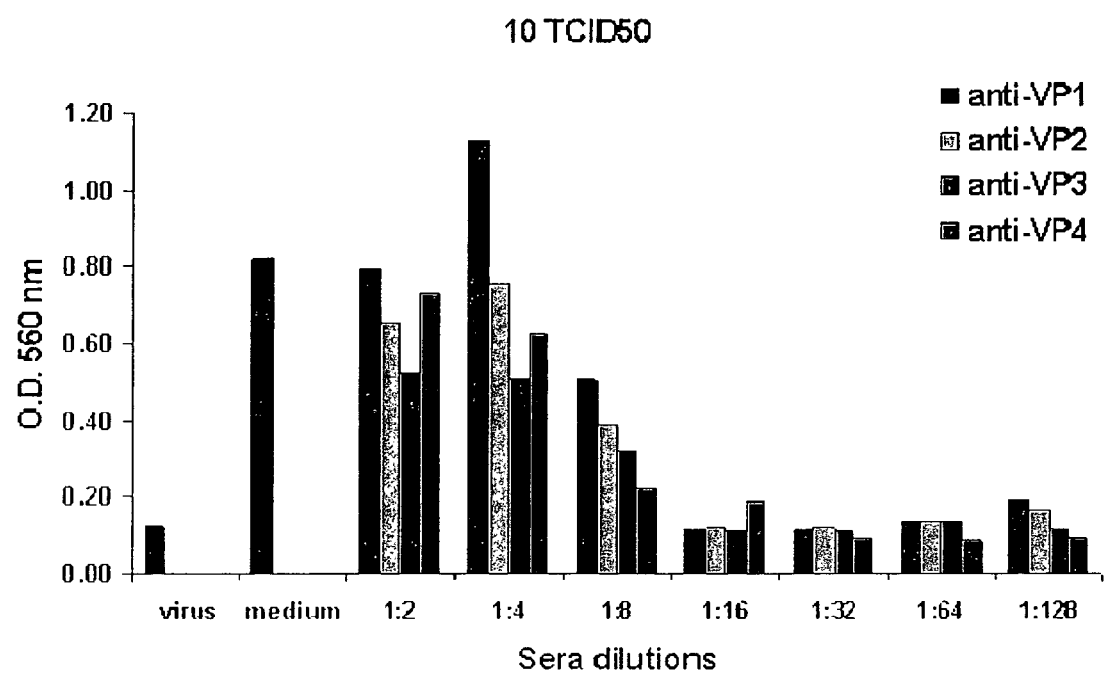
Figure 20B:
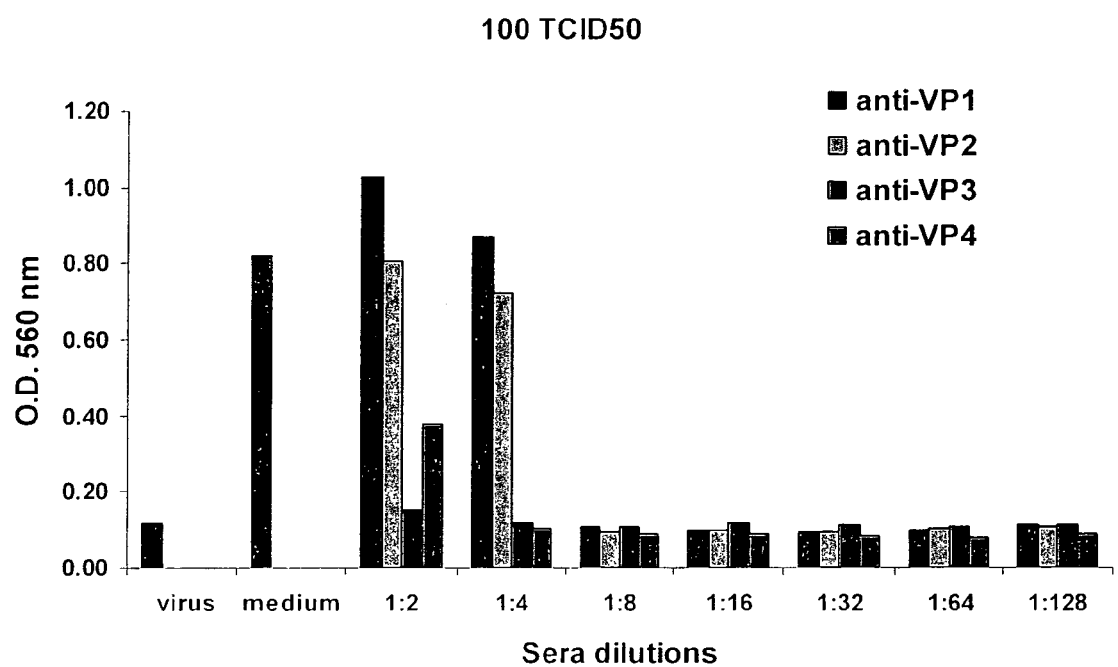
Figure 20C:
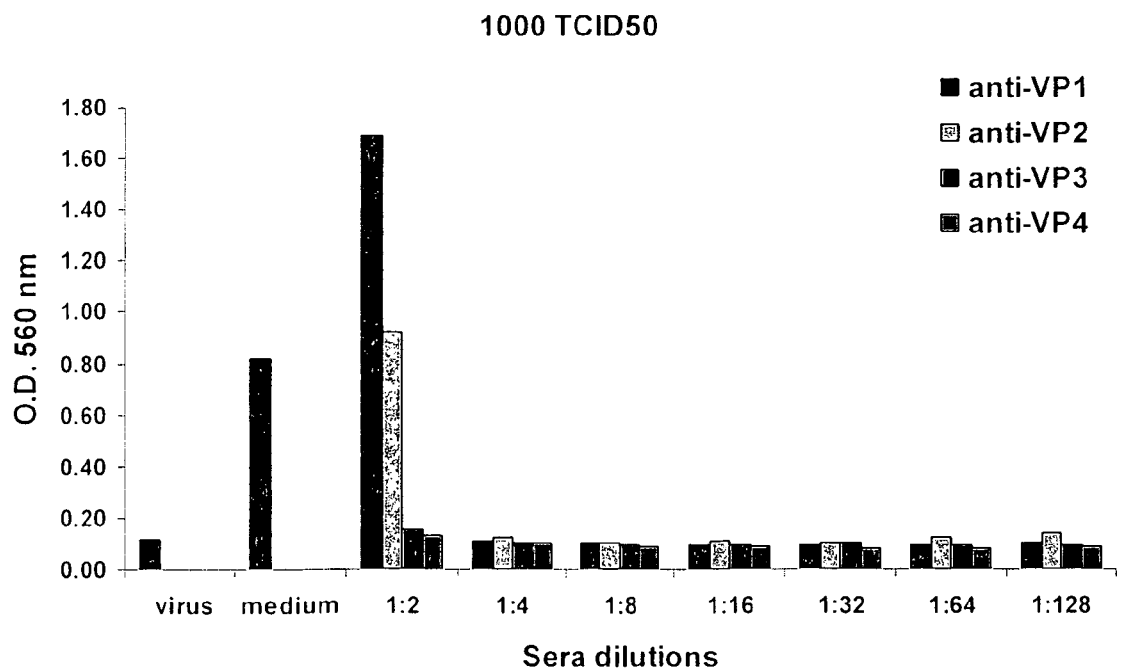

FIG. 20 shows inhibition of HRV infections by anti-VP1, anti-VP2, anti-VP3 anti-VP4 antibodies. HRVs at 10 TCID50 (A), 100 TCID50 (B) or 1000 TCID50 (C) were pre-incubated with twofold serial dilutions of the respective anti-sera 1:2 to 1:1:128 for 3 hours at 37° C. and the mixture were applied to subconfluent HeLa cells in 96 well plates. After incubation for 3 days at 34° C., cells were stained with crystal violet, washed, the stain was dissolved, and the OD was read at 560 nm.

Figure 21:
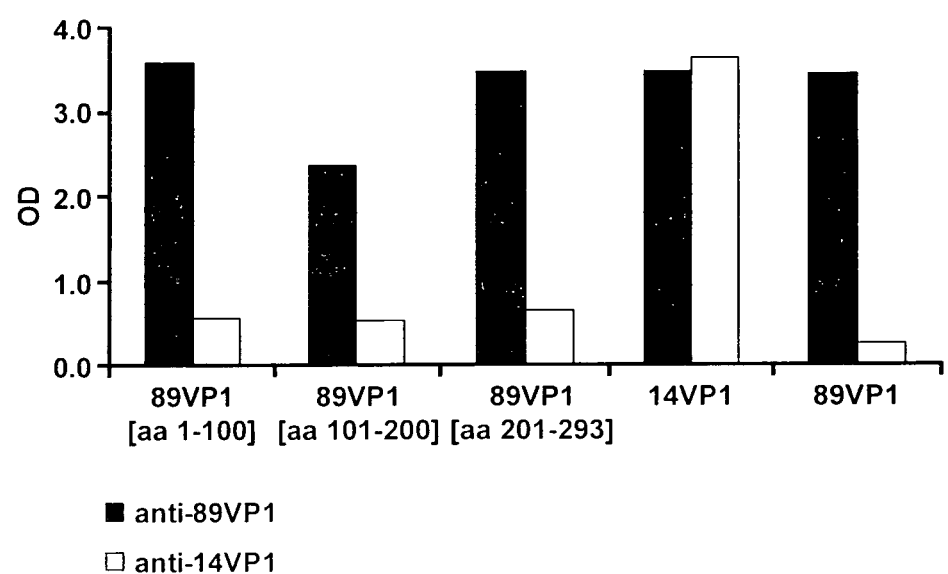

FIG. 21 shows reactivity of rabbit anti-89VP1 and anti-14VP1 antibodies with 14VP1, 89VP1 and three recombinant 89VP1 fragments. Rabbit sera were diluted 1:5000 and $A_{560}$ corresponding to bound IgG antibodies is shown on the y-axis.

EXAMPLES

Example 1

VP1 Specific IgA Antibody Response of Three Allergic Patients Determined in Different Seasons Blood samples were taken in winter 2006 (win06), spring 2007 (spr), summer 2007 (sum), autumn 2007 (aut) and winter 2007 (win07). Antibody titer was measured by ELISA experiments. ELISA plates (Nunc Maxisorb, Denmark) were coated with 5 µg/ml of VP1 (of rhinovirus strain 89) and incubated with mouse sera diluted 1:50. All experiments were performed in doublets and mean OD were calculated. Bound antibodies were detected with monoclonal mouse anti-mouse human IgA antibodies (BD Pharmingen, San Diego, Calif., USA) diluted 1:1000, and then with rat anti-mouse IgG POX-coupled antibodies (Amersham Bioscience) diluted 1:2000. OD was measured at 405 nm and 490 nm in an ELISA reader (Dynatech, Germany).

Figure 1:
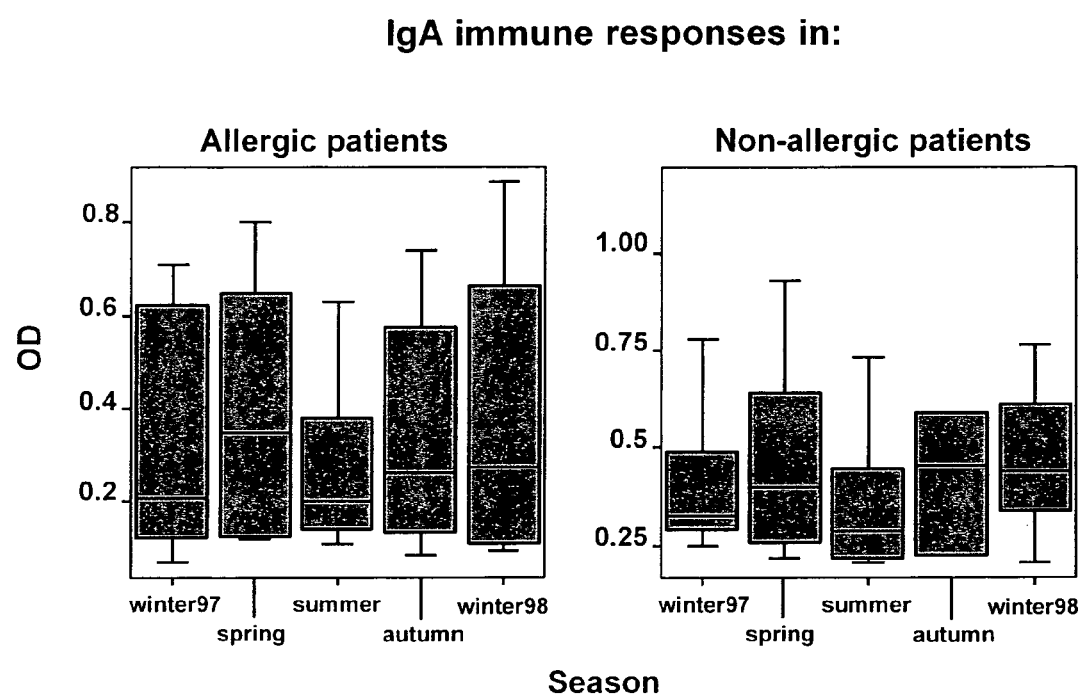

The antibody titer varies from season to season and from patient to patient. This leads to the conclusion that exposure to rhinoviruses can be determined by VP1 (FIG. 1).

Example 2

The Rhinoviral Protein VP1 Induces a Strong IgA Response in a Healthy Volunteer

A healthy volunteer was vaccinated with a formulation containing the whole VP1 molecule, a rhinoviral protein, adsorbed to $Al(OH)_3$ (20 µg/injection). This vaccine was injected subcutaneously in the upper arm of the subject three times (Day 0, 21, 42). Before the first vaccination and at days 65, 79, 91, 98 and 119 blood was taken to analyze the development of the antigen-specific immune response.

Figure 2:
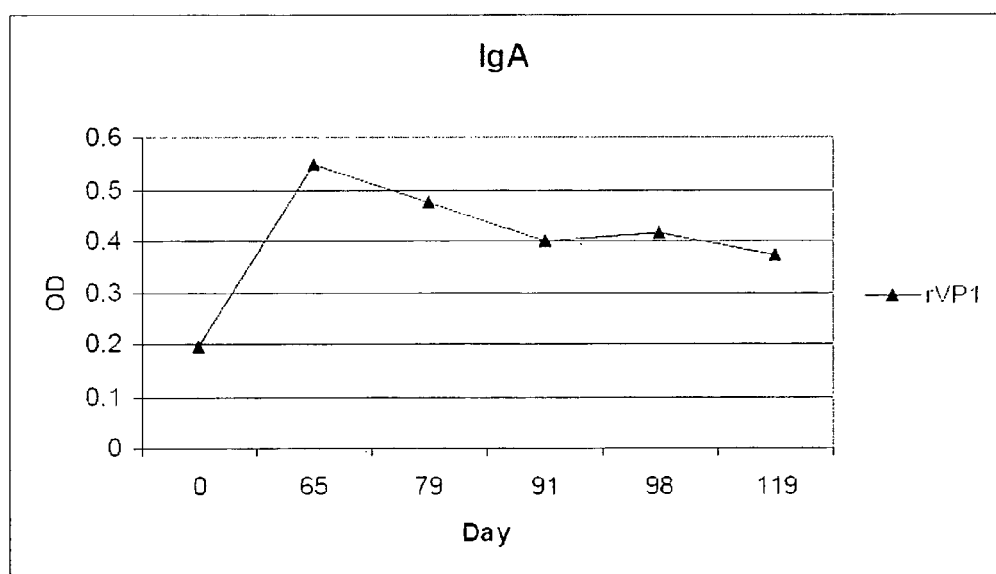

In FIG. 2 the increase of VP1-specific IgA antibodies is demonstrated by ELISA measurements. The x-axis shows the dates of blood sampling and the y-axis the corresponding optical density (OD) values. The maximal amount of VP1-specific IgA antibodies is reached at day 65 (OD=0.551) where, compared to the preimmune serum (day 0), a three-fold increase of VP1-specific IgA antibodies could be measured. After day 65 a slow decline of the IgA level could be detected. But at day 119 the level of VP1-specific IgA antibodies (OD=0.372) was almost twice as much as at day 0 (OD=0.195).

Example 3

VP1-Specific IgA Response of Immunized Mice

In order to determine the VP1-specific IgA response, a group of five mice was immunized subcutaneously with 5 µg of VP1 antigen adsorbed to aluminum hydroxide in three-week intervals. Serum samples were taken from the tail veins on the day before the first immunization (0) and after the second immunization (6w). VP1-specific IgA antibody levels were determined by ELISA. Plates were coated with 5 µg/ml of the VP1 protein and incubated overnight with mouse serum diluted 1:500. Bound IgA was detected with monoclonal rat anti-mouse IgA antibodies diluted 1:1000 and subsequently with goat anti-rat IgG PDX-coupled antibodies diluted 1:2000, respectively. OD was measured at 405 nm and 490 nm. All ELISA experiments were performed in duplicates, and the mean values were calculated.

Although immunization with recombinant VP1 protein induced VP1-specific IgA response in mice, the increase of antibody level after 6 weeks was not significant (FIG. 3).

Example 4

Recombinant Rhinovirus-Derived VP1 for Vaccination Against Common Cold Infections Materials and Methods Construction of expression vectors containing the VP1 cDNA of HRV14 or HRV89

The plasmid containing the whole genome of HRV14 (33) was used as a template for the amplification of 14VP1 (VP1 of HRV14) by PCR. The following primers were used:

```
                                        (SEQ ID NO: 35)
5' CGGAATTCCCATGGGCTTAGGTGATGAATTAGAAGAAGTCATCGTT

GAGA 3'

(SEQ ID NO: 36)
5' GATGGAATTCTCAGTGGTGGTGGTGGTGGTGATAGGATTTAATGTC

AC 3'
```

The restriction sites (NcoI, EcoRI) are underlined. The cDNA coding for the 14VP1 coding region (data base # AY355195) was inserted into the NcoI and EcoRI sites of plasmid pET23d (Novagen, Merck Bioscience, Germany).

Virus stocks of strain 89 were obtained from the collection of the Institute of Virology, Medical University of Vienna. Viral RNA was prepared from cell culture supernatants using the QIAamp viral RNA kit (Qiagen, Germany) and RNase inhibitor (Boehringer GmbH, Germany) was added to a final concentration of 0.01 U/μl. The 89VP1 cDNA (VP1 of HRV89) was amplified by RT-PCR using a SuperScript One Step RT PCR Kit from Invitrogen (USA) using the following primers:

```
                                        (SEQ ID NO: 37)
5' CGGAATTCATTAATATGAACCCAGTTGAAAATTATATAGATAGTGT

ATTA 3'

(SEQ ID NO: 38)
5' CGATTAATTCAGTGGTGGTGGTGGTGGTGGACGTTTGTAACGGTA

A 3'
```

The restriction sites (EcoRI, AseI) are underlined. The cDNA coding for the complete 89VP1 coding region (data base # AY355270) was subcloned into the NdeI and EcoRI site of a pET17b vector (Novagen, Merck Bioscience, Darmstadt, Germany).

Expression and Purification of Recombinant 89VP1 and 14VP1

Recombinant 89VP1 and 14VP1 were expressed in *E. coli* BL21(DE3) (Stratagene, USA). Protein synthesis was induced for 5 hours at 37° C. with 1 mM IPTG and the recombinant proteins were purified from the inclusion body fraction after solubilization in 6 M guanidinium hydrochloride, 100 mM $NaH_2PO_4$, 10 mM Tris, pH 8 using a Ni-NTA affinity matrix (Qiagen, Hilden, Germany). The proteins were washed with washing buffer (100 mM $NaH_2PO_4$, 10 mM Tris-HCl, 8 M urea pH 5.9) and eluted with the same buffer at pH 3.5. Protein preparations were dialyzed against buffers with decreasing urea concentration and finally against $H_2O$dd. Protein purity and concentration were checked by SDS-PAGE and Coomassie blue staining.

Synthetic Peptides and Peptide Conjugates

HRV14-derived peptides (PVP1A, PVP1B and PVP3A) were synthesized on the Applied Biosystems (USA) peptide synthesizer Model 433A using a Fmoc (9 fluorenyl methoxy carbonyl) strategy with HBTU [2-(1H-Benzotriazol-1-yl)1, 1,3,3 tetramethyluronium hexafluorophosphat] activation. The following peptides were purified to >90% purity by preparative HPLC and their identity was verified by mass spectrometry:

```
PVP1A (SEQ ID NO: 39):
VVQAMYVPPGAPNPKEC;
amino acids 147-162 of VP1 (10)

PVP1B (SEQ ID NO: 40):
CRAPRALPYTSIGRTNYPKNTEPVIKKRKGDIKSY;
amino acids 256-289 of VP1 (see WO 2008/057158)

PVP3A (SEQ ID NO: 41):
KLILAYTPPGARGPQDC.
amino acids 126-141 of VP3 (10)
```

Purified peptides were coupled to KLH using an Imject Maleimide Activated Immunogen Conjugation Kit (Pierce, USA) according to the manufacturer's instruction.

Immunization of Mice and Rabbits

Rabbit antibodies against 14VP1, 89VP1, PVP1A, PVP1B or PVP3A were obtained by immunizing rabbits (Charles River, Kisslegg, Germany). Groups of five mice were also immunized subcutaneously with 5 μg of 89VP1 adsorbed to Alum in three-week intervals and bled from the tail veins.

ELISA Experiments

5 μg/ml 89VP1 or 14VP1 were coated to ELISA plates. The mouse sera were diluted 1:500 and the rabbit sera $1:10^3$-$1:10^6$. Antigen-specific IgG1 mouse antibodies were detected with 1:1000 diluted alkaline phosphatase-coupled mouse monoclonal anti-mouse IgG1 antibodies (Pharmingen). Antigen-specific rabbit IgG antibodies were developed with a 1:2000 dilution of donkey anti-rabbit IgG peroxidase-coupled antibodies (Amersham Bioscience). The ODs corresponding to bound antibodies were measured at 405 nm and 490 nm for rabbit antibodies and at 405 nm and 450 nm for mice antibodies in an ELISA reader (Dynatech, Germany).

Reactivity of Anti-VP1 Antibodies with Blotted Rhinovirus Extract and Rhinovirus Cell culture supernatants from HRV-infected HeLa cells were centrifuged in a bench fuge (15.000 rpm, 10 min, 20° C.) to remove insoluble particles. Then, 0.5 ml PEG (40% v/v polyethylene glycol 6000, 2.4% w/v NaCl, pH 7.2) was added to 2 ml of virus-containing supernatant. The solution was incubated at 4° C. over night and then centrifuged at 2,300×rpm for 45 minutes in a bench fuge at RT. The pellet was re-suspended in 100 µl PBS and lysed in 50 µl SDS sample buffer. 10 µl of this HRV14 protein extract and 0.5 µg purified 14VP1 were separated by 12% SDS PAGE and blotted onto nitrocellulose membranes. Identically prepared blots were incubated with 1:500 dilutions of rabbit anti-14VP1 antibodies or the corresponding pre-immune Ig. Bound antibodies were detected with 125I-labelled donkey anti-rabbit IgG and visualized by autoradiography.

For immunogold electron microscopy, 4.2 µl aliquots of the re-suspended viral precipitate were pipetted onto carbon-coated, plasma-cleaned copper grids and air-dried. After 5 minutes, remaining liquid was removed with a piece of filter paper. The grids were then incubated face down (moist chamber at room temperature) in the following buffers: First, PBS containing 1% (w/v) BSA at pH 7.4 and then Tris buffer containing 1% (w/v) BSA at pH 8.2.

Then the following incubation steps were done: (a) 5% (w/v) BSA, 5 min; (b) protein G-purified anti-VP11 g or pre-immune Ig adjusted to an OD280 nm of 0.6, 45 min; (c) 6×PBS buffer, 5 seconds each; (d) 6×Tris buffer, 5 seconds each; (e) goat anti-rabbit Ig coupled to colloidal gold particles with a diameter of 10 nm (Plano, Wetzlar, Germany), diluted 1:20 in Tris buffer, 30 min; (f) 6×Tris buffer, 5 seconds each; (g) 6× distilled water, 5 seconds each. After labelling, negative staining was performed by pipetting a saturated solution of uranyl acetate on the grids. After 1 minute, surplus negative stain was removed with a wet filter paper. The grids were then dried on air and viewed in a Philips EM 410 transmission electron microscope equipped with a high resolution CCD camera. Micrographs were taken at a magnification of 165,000× or 240,000 ×.

HRV Neutralization Test

Rhinovirus stocks and the HRV-sensitive "Ohio" strain of HeLa cells (Stott E J and Tyrrell D A, Arch. Gesamte Virusforsch. 1968; 23:236-244.) were used. HeLa cells were seeded in 24 well plates and grown to approximately 90% confluence. In a first set of experiments, 300 µl aliquots of HRV14 (100 $TCID_{50}$) in medium were incubated for 2 h at 37° C. with 300 µl of rabbit anti-sera (anti-14VP1, anti-PVP1A, anti-PVP1B or PVP3A) or the corresponding pre-immune sera (undiluted or diluted 1:2-1:32) and added to the cells. MEM-Eagle medium (Invitrogen, USA) containing 1% FCS and 40 mM $MgCl_2$ was used as a diluent in the experiments. Plates were incubated at 34° C. in a humidified 5% $CO_2$ atmosphere and viable cells were stained with crystal violet after three days. Cross-neutralization tests were carried out in 96 well plates; HeLa cells were seeded in minimal essential medium (MEM) containing 2% fetal calf serum, 30 mM $MgCl_2$, and 1 mM glutamine (infection medium) and grown over night at 37° C. to about 70% confluency. HRVs (100 $TCID_{50}$ in 100 µl infection medium) were mixed with 100 µl of the respective undiluted antiserum and serial twofold dilutions thereof in the same medium. After incubation for 3 h at 37° C., the cells were overlaid with these solutions and incubation was continued at 34° C. for 3 days. The medium was removed and cells were stained with crystal violet (0.1% in water) for 10 min. After washing with water, the plate was dried, the stain was dissolved in 30 µl 1% SDS under shaking for 1 hour and cell protection was quantified as OD at 560 nm in a plate reader.

Results

Expression and Purification of Recombinant VP1 Proteins from HRV89 and HRV14

Recombinant VP1 of HRV89 (89VP1; FIG. 6A) and HRV14 (14VP1; FIG. 6B) were expressed in E. coli with a His6-tag at their C-termini and purified from solubilized inclusion bodies by single step Nickel affinity chromatography. The purified protein bands appear after Coomassie blue staining at approximately 34 kDa in SDS-PAGE. The recombinant proteins 89VP1 and 14VP1 reacted specifically with the anti-His-tag antibody due to their C-terminal hexa-histidine tag (right lanes; FIG. 6).

89VP1 and 14VP1 induce a VP1-specific immune response in animals. Immunization of rabbits with recombinant 89VP1 and 14VP1 induced VP1-specific IgG responses (FIG. 7A). The immune response to 89VP1 was stronger than that to 14VP1 with antibodies detected up to a serum dilution of $10^{-5}$ after the second and up to a dilution of $10^{-6}$ after the third immunization The 14VP1-specific IgG response was detectable up to a serum dilution of $10^{-3}$ after the second and up to a $10^{-4}$ dilution after the third immunization (FIG. 7A). VP1-specific antibody responses were obtained also in mice immunized with Alum-adsorbed VP1 proteins. IgG1 antibodies specific for 89VP1 were detected already after the first immunization and continued to increase at the second and third immunization (FIG. 7B).

Figure 8A:
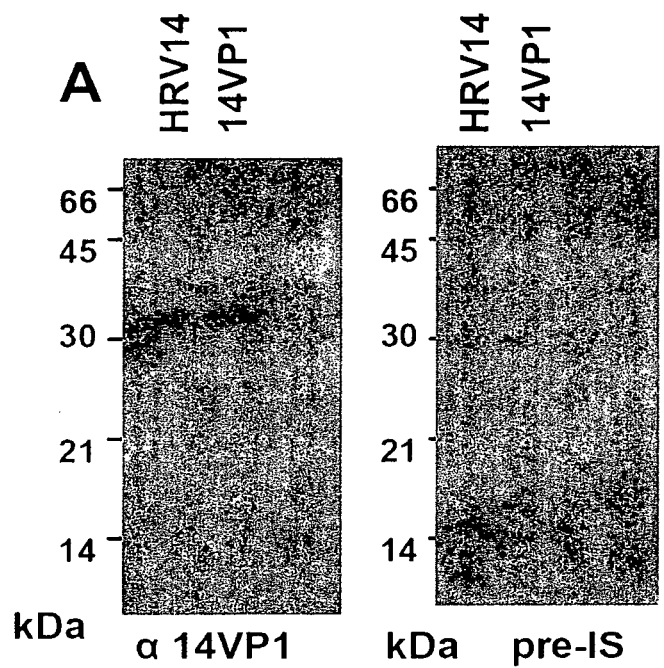
Figure 8B:
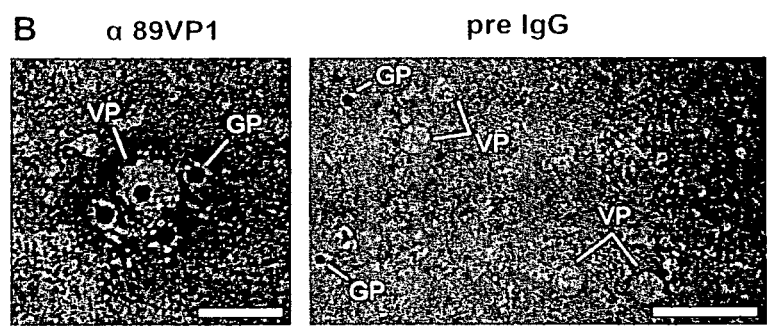

Reactivity of Antibodies Raised Against Recombinant VP1 Proteins Toward Virus-Derived VP1 and Entire Virions The reactivity of antibodies induced by immunization with recombinant VP1 proteins with natural, virus-derived VP1 and whole virus was studied by immunoblotting and electron microscopy, respectively. As a representative example, binding of rabbit anti-14VP1 antibodies and of pre-immune Ig to nitrocellulose-blotted HRV14 proteins and 14VP1 is shown FIG. 8A. Antibodies raised against recombinant 14VP1, but not the pre-immune Ig, reacted with natural and recombinant 14VP1 at approximately 34 kDa (FIG. 8A). Specific binding of anti-89VP1 antibodies to HRV89 was visualized using the immunogold electron microscopy method. When immobilized virions were exposed to anti-89VP1 antibodies and gold-conjugated secondary antibodies approximately 10% of the virus particles appeared coated with one up to five colloidal gold particles (FIG. 8B). No attachment of gold to the virions was found in the control preparations with the pre-immune Ig; few gold particles were present but not associated with virus particles (FIG. 8B; right panel).

Immunization of Rabbits with Recombinant 14VP1 Yields Higher 14VP1- and 89VP1-Specific Antibody Titers than Immunization with KLH-Coupled HRV14-Derived Peptides Antisera were raised against KLH-coupled peptides which have been earlier described as possible vaccine candidates. The anti-peptide antisera contained high titers of peptide-specific antibodies (PVP1A:$10^{-3}$; PVP1B:$10^{-5}$; PVP3A:$10^{-5}$). However, in comparison with antisera raised against recombinant 14VP1, they reacted only weakly with the 14VP1 protein and showed weak cross-reactivity with 89VP1 (FIG. 9). Most remarkably, antiserum raised against recombinant 14VP1 showed a comparable reactivity with 14VP1 and 89VP1. The antiserum against the VP1 protein reacted with both viral proteins at least tenfold more strongly than the peptide antisera (FIG. 9).

14VP1-Specific Antibodies Inhibit HRV Infection of HeLa Cells Better than Peptide-Specific Antibodies Next, it was investigated whether rabbit IgG antibodies raised against recombinant 14VP1 protein can inhibit HRV infection of HeLa cells. Results from one set of cell protection experiments performed with HRV14 are shown in FIG. 10. Presence of 14VP1 antibodies prevented cell death on challenge with HRV14 at 100 $TCID_{50}$ up to a 1:32 dilution of the antiserum.

Also the ability of antibodies raised against complete 14VP1 with antibodies raised against 14VP1-derived peptides for protection of the cells against viral infection was analyzed. Serial dilutions (undiluted or diluted 1:2-1:32) of anti-14VP1, -PVP1A, -PVP1B or -PVP3A antisera were incubated together with HRV14 and added to HeLa cells. The ability to inhibit cell infection of all three anti-peptide antisera was comparable amongst each other. A clear reduction in CPE was seen at a dilution of 1:8 with anti-PVP1A and anti-PVP1B and at a dilution of 1:4 with anti-PVP3A. A similar degree of inhibition of infection (i.e., partial CPE) was obtained with the anti-14VP1 antiserum up to dilution of 1:32. This suggests that the latter antiserum was approximately 8-fold more potent in inhibiting viral infections (Table 1).

TABLE 1

Inhibition of HRV14 infection with antisera raised against 14VP1 and HRV14 derived peptides

|  | undiluted | 1:2 | 1:4 | 1:8 | 1:16 | 1:32 | 1:64 |
|---|---|---|---|---|---|---|---|
| α 14VP1 | +++ | +++ | ++ | ++ | + | + | − |
| α PVP1A | +++ | +++ | + | + | +/− | +/− | − |
| α PVP1B | +++ | +++ | + | + | +/− | +/− | − |
| α PVP3A | +++ | +++ | + | +/− | +/− | +/− | − |

In table 1 the neutralization of infection by antibodies raised against 14VP1 and HRV14 derived peptides is shown. A dilution of anti-14VP1, anti-PVP1A, anti-PVP1B or anti-PVP3A antibodies (undiluted or diluted 1:2-1:32) were preincubated with 100 $TCID_{50}$ HRV14 and added to HeLa cells. Virus neutralizations and cytopathic effects (CPE) observed are indicated: +++: complete neutralization; ++: minimal CPE; +: partial CPE; +/−: almost complete CPE; −: complete CPE.

Antibodies Raised Against Recombinant VP1 Proteins Show Cross-Protection Against Distantly Related HRV Strains.

Figure 11A:
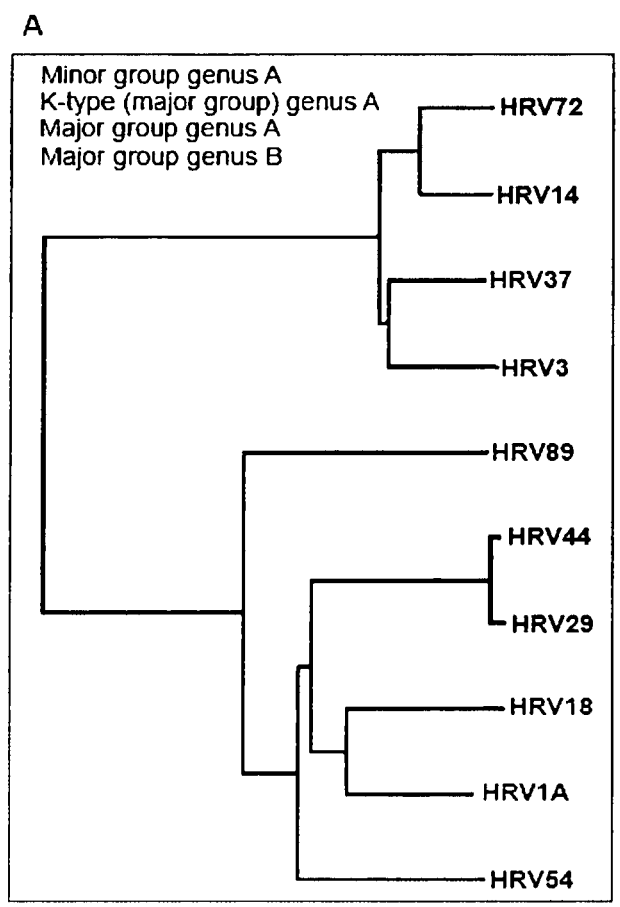
Figure 11B:
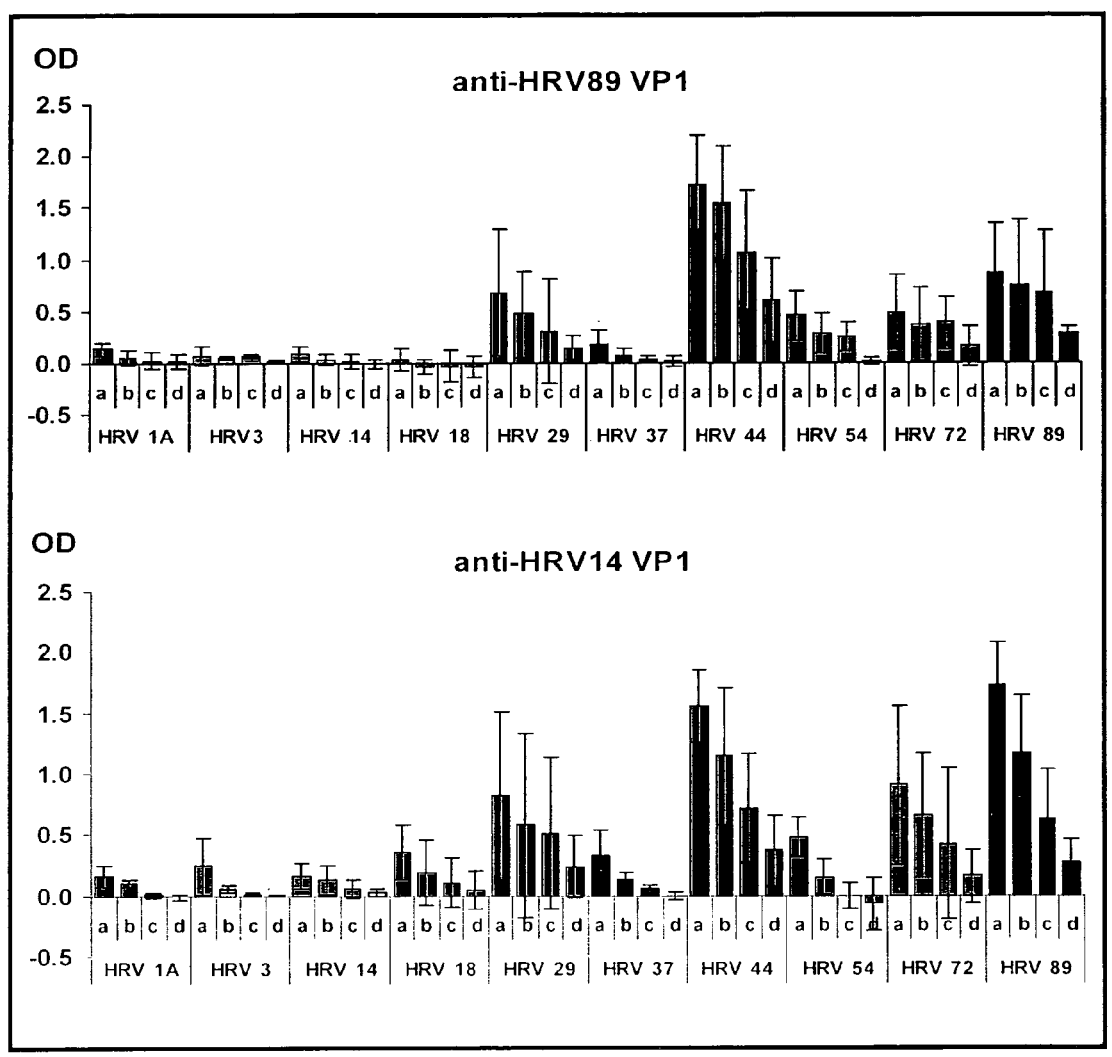

FIG. 11A shows the evolutionary relationship of the rhinovirus types used for the cross-protection experiments. They were selected to belong to different species and different receptor groups: HRV37 and 89 are major group genus A, HRV3, 14 and 72 are major group genus B, HRV1A, 18 and 54 are K-types (i.e., major group HRVs possessing a lysine in the HI loop of VP1) and HRV29 and 44 are minor group genus A. Both, the anti-89VP1 and anti-14VP1 antibodies inhibited infection of HeLa cells by half of the HRV serotypes in a concentration-dependent manner independent of their evolutionary relationship (FIG. 11B). Interestingly, anti-14VP1 antibodies inhibited infection by HRV89 more strongly than anti-89VP1 antibodies whereas anti-89VP1 antibodies only weakly inhibited infection by HRV14 (FIG. 11B). Remarkably, both antisera showed extensive cross-reaction with weakly related HRVs (compare to FIG. 11A).

CONCLUSIONS

A vaccine protecting against rhinovirus infections may be useful to reduce rhinovirus-induced asthma exacerbations. The HRV-derived VP1 capsid protein was investigated as a potential vaccine antigen for several reasons. The work of Rossmann et al., elucidating the crystal structure of HRV14, demonstrates that VP1 is critically involved in HRV binding to its receptor on human epithelial cells. It was found that five copies of VP1 form a depression, called canyon and that the ICAM-1 receptor binds into the central part of this canyon. Furthermore, studies of spontaneous mutations in the viral coat led to the identification of four neutralizing immunogenic (NIm) sites on the surface of HRV14. Additional investigations revealed that antibodies to two of the four antigenic sites which are located on the VP1 protein blocked cellular attachment.

The complete VP1 proteins from HRV89 and HRV14, which belong to the phylogenetically distant species HRV-A and HRV-B, respectively, were expressed in *E. coli* and purified afterwards. Using the ClustalW program for alignment (http://www.ebi.ac.uk/clustalw) only a 45% nucleotide and 41% amino acid identity could be found between 89VP1 and 14VP1. Recombinant 14VP1 and 89VP1 were purified via a C-terminal His-tag by Nickel affinity chromatography in a single step procedure. Immunization of mice and rabbits with recombinant 14VP1 as well as 89VP1 proteins led to the development of VP1-specific antibody responses recognizing natural VP1 from the virus and even intact virus as demonstrated by immunogold electron microscopy.

The antibody responses obtained with the VP1 proteins were compared with those induced by HRV14 VP1- and VP3-derived peptides which had been earlier described as vaccine candidates and with those obtained with a peptide PVP1B located at the C-terminus of the VP1 protein, being part of the ICAM-1 attachment site in HRV14. It was found that the anti-HRV14 VP1 antisera reacted much stronger with VP1 than the anti-peptide antisera and exhibited a higher neutralization titer. The higher neutralization capacity of the antibodies raised against the complete proteins is most likely due to the fact that the antiserum raised against the complete protein recognizes several different epitopes on the VP1 protein and hence may exhibit a higher avidity than the peptide-specific antibodies.

There is a relatively low degree of sequence identity of 45% at the nucleotide and 41% at the amino acid level between 89VP1 and 14VP1. Yet it was found that antibodies raised against the recombinant VP1 proteins from each of these strains inhibited the infection of cultured HeLa cells by a variety of different rhinovirus strains belonging to the major and minor group. The latter finding may be important because it indicates that it may be possible to engineer a broadly cross-protective and effective vaccine against HRV by combining VP1 proteins from a few rhinovirus strains. The efficacy of such a vaccine may be also improved by the addition of other capsid proteins such as VP2, VP3, and/or VP4. The latter one has recently gained attention as it has also elicited cross-protection.

Major advantages of a vaccine based on recombinant rhinovirus capsid proteins are that the vaccine antigens can be easily produced under controlled conditions by large scale recombinant expression in foreign hosts, such as *E. coli* at reasonable costs. A broadly cross-protective HRV vaccine may be especially useful for the vaccination of patients suffering from rhinovirus-induced asthma attacks and may thus reduce asthma exacerbations.

Example 5

Construction of Vectors Containing the VP1, VP2, VP3 and VP4 cDNAs of HRV89

The cDNAs coding for VP1, VP2, VP3 and VP4 of HRV89 were codon optimized for *Escherichia coli* and synthetically synthesized with the addition of six histidine residues at the 3' end. The complete genes were inserted into the NdeI/XhoI fragment of multiple cloning site of pET-27b (ATG Biosynthetics, Germany). The resulting constructs are referred to as vectors p89VP1, p89VP2, p89VP3 and p89VP4 and gene products VP1, VP2, VP3 and VP4. The DNA sequences of VP1, VP2, VP3 and VP4 were confirmed by nucleotide sequencing and double digestion and are shown in FIG. 11.

Example 6

Expression and Purification of Recombinant VP1, VP2, VP3 and VP4

In order to achieve the expression of recombinant capsid proteins, *Escherichia coli* strains BL21 (DE3) were transformed with p89VP1, p89VP2, p89VP3 or p89VP4, respectively, and plated on LB plates containing 100 μg/ml kanamycin. A single colony was used to inoculate 250 ml LB medium containing 100 mg/L kanamycin. This culture was grown to an optical density (600 nm) of 0.6 and the protein expression was induced by adding IPTG to a final concentration of 1 mM. Cells were harvested by centrifugation at 3500 rpm at 40 C for 10 min. Purification was performed with the Qiagen protocol using Ni-NTA. The cell pellet was resuspended under denaturing conditions in 10 ml 6M guanidine hydrochloride for 4 hours. After centrifugation (20 min, 18 000 rpm) the supernatant was incubated with 2 ml Ni-NTA for an additional 2 hours. The suspension was then loaded onto a column, washed twice with 10 ml wash buffer (8 M Urea, 100 mM $NaH_2PO_4$, 10 mM Tris-HCl pH 6.1) and then eluted with 12 ml elution buffer (8 M Urea, 100 mM $NaH_2PO_4$, 10 mM Tris-HCl pH 3.5. Renaturation was achieved after dialysis with decreasing molarity of urea.

Purity and size of the recombinant proteins were analyzed by SDS-PAGE as shown in FIG. 12. Protein bands correlated with the calculated protein sizes of 33.6 kDa for VP1, 30.8 kDa for VP2, 27.8 kDa for VP3 and 8.3 kDa for VP4. Protein sizes were also confirmed by MALDI-TOF analysis.

Example 7

Cloning of Constructs Expressing MBP-VP1 Epitopes Fusion Proteins

The cDNA coding for VP1 was used as a template for the amplification of VP1-derived epitopes by PCR (Table I). The EcoRI and BamHI restriction sites (underlined in Table I) of the pMalc4X vector were used for the insertion of PCR products down-stream of the malE gene of *E. coli*, which encodes maltose-binding protein (MBP), resulting in the expression of MBP fusion proteins (New England BioLabs). The insertion of cDNAs for VP1-derived epitopes was confirmed by nucleotide sequencing and the gene products are referred to as Ep_1, Ep_2 and Ep_3 (FIG. 14A).

TABLE I

Primers used for cloning of PCR fragments (5' to 3').

| Primers | | SEQ ID No. |
|---|---|---|
| Ep_1 forward | CG GAATTC ATG AAC CCA GTT GAA AAT TAT ATA GAT | 1 |
| Ep_1 reverse | CG GGATCC TTA TTT GAA TCC TTT ACC AAT TTT ATC | 2 |

TABLE I-continued

Primers used for cloning of PCR fragments (5' to 3').

| Primers | | SEQ ID No. |
|---|---|---|
| EP_2 forward | CG GAATTC ACA TGG AAG GTT AGT CTT CAA GAA ATG | 3 |
| Ep_2 reverse | CG GGATCC TTA ATA AAA CAT GTA ATA GGC TGA TGC | 4 |
| EP_3 forward | CG GAATTC GAT GGT TAT GAT GGT GAT AGT GCA GCA TC | 5 |
| Ep_3 reverse | CG GGATCC TTA GAC GTT TGT AAC GGT AAA AAC ATC AG | 6 |

Amino Acid Sequences of the N-Terminal Epitope (Epitope 1):

Ep_1a:

(SEQ ID NO: 42)

M N P V E N Y I D S V L N E V L V V P N I Q P S T

S V S S H A A

Ep_1b:

(SEQ ID NO: 43)

P A L D A A E T G H T S S V Q P E D M I E T R Y V

I T D Q T R D E T

Ep_1c:

(SEQ ID NO: 44)

S I E S F L G R S G C I A M I E F N T S S D K T E

H D K I G K G F K

Example 8

Expression and Purification of MBP Fusion Proteins

Recombinant fusion proteins (Ep_1, Ep_2, Ep_3) were expressed in *E. coli* strain BL21 (DE3) as described in Example 6. The purification was performed using MBP's affinity for maltose. The inclusion body fraction was solubilized with 8 M Urea, 100 mM $NaH_2PO_4$, 10 mM Tris-HCl and dialyzed against the Column Buffer (20 mM Tris, 200 mM NaCl, 1 mM EDTA pH=7.4). The clear lysate was loaded onto an equilibrated amylose resin affinity column, washed twice with 60 ml Column Buffer and eluted with 20 ml Column Buffer containing 10 mM Maltose.

Identity of the fusion proteins was confirmed by Western blot analysis using anti-VP1 rabbit antiserum.

Example 9

Detection of VP1-, VP2-, VP3 and VP4-Specific Antibodies in Blood from Patients with Positive HRV-Specific PCR Test Results To investigate the occurrence of VP1-, VP2- VP3- and VP4-specific antibodies in human blood, enzyme linked immunosorbent assay (ELISA) was performed. ELISA plates (Nunc) were coated with 5 µg/ml of recombinant rhinovirus-derived capsid proteins (VP1, VP2, VP3, VP4) and human serum albumin (HSA) was used as a control. The whole blood from 57 HRV-positive patients was diluted 1:50. Bound human IgA, IgM, $IgG_1$ and $IgG_2$ (BD Pharmingen) 1:1000 were detected with sheep anti-mouse peroxidase-coupled (Amersham Bioscience) 1:2000. The optical value (OD 405 nm) is displayed on the y-axis and corresponds to the level of VP1-, VP2- VP3- and VP4-specific antibodies in human blood (FIG. 13). Interesting fine specificities of isotype and subclass specific immune responses were found in HRV-positive patients. Of the four viral capsid proteins, VP1 and VP2 were predominantly recognized by $IgG_1$ and IgA, whereas VP3 and VP4 reacted mainly with IgM. These results show that HRV-infected patients recognize different rhinovirus-derived proteins (VP1, VP2, VP3 and VP4) preferably by $IgG_1$ and IgA antibodies and that those proteins can be used for the diagnosis and monitoring of rhinovirus infections in general and in particular for the identification of patients who suffer from rhinovirus-induced exacerbations of respiratory diseases.

Example 10

Reactivity of Anti-HRV Guinea Pig IgG to VP1-, VP2-, VP3 and VP1-Derived Epitopes In order to evaluate whether recombinant capsid proteins of HRV89 and VP1-derived epitopes cross-react with a variety of different rhinovirus strains, ELISA plates were coated with 5 µg/ml of each antigen. Guinea pig sera raised against twenty seven rhinovirus strains, belonging to different species and different receptor groups, were diluted 1:1000. Antigen-specific IgG were detected with 1:2000 diluted goat anti-guinea pig peroxidase-coupled antibodies (Jackson ImmunoResearch). The OD's corresponding to bound antibodies were measured at 405 nm and 490 nm in an ELISA reader. Anti-HRV89 serum and anti-guinea pig serum were used as controls (Sigma) (FIG. 15).

A high anti-VP1 IgG titer could be detected in sera raised against almost a half of the strains tested and an enhanced anti-Ep_1 IgG titer was found in sera with a high anti-VP1 antibody level. These findings have important implications for the diagnosis of HRV infections, especially in the context of airway diseases, because they show that VP1 and its epitopes located mostly within the N-terminus of the entire protein are recognized not only by anti-guinea pig sera raised against the major group but also by sera raised against the minor group rhinoviruses.

Example 11

Comparison of HRV-Specific Antibody Responses with Various Patients' Clinical Data In order to investigate whether it is possible to find a correlation between VP1-, VP2-, VP3- and VP4-specifc antibody responses and different clinical manifestations, a single variant analysis using the 'Mann-Whitney' test was used (p values <0.05 were considered positive). The following clinical data were considered:

fever
convulsions
sex
croup
HRV PCR and Influenza PCR
Time of gestation
Rhinitis
Cough
Exposure to smoke
Wheeze
Whistle
Administration of bronchodilators
Asthma
Bronchiolitis
A significant statistical connection was found among:
VP1-specific IgM and convulsions
VP4-specific IgG1 and croup
VP1-, VP2-, VP3- and VP4-specific IgA and HRV/Influenza double positive PCR
VP3- and VP4-specific IgG1, VP3-specific IgM and bronchiolitis
VP4-specific IgG1 and VP1- and VP2-specific IgA and asthma
VP1-specific IgG2 and VP3- and VP4-specific IgA and exposure to smoke Next, a multi-variant analysis was performed. Basically, in this test clinical data were grouped with various ways and then compared with the antibody values like in the single variant tests. The only 2 groups that gave a correct hypothesis (p <0.05) were the following:
Group 1:
asthma/bronchiolitis/convulsion/croup
Group 2:
Asthma, bronchiolitis, viral positive PCR, convulsion, croup Group 2 produced various statistical significant results. These were mostly affected by the presence of the viral double infection factor which seemed to be very important throughout the single and multi-variant analyses. For VP2-specific IgM there was a connection between viral double infection and convulsion, while for VP1-specific IgA a relationship between viral double infection and asthma was found.

Furthermore, it was found that antibody levels might be used as a biological marker for the HRV/Influenza double infection. FIG. 20 shows the ROC curve for the Ig values in patients with double infection. There is not only a statistical significance in the hypothesis (Ig values as biological marker) but also the possibility to establish threshold values for VP1-, VP2- VP3- and VP4-specific IgA.

Based on these results, it is assumed that it will be possible to develop serological tests for the diagnosis of rhinovirus infections and their association with respiratory illnesses.

Example 12

Mapping the Antigenic Determinants of the Major Capsid Protein VP1

Recombinant VP1 of the HRV89 has been found to be the most immunologically important surface protein in human blood samples (FIG. 13). Therefore, three VP1-derived fragments were amplified by PCR using cDNA coding for VP1 as a template and fused to the C-terminus of the Maltose Binding Protein (MBP). The MBP-fusion proteins containing VP1-derived fragments, each comprising approximately 100 amino acids (FIG. 14A), were expressed in E. coli. The fusion proteins were purified by affinity chromatography and analyzed by SDS-PAGE. The integrity of the fusion proteins was confirmed by immunoblotting with anti-MBP and anti-VP1 rabbit antiserum (data not shown). The purified MBP-fusion proteins were used to asses whether epitope-specific antibodies can be found in human blood and which antibody subclasses can be identified. As shown in FIG. 14B, the major $IgG_1$ epitopes were located at the N-terminal recombinant VP1 fragment comprising the first 100 amino acids of the entire protein. Enhanced reactivity was detected for IgA, while no reactivity was found for IgM, $IgG_2$, $IgG_3$ and $IgG_4$ (FIG. 14B). To further analyze the epitope specificity, different peptides derived from the N-terminus of the VP1, each comprising approximately 30 (FIG. 19A) or 20 (FIG. 19B) amino acids were synthesized. The peptides were then used to investigate the occurrence of antibody responses in HRV-infected patients. In both experiments, the major $IgG_1$ epitopes were located within the first 32 (FIG. 19A) or even 15 (FIG. 19B) amino acids of the VP1 protein.

The amino acid sequences referred to in this example and in FIG. 19 are the following Amino Acid Residues 1 to 100 of VP1 HRV89 (Referred to as P_1)

```
                                       (SEQ ID NO: 7)
M N P V E N Y I D S V L N E V L V V P N I Q P S T

S V S S H A A P A L D A A E T G H T S S V Q P E D

M I E T R Y V I T D Q T R D E T S I E S F L G R S

G C I A M I E F N I S S D K T E H D K I G K G F K
```

P_1 Derived Peptides of VP1 89HRV:

```
1. P1A, 31 aa
                                      (SEQ ID NO: 48)
N P V E N Y I D S V L N E V L V V P N I Q P S T

S V S S H A A

2. P1B, 34 aa
                                      (SEQ ID NO: 51)
P A L D A A E T G H T S S V Q P E D M I E T R Y

V I T D Q T R D E T

3. P1C, 34 aa
                                      (SEQ ID NO: 52)
S I E S F L G R S G C I A M I E F N I S S D K T

E H D K I G K G F K
```

P1A Derived Peptides of VP1 89HRV

```
1. P1a
                                      (SEQ ID NO: 49)
N P V E N Y I D S V L N E V L V V P N I Q

2. P1b
                                      (SEQID NO: 53)
V V P N I Q P S T S V S S H A A P A L D
```

-continued

```
3. P1c
                                      (SEQ ID NO: 54)
A P A L D A A E T G H T S S V Q P E D M

4. P1d
                                      (SEQID NO: 55)
Q P E D M I E T R Y V I T D Q T R D E T

5. P1e
                                      (SEQID NO: 56)
T R D E T S I E S F L G R S G C I A M I

6. P1f
                                      (SEQID NO: 57)
C I A M I E F N T S S D K T E H D K I G

7. P1g
                                      (SEQID NO: 58)
H D K I G K G F K T W K I S L Q E M A Q
```

Example 13

Antibodies Raised Against Recombinant Capsid Proteins Inhibit HRV Infection of HeLa Cells It was investigated whether rabbit IgG antibodies raised against recombinant VP1, VP2, VP3 and VP4 capsid proteins can inhibit HRV infection of HeLa cells. Results from one set of experiments are shown in FIG. 19. Serial dilutions (1:2 to 1:128) of anti-VP1, anti-VP2, anti-VP3 anti-VP4 were incubated together with HRV89 at 10 $TCID_{50}$, 100 $TCID_{50}$ and 1000 $TCID_{50}$ and added to the HeLa cells. All four anti-sera showed the ability to inhibit cell infection when challenged with HRV89 at 10 $TCID_{50}$. When higher amounts of virus were used, a significant reduction of CPE was obtained with anti-VP1, anti-VP2 and anti-VP4.

This suggests that not only antibodies raised against VP1, but also VP2 and VP4, are able to protect HeLa cells from HRV infection (FIG. 20). Therefore, it may be assumed that a vaccine consisting of a mixture of different recombinant capsid proteins might show more extensive cross-reaction with other HRV strains.

Example 14

Reactivity of Rabbit Anti-89VP1 and Anti-14VP1 Antibodies with 14VP1, 89VP1 and Three Recombinant 89VP1 Fragments In order to confirm the specificity of the rabbit anti-HRV14VP1 and anti-HRV89VP1 anti-sera an ELISA experiment using purified recombinant VP1 proteins from HRV14 and 89 as well as three recombinant fragments of HRV89-derived VP1 was performed. It has been found that anti-HRV14VP1 antibodies cross-reacted with VP1 and three VP1 fragments spanning aa 1-100 (see example 12), aa 101-200 and aa 201-293 but had a much lower titer than the anti-HRV89VP1 antibodies. In this context, it is noteworthy, that the anti-VP1 anti-sera obtained by immunization with VP1 from HRV14 and HRV89 differentially reacted with these recombinant fragments of 89VP1. It thus appears that this latter anti-serum contains IgGs reacting with many more epitopes than the anti-serum raised against 14VP1. Furthermore, it confirms the assumption that using VP1-derived fragments it is possible to detect antibodies directed against distantly related rhinovirus species.

The invention claimed is:

1. A method for diagnosing in vitro a rhinovirus infection caused by at least one of rhinovirus strains 1B, 29, 47, 62, 79 and 89 in a mammal comprising the steps of:
   providing an antibody comprising sample of a mammal,
   contacting said sample with at least one peptide consisting of a minimum of 15 and a maximum of 50 amino acid residues comprising amino acid residues 1 to 15 of a rhinovirus VP1 capsid protein of rhinovirus strain 89, and
   diagnosing a rhinovirus infection when the binding of antibodies to said at least one peptide is detected.

2. The method according to claim 1, characterized in that the sample is a blood sample, a sputum sample, neural lavage fluid sample or tear sample.

3. The method according to claim 1, characterised in that the amino acid residues 1 to 15 of the rhinovirus capsid protein have amino acid sequence NPVENYIDSVLNEVL (amino acids 1-15 of SEQ ID NO:49).

4. The method according to claim 1, characterised in that the at least one peptide is selected from the group consisting of NPVENYIDSVLNEVLVVPNIQPSTSVSSHAA (SEQ ID NO:48) and NPVENYIDSVLNEVLVVPNIQ (SEQ ID NO:49).

5. The method according to claim 2, wherein the blood sample is serum or plasma.

* * * * *

SEQUENCE LISTING

```
<160> NUMBER OF SEQ ID NOS: 59

<210> SEQ ID NO 1
<211> LENGTH: 35
<212> TYPE: DNA
<213> ORGANISM: Artificial Sequence
<220> FEATURE:
<223> OTHER INFORMATION: Primer

<400> SEQUENCE: 1
cggaattcat gaacccagtt gaaaattata tagat                              35

<210> SEQ ID NO 2
<211> LENGTH: 35
<212> TYPE: DNA
<213> ORGANISM: Artificial Sequence
<220> FEATURE:
<223> OTHER INFORMATION: Primer

<400> SEQUENCE: 2
cgggatcctt atttgaatcc tttaccaatt ttatc                              35

<210> SEQ ID NO 3
<211> LENGTH: 35
<212> TYPE: DNA
<213> ORGANISM: Artificial Sequence
<220> FEATURE:
<223> OTHER INFORMATION: Primer

<400> SEQUENCE: 3
cggaattcac atggaaggtt agtcttcaag aaatg                              35

<210> SEQ ID NO 4
<211> LENGTH: 35
<212> TYPE: DNA
<213> ORGANISM: Artificial Sequence
<220> FEATURE:
<223> OTHER INFORMATION: Primer

<400> SEQUENCE: 4
cgggatcctt aataaaacat gtaataggct gatgc                              35

<210> SEQ ID NO 5
<211> LENGTH: 37
<212> TYPE: DNA
<213> ORGANISM: Artificial Sequence
<220> FEATURE:
<223> OTHER INFORMATION: Primer

<400> SEQUENCE: 5
cggaattcga tggttatgat ggtgatagtg cagcatc                            37

<210> SEQ ID NO 6
<211> LENGTH: 37
<212> TYPE: DNA
<213> ORGANISM: Artificial Sequence
<220> FEATURE:
<223> OTHER INFORMATION: Primer

<400> SEQUENCE: 6
cgggatcctt agacgtttgt aacggtaaaa acatcag                            37

<210> SEQ ID NO 7
<211> LENGTH: 100
<212> TYPE: PRT
<213> ORGANISM: Artificial Sequence
```

<220> FEATURE:
<223> OTHER INFORMATION: amino acid residues 1 to 100 of VP1 of human
      rhinovirus 89

<400> SEQUENCE: 7

Met Asn Pro Val Glu Asn Tyr Ile Asp Ser Val Leu Asn Glu Val Leu
1               5                   10                  15

Val Val Pro Asn Ile Gln Pro Ser Thr Ser Val Ser Ser His Ala Ala
            20                  25                  30

Pro Ala Leu Asp Ala Ala Glu Thr Gly His Thr Ser Ser Val Gln Pro
        35                  40                  45

Glu Asp Met Ile Glu Thr Arg Tyr Val Ile Thr Asp Gln Thr Arg Asp
50                  55                  60

Glu Thr Ser Ile Glu Ser Phe Leu Gly Arg Ser Gly Cys Ile Ala Met
65                  70                  75                  80

Ile Glu Phe Asn Thr Ser Ser Asp Lys Thr Glu His Asp Lys Ile Gly
                85                  90                  95

Lys Gly Phe Lys
            100

<210> SEQ ID NO 8
<211> LENGTH: 287
<212> TYPE: PRT
<213> ORGANISM: Human rhinovirus 1A

<400> SEQUENCE: 8

Asn Pro Val Glu Asn Tyr Ile Asp Glu Val Leu Asn Glu Val Leu Val
1               5                   10                  15

Val Pro Asn Ile Lys Glu Ser His His Thr Thr Ser Asn Ser Ala Pro
            20                  25                  30

Leu Leu Asp Ala Ala Glu Thr Gly His Thr Ser Asn Val Gln Pro Glu
        35                  40                  45

Asp Ala Ile Glu Thr Arg Tyr Val Ile Thr Ser Gln Thr Arg Asp Glu
50                  55                  60

Met Ser Ile Glu Ser Phe Leu Gly Arg Ser Gly Cys Val His Ile Ser
65                  70                  75                  80

Arg Ile Lys Val Asp Tyr Thr Asp Tyr Asn Gly Gln Asp Ile Asn Phe
                85                  90                  95

Thr Lys Trp Lys Ile Thr Leu Gln Glu Met Ala Gln Ile Arg Arg Lys
            100                 105                 110

Phe Glu Leu Phe Thr Tyr Val Arg Phe Asp Ser Glu Ile Thr Leu Val
        115                 120                 125

Pro Cys Ile Ala Gly Arg Gly Asp Asp Ile Gly His Ile Val Met Gln
130                 135                 140

Tyr Met Tyr Val Pro Pro Gly Ala Pro Ile Pro Ser Lys Arg Asn Asp
145                 150                 155                 160

Phe Ser Trp Gln Ser Gly Thr Asn Met Ser Ile Phe Trp Gln His Gly
                165                 170                 175

Gln Pro Phe Pro Arg Phe Ser Leu Pro Phe Leu Ser Ile Ala Ser Ala
            180                 185                 190

Tyr Tyr Met Phe Tyr Asp Gly Tyr Asp Gly Asp Asn Thr Ser Ser Lys
        195                 200                 205

Tyr Gly Ser Val Val Thr Asn Asp Met Gly Thr Ile Cys Ser Arg Ile
210                 215                 220

Val Thr Glu Lys Gln Lys His Ser Val Val Ile Thr Thr His Ile Tyr
225                 230                 235                 240

His Lys Ala Lys His Thr Lys Ala Trp Cys Pro Arg Pro Arg Ala
                245                 250                 255

Val Pro Tyr Thr His Ser His Val Thr Asn Tyr Met Pro Glu Thr Gly
            260                 265                 270

Asp Val Thr Thr Ala Ile Val Arg Arg Asn Thr Ile Thr Thr Ala
        275                 280                 285

<210> SEQ ID NO 9
<211> LENGTH: 287
<212> TYPE: PRT
<213> ORGANISM: Human rhinovirus 1B

<400> SEQUENCE: 9

Asn Pro Val Glu Asn Tyr Ile Asp Glu Val Leu Asn Glu Val Leu Val
1               5                   10                  15

Val Pro Asn Ile Lys Glu Ser His His Thr Thr Ser Asn Ser Ala Pro
            20                  25                  30

Leu Leu Asp Ala Ala Glu Thr Gly His Thr Ser Asn Val Gln Pro Glu
        35                  40                  45

Asp Ala Ile Glu Thr Arg Tyr Val Met Thr Ser Gln Thr Arg Asp Glu
    50                  55                  60

Met Ser Ile Glu Ser Phe Leu Gly Arg Ser Gly Cys Val His Ile Ser
65                  70                  75                  80

Arg Ile Lys Val Asp Tyr Asn Asp Tyr Asn Gly Val Asn Lys Asn Phe
                85                  90                  95

Thr Thr Trp Lys Ile Thr Leu Gln Glu Met Ala Gln Ile Arg Arg Lys
            100                 105                 110

Phe Glu Leu Phe Thr Tyr Val Arg Phe Asp Ser Glu Val Thr Leu Val
        115                 120                 125

Pro Cys Ile Ala Gly Arg Gly Asp Asp Ile Gly His Val Val Met Gln
130                 135                 140

Tyr Met Tyr Val Pro Pro Gly Ala Pro Ile Pro Lys Thr Arg Asn Asp
145                 150                 155                 160

Phe Ser Trp Gln Ser Gly Thr Asn Met Ser Ile Phe Trp Gln His Gly
                165                 170                 175

Gln Pro Phe Pro Arg Phe Ser Leu Pro Phe Leu Ser Ile Ala Ser Ala
            180                 185                 190

Tyr Tyr Met Phe Tyr Asp Gly Tyr Asp Gly Asp Asn Ser Ser Ser Lys
        195                 200                 205

Tyr Gly Ser Ile Val Thr Asn Asp Met Gly Thr Ile Cys Ser Arg Ile
    210                 215                 220

Val Thr Glu Lys Gln Glu His Pro Val Val Ile Thr Thr His Ile Tyr
225                 230                 235                 240

His Lys Ala Lys His Thr Lys Ala Trp Cys Pro Arg Pro Pro Arg Ala
                245                 250                 255

Val Pro Tyr Thr His Ser Arg Val Thr Asn Tyr Val Pro Lys Thr Gly
            260                 265                 270

Asp Val Thr Thr Ala Ile Val Pro Arg Ala Ser Met Lys Thr Val
        275                 280                 285

<210> SEQ ID NO 10
<211> LENGTH: 283
<212> TYPE: PRT
<213> ORGANISM: Human rhinovirus 2

<400> SEQUENCE: 10

Asn Pro Val Glu Asn Tyr Ile Asp Glu Val Leu Asn Glu Val Leu Val
1               5                   10                  15

Val Pro Asn Ile Asn Ser Ser Asn Pro Thr Thr Ser Asn Ser Ala Pro
            20                  25                  30

Ala Leu Asp Ala Ala Glu Thr Gly His Thr Ser Ser Val Gln Pro Glu
        35                  40                  45

Asp Val Ile Glu Thr Arg Tyr Val Gln Thr Ser Gln Thr Arg Asp Glu
    50                  55                  60

Met Ser Leu Glu Ser Phe Leu Gly Arg Ser Gly Cys Ile His Glu Ser
65                  70                  75                  80

Lys Leu Glu Val Thr Leu Ala Asn Tyr Asn Lys Glu Asn Phe Thr Val
                85                  90                  95

Trp Ala Ile Asn Ile Gln Glu Met Ala Gln Ile Arg Arg Lys Phe Glu
            100                 105                 110

Leu Phe Thr Tyr Thr Arg Phe Asp Ser Glu Ile Thr Leu Val Pro Cys
        115                 120                 125

Ile Ser Ala Leu Ser Gln Asp Ile Gly His Ile Thr Met Gln Tyr Met
    130                 135                 140

Tyr Val Pro Pro Gly Ala Pro Val Pro Asn Ser Arg Asp Asp Tyr Ala
145                 150                 155                 160

Trp Gln Ser Gly Thr Asn Ala Ser Val Phe Trp Gln His Gly Gln Ala
                165                 170                 175

Tyr Pro Arg Phe Ser Leu Pro Phe Leu Ser Val Ala Ser Ala Tyr Tyr
            180                 185                 190

Met Phe Tyr Asp Gly Tyr Asp Glu Gln Asp Gln Asn Tyr Gly Thr Ala
        195                 200                 205

Ser Thr Asn Asn Met Gly Ser Leu Cys Ser Arg Ile Val Thr Glu Lys
    210                 215                 220

His Ile His Lys Val His Ile Met Thr Arg Ile Tyr His Lys Ala Lys
225                 230                 235                 240

His Val Lys Ala Trp Cys Pro Arg Pro Pro Arg Ala Leu Glu Tyr Thr
                245                 250                 255

Arg Ala His Arg Thr Asn Phe Lys Ile Glu Asp Arg Ser Ile Gln Thr
            260                 265                 270

Ala Ile Val Thr Arg Pro Ile Ile Thr Thr Ala
        275                 280

<210> SEQ ID NO 11
<211> LENGTH: 288
<212> TYPE: PRT
<213> ORGANISM: Human rhinovirus 3

<400> SEQUENCE: 11

Gly Leu Ser Asp Glu Leu Glu Glu Val Ile Val Glu Lys Thr Lys Gln
1               5                   10                  15

Thr Leu Ala Ser Val Ser Ser Gly Pro Lys His Thr Gln Ser Val Pro
            20                  25                  30

Ala Leu Thr Ala Asn Glu Thr Gly Ala Thr Leu Pro Thr Arg Pro Ser
        35                  40                  45

Asp Asn Val Glu Thr Arg Thr Thr Tyr Met His Phe Asn Gly Ser Glu
    50                  55                  60

Thr Asp Val Glu Ser Phe Leu Gly Arg Ala Ala Cys Val His Val Thr
65                  70                  75                  80

```
Glu Ile Lys Asn Lys Asn Ala Ala Gly Leu Asp Asn His Arg Lys Glu
                85                  90                  95

Gly Leu Phe Asn Asp Trp Lys Ile Asn Leu Ser Ser Leu Val Gln Leu
            100                 105                 110

Arg Lys Lys Leu Glu Leu Phe Thr Tyr Val Arg Phe Asp Ser Glu Tyr
        115                 120                 125

Thr Ile Leu Ala Thr Ala Ser Gln Pro Glu Ala Ser Ser Tyr Ser Ser
    130                 135                 140

Asn Leu Thr Val Gln Ala Met Tyr Val Pro Gly Ala Pro Asn Pro
145                 150                 155                 160

Lys Glu Trp Asp Asp Tyr Thr Trp Gln Ser Ala Ser Asn Pro Ser Val
                165                 170                 175

Phe Phe Lys Val Gly Glu Thr Ser Arg Phe Ser Val Pro Phe Val Gly
            180                 185                 190

Ile Ala Ser Ala Tyr Asn Cys Phe Tyr Asp Gly Tyr Ser His Asp Asp
        195                 200                 205

Pro Asp Thr Pro Tyr Gly Ile Thr Val Leu Asn His Met Gly Ser Met
    210                 215                 220

Ala Phe Arg Val Val Asn Glu His Asp Val His Thr Thr Ile Val Lys
225                 230                 235                 240

Ile Arg Val Tyr His Arg Ala Lys His Val Glu Ala Trp Ile Pro Arg
                245                 250                 255

Ala Pro Arg Ala Leu Pro Tyr Val Ser Ile Gly Arg Thr Asn Tyr Pro
            260                 265                 270

Arg Asp Ser Lys Thr Ile Ile Lys Lys Arg Thr Asn Ile Lys Thr Tyr
        275                 280                 285

<210> SEQ ID NO 12
<211> LENGTH: 289
<212> TYPE: PRT
<213> ORGANISM: Human rhinovirus 6

<400> SEQUENCE: 12

Gly Leu Gly Asp Glu Leu Glu Glu Val Ile Val Glu Lys Thr Lys Gln
1               5                   10                  15

Thr Leu Ala Ser Val Ser Ser Gly Pro Lys His Thr Gln Ser Val Pro
                20                  25                  30

Ile Leu Thr Ala Asn Glu Thr Gly Ala Thr Met Pro Thr Asn Pro Ser
            35                  40                  45

Asp Asn Val Glu Thr Arg Thr Thr Tyr Met His Phe Asn Gly Ser Glu
        50                  55                  60

Thr Asp Val Glu Ser Phe Leu Gly Arg Ala Ala Cys Val His Ile Thr
65                  70                  75                  80

Glu Ile Glu Asn Lys Asn Pro Ala Asp Ile Gln Asn Gln Lys Glu Glu
                85                  90                  95

Lys Leu Phe Asn Asp Trp Lys Ile Asn Phe Ser Ser Leu Val Gln Leu
            100                 105                 110

Arg Lys Lys Leu Glu Leu Phe Thr Tyr Ile Arg Phe Asp Ser Glu Tyr
        115                 120                 125

Thr Ile Leu Ala Thr Ala Ser Gln Pro Lys Ser Asn Tyr Ala Ser Asn
    130                 135                 140

Leu Val Val Gln Ala Met Tyr Val Pro Pro Gly Ala Pro Asn Pro Glu
145                 150                 155                 160

Lys Trp Asp Asp Phe Thr Trp Gln Ser Ala Ser Asn Pro Ser Val Phe
                165                 170                 175
```

```
Phe Lys Val Gly Asp Thr Ser Arg Phe Ser Val Pro Phe Val Gly Leu
            180                 185                 190

Ala Ser Ala Tyr Asn Cys Phe Tyr Asp Gly Tyr Ser His Asp Asp Lys
        195                 200                 205

Asp Thr Pro Tyr Gly Ile Thr Val Leu Asn His Met Gly Ser Ile Ala
        210                 215                 220

Phe Arg Val Val Asn Glu His Asp Ala His Lys Thr Leu Val Lys Ile
225                 230                 235                 240

Arg Val Tyr His Arg Ala Lys His Val Glu Ala Trp Ile Pro Arg Ala
                245                 250                 255

Pro Arg Ala Leu Pro Tyr Glu Thr Ile Gly Arg Thr Asn Tyr Pro Lys
            260                 265                 270

Lys Asn Lys Ile Val Pro Val Ile Lys Lys Arg Glu Asn Ile Thr Thr
        275                 280                 285

Tyr

<210> SEQ ID NO 13
<211> LENGTH: 289
<212> TYPE: PRT
<213> ORGANISM: Human rhinovirus 14

<400> SEQUENCE: 13

Gly Leu Gly Asp Glu Leu Glu Glu Val Ile Val Glu Lys Thr Lys Gln
1               5                   10                  15

Thr Val Ala Ser Ile Ser Ser Gly Pro Lys His Thr Gln Lys Val Pro
            20                  25                  30

Ile Leu Thr Ala Asn Glu Thr Gly Ala Thr Met Pro Val Leu Pro Ser
        35                  40                  45

Asp Ser Ile Glu Thr Arg Thr Thr Tyr Met His Phe Asn Gly Ser Glu
    50                  55                  60

Thr Asp Val Glu Cys Phe Leu Gly Arg Ala Ala Cys Val His Val Thr
65                  70                  75                  80

Glu Ile Gln Asn Lys Asp Ala Thr Gly Ile Asp Asn His Arg Glu Ala
                85                  90                  95

Lys Leu Phe Asn Asp Trp Lys Ile Asn Leu Ser Ser Leu Val Gln Leu
            100                 105                 110

Arg Lys Lys Leu Glu Leu Phe Thr Tyr Val Arg Phe Asp Ser Glu Tyr
        115                 120                 125

Thr Ile Leu Ala Thr Ala Ser Gln Pro Asp Ser Ala Asn Tyr Ser Ser
    130                 135                 140

Asn Leu Val Val Gln Ala Met Tyr Val Pro Pro Gly Ala Pro Asn Pro
145                 150                 155                 160

Lys Glu Trp Asp Asp Tyr Thr Trp Gln Ser Ala Ser Asn Pro Ser Val
                165                 170                 175

Phe Phe Lys Val Gly Asp Thr Ser Arg Phe Ser Val Pro Tyr Val Gly
            180                 185                 190

Leu Ala Ser Ala Tyr Asn Cys Phe Tyr Asp Gly Tyr Ser His Asp Asp
        195                 200                 205

Ala Glu Thr Gln Tyr Gly Ile Thr Val Leu Asn His Met Gly Ser Met
    210                 215                 220

Ala Phe Arg Ile Val Asn Glu His Asp Glu His Lys Thr Leu Val Lys
225                 230                 235                 240

Ile Arg Val Tyr His Arg Ala Lys His Val Glu Ala Trp Ile Pro Arg
                245                 250                 255
```

-continued

Ala Pro Arg Ala Leu Pro Tyr Thr Ser Ile Gly Arg Thr Asn Tyr Pro
        260                 265                 270

Lys Asn Thr Glu Pro Val Ile Lys Lys Arg Lys Gly Asp Ile Lys Ser
        275                 280                 285

Tyr

<210> SEQ ID NO 14
<211> LENGTH: 290
<212> TYPE: PRT
<213> ORGANISM: Human rhinovirus 15

<400> SEQUENCE: 14

Asn Pro Val Glu Asn Tyr Ile Asp Glu Val Leu Asn Glu Val Leu Val
1               5                   10                  15

Val Pro Asn Ile Lys Glu Ser His Ser Ser Thr Ser Asn Ser Ala Pro
            20                  25                  30

Ala Leu Asp Ala Ala Glu Thr Gly His Thr Ser Ser Val Gln Pro Glu
        35                  40                  45

Asp Met Ile Glu Thr Arg Tyr Val Gln Thr Ser Gln Thr Arg Asp Glu
    50                  55                  60

Met Ser Ile Glu Ser Phe Leu Gly Arg Ser Gly Cys Val His Ile Ser
65                  70                  75                  80

Asp Leu Lys Ile His Tyr Glu Asp Tyr Asn Lys Asp Gly Lys Asn Phe
                85                  90                  95

Thr Lys Trp Gln Ile Asn Leu Lys Glu Met Ala Gln Ile Arg Arg Lys
            100                 105                 110

Phe Glu Leu Phe Thr Tyr Val Arg Phe Asp Ser Glu Ile Thr Leu Val
        115                 120                 125

Pro Cys Ile Ala Ala Lys Ser Asp Asn Ile Gly His Val Val Met Gln
    130                 135                 140

Tyr Met Tyr Val Pro Pro Gly Ala Pro Leu Pro Asn Lys Arg Asn Asp
145                 150                 155                 160

Tyr Thr Trp Gln Ser Gly Thr Asn Ala Ser Val Phe Trp Gln His Gly
                165                 170                 175

Gln Pro Tyr Pro Arg Phe Ser Leu Pro Phe Leu Ser Ile Ala Ser Ala
            180                 185                 190

Tyr Tyr Met Phe Tyr Asp Gly Tyr Asp Gly Asp Ser Thr Glu Ser His
        195                 200                 205

Tyr Gly Thr Val Val Thr Asn Asp Met Gly Thr Leu Cys Ser Arg Ile
    210                 215                 220

Val Thr Glu Glu His Gly Thr Arg Val Glu Ile Thr Thr Arg Val Tyr
225                 230                 235                 240

His Lys Ala Lys His Val Lys Ala Trp Cys Pro Arg Pro Pro Arg Ala
                245                 250                 255

Val Glu Tyr Thr His Thr His Val Thr Asn Tyr Lys Pro Gln Asp Gly
            260                 265                 270

Asp Val Thr Thr Val Ile Pro Thr Arg Glu Asn Val Arg Ala Ile Val
        275                 280                 285

Asn Val
    290

<210> SEQ ID NO 15
<211> LENGTH: 285
<212> TYPE: PRT
<213> ORGANISM: Human rhinovirus 16

<400> SEQUENCE: 15

```
Asn Pro Val Glu Arg Tyr Val Asp Glu Val Leu Asn Glu Val Leu Val
1               5                   10                  15

Val Pro Asn Ile Asn Glu Ser His Pro Thr Thr Ser Asn Ala Ala Pro
            20                  25                  30

Val Leu Asp Ala Ala Glu Thr Gly His Thr Asn Lys Ile Gln Pro Glu
        35                  40                  45

Asp Thr Ile Glu Thr Arg Tyr Val Gln Ser Ser Gln Thr Leu Asp Glu
    50                  55                  60

Met Ser Val Glu Ser Phe Leu Gly Arg Ser Gly Cys Ile His Glu Ser
65                  70                  75                  80

Val Leu Asp Ile Val Asp Asn Tyr Asn Asp Gln Ser Phe Thr Lys Trp
                85                  90                  95

Lys Ile Asn Leu Gln Glu Met Ala Gln Ile Arg Arg Lys Phe Glu Met
            100                 105                 110

Phe Thr Tyr Ala Arg Phe Asp Ser Glu Ile Thr Met Val Pro Ser Val
        115                 120                 125

Ala Ala Lys Asp Gly His Ile Gly His Ile Val Met Gln Tyr Met Tyr
    130                 135                 140

Val Pro Pro Gly Ala Pro Ile Pro Thr Thr Arg Asn Asp Tyr Ala Trp
145                 150                 155                 160

Gln Ser Gly Thr Asn Ala Ser Val Phe Trp Gln His Gly Gln Pro Phe
                165                 170                 175

Pro Arg Phe Ser Leu Pro Phe Leu Ser Ile Ala Ser Ala Tyr Tyr Met
            180                 185                 190

Phe Tyr Asp Gly Tyr Asp Gly Asp Thr Tyr Lys Ser Arg Tyr Gly Thr
        195                 200                 205

Val Val Thr Asn Asp Met Gly Thr Leu Cys Ser Arg Ile Val Thr Ser
    210                 215                 220

Glu Gln Leu His Lys Val Lys Val Val Thr Arg Ile Tyr His Lys Ala
225                 230                 235                 240

Lys His Thr Lys Ala Trp Cys Pro Arg Pro Pro Arg Ala Val Gln Tyr
                245                 250                 255

Ser His Thr His Thr Thr Asn Tyr Lys Leu Ser Ser Glu Val His Asn
            260                 265                 270

Asp Val Ala Ile Arg Pro Arg Thr Asn Leu Thr Thr Val
        275                 280                 285
```

<210> SEQ ID NO 16
<211> LENGTH: 287
<212> TYPE: PRT
<213> ORGANISM: Human rhinovirus 18

<400> SEQUENCE: 16

```
Asn Pro Val Glu Asn Tyr Ile Asp Glu Val Leu Asn Glu Val Leu Val
1               5                   10                  15

Val Pro Asn Val Asn Glu Ser His Ala Ile Thr Ser Asn Ser Ala Pro
            20                  25                  30

Ala Leu Asp Ala Ala Glu Thr Gly His Thr Ser Asn Val Gln Pro Glu
        35                  40                  45

Asp Met Ile Glu Thr Arg Tyr Val Gln Thr Ser Gln Thr Arg Asp Glu
    50                  55                  60

Met Ser Ile Glu Ser Phe Leu Gly Arg Ser Gly Cys Ile His Ile Ser
65                  70                  75                  80
```

```
Lys Leu Val Val His Tyr Glu Asp Tyr Asn Ala Glu Thr Arg Asn Phe
                85                  90                  95

Val Lys Trp Gln Ile Asn Leu Gln Glu Met Ala Gln Ile Arg Arg Lys
            100                 105                 110

Phe Glu Met Phe Thr Tyr Val Arg Phe Asp Ser Glu Ile Thr Leu Val
            115                 120                 125

Pro Ser Val Ala Ala Lys Gly Asp Asp Ile Gly His Ile Val Met Gln
130                 135                 140

Tyr Met Tyr Val Pro Pro Gly Ala Pro Ile Pro Lys Thr Arg Asp Asp
145                 150                 155                 160

Phe Ala Trp Gln Ser Gly Thr Asn Ala Ser Ile Phe Trp Gln His Gly
                165                 170                 175

Gln Thr Tyr Pro Arg Phe Ser Leu Pro Phe Leu Ser Ile Ala Ser Ala
            180                 185                 190

Tyr Tyr Met Phe Tyr Asp Gly Tyr Asp Gly Asp Gln Thr Ser Ser Arg
            195                 200                 205

Tyr Gly Thr Val Ala Thr Asn Asp Met Gly Thr Leu Cys Ser Arg Ile
210                 215                 220

Val Thr Asp Lys His Lys Asn Glu Val Glu Ile Thr Thr Arg Ile Tyr
225                 230                 235                 240

His Lys Ala Lys His Val Lys Ala Trp Cys Pro Arg Pro Pro Arg Ala
                245                 250                 255

Val Glu Tyr Thr His Thr His Val Thr Asn Tyr Lys Pro Lys Glu Gly
            260                 265                 270

Arg Glu Lys Thr Ala Ile Val Pro Arg Ala Arg Ile Thr Met Ala
            275                 280                 285

<210> SEQ ID NO 17
<211> LENGTH: 283
<212> TYPE: PRT
<213> ORGANISM: Human rhinovirus 23

<400> SEQUENCE: 17

Asn Pro Ile Glu Asn Tyr Val Asp Glu Val Leu Asn Glu Val Leu Val
1               5                   10                  15

Val Pro Asn Ile Asn Ser Ser His Pro Thr Thr Ser Asn Ser Ala Pro
            20                  25                  30

Ala Leu Asp Ala Ala Glu Thr Gly His Thr Ser Asn Val Gln Pro Glu
        35                  40                  45

Asp Val Ile Glu Thr Arg Tyr Val Gln Thr Ser Gln Thr Arg Asp Glu
    50                  55                  60

Met Ser Leu Glu Ser Phe Leu Gly Arg Ser Gly Cys Ile His Glu Ser
65                  70                  75                  80

Lys Leu Lys Val Glu Ile Gly Asn Tyr Asp Glu Asn Asn Phe Asn Thr
                85                  90                  95

Trp Asn Ile Asn Leu Gln Glu Met Ala Gln Ile Arg Arg Lys Phe Glu
            100                 105                 110

Leu Phe Thr Tyr Thr Arg Phe Asp Ser Glu Ile Thr Leu Val Pro Cys
            115                 120                 125

Ile Ser Ala Leu Ser Gln Asp Ile Gly His Ile Thr Met Gln Tyr Met
        130                 135                 140

Tyr Val Pro Pro Gly Ala Pro Ile Pro Glu Ser Arg Asn Asp Tyr Ala
145                 150                 155                 160

Trp Gln Ser Gly Thr Asn Ala Ser Ile Phe Trp Gln His Gly Gln Thr
                165                 170                 175
```

```
Tyr Pro Arg Phe Ser Leu Pro Phe Leu Ser Val Ala Ser Ala Tyr Tyr
            180                 185                 190

Met Phe Tyr Asp Gly Tyr Asn Glu Lys Gly Thr His Tyr Gly Thr Val
        195                 200                 205

Ser Thr Asn Asn Met Gly Thr Leu Cys Ser Arg Val Val Thr Glu Lys
    210                 215                 220

His Ile His Asp Met Arg Ile Met Thr Arg Val Tyr His Lys Ala Lys
225                 230                 235                 240

His Val Lys Ala Trp Cys Pro Arg Pro Arg Ala Leu Glu Tyr Thr
                245                 250                 255

Arg Ala His Arg Thr Asn Phe Lys Ile Glu Gly Glu Asn Val Lys Ser
            260                 265                 270

Arg Val Ala His Arg Pro Ala Val Ile Thr Ala
            275                 280

<210> SEQ ID NO 18
<211> LENGTH: 282
<212> TYPE: PRT
<213> ORGANISM: Human rhinovirus 25

<400> SEQUENCE: 18

Asn Pro Ile Glu Asn Tyr Val Asp Gln Val Leu Asn Glu Val Leu Val
1               5                   10                  15

Val Pro Asn Ile Lys Glu Ser His Pro Ser Thr Ser Asn Ser Ala Pro
            20                  25                  30

Ile Leu Asp Ala Ala Glu Thr Gly His Thr Ser Asn Val Gln Pro Glu
        35                  40                  45

Asp Thr Ile Glu Thr Arg Tyr Val Gln Thr Thr Gln Thr Arg Asp Glu
    50                  55                  60

Met Ser Ile Glu Ser Phe Leu Gly Arg Ser Gly Cys Val His Thr Ser
65                  70                  75                  80

Thr Ile Glu Thr Lys Leu Lys His Asp Glu Arg Phe Lys Thr Trp Asn
                85                  90                  95

Ile Asn Leu Gln Glu Met Ala Gln Ile Arg Arg Lys Phe Glu Met Phe
            100                 105                 110

Thr Tyr Val Arg Phe Asp Ser Glu Ile Thr Leu Val Pro Ser Ile Ala
        115                 120                 125

Gly Arg Gly Ala Asp Ile Gly His Ile Val Met Gln Tyr Met Tyr Val
    130                 135                 140

Pro Pro Gly Ala Pro Leu Pro Thr Asp Arg Lys His Phe Ala Trp Gln
145                 150                 155                 160

Ser Ser Thr Asn Ala Ser Ile Phe Trp Gln His Gly Gln Pro Phe Pro
                165                 170                 175

Arg Phe Ser Leu Pro Phe Leu Ser Val Ala Ser Ala Tyr Tyr Met Phe
            180                 185                 190

Tyr Asp Gly Tyr Asn Gly Asp Asp His Thr Ala Arg Tyr Gly Thr Thr
        195                 200                 205

Val Val Asn Arg Met Gly Ala Leu Cys Met Arg Ile Val Thr Asn Lys
    210                 215                 220

Gln Val His Asp Val Glu Val Thr Thr Asn Ile Tyr His Lys Ala Lys
225                 230                 235                 240

His Val Lys Ala Trp Cys Pro Arg Pro Arg Ala Val Pro Tyr Lys
                245                 250                 255
```

```
Tyr Val Asp Phe Asn Asn Tyr Ala Ala Ser Asp Asn Val Asp Ile Phe
                260                 265                 270

Ile Gln Pro Arg Asn Ser Leu Lys Thr Ala
        275                 280

<210> SEQ ID NO 19
<211> LENGTH: 281
<212> TYPE: PRT
<213> ORGANISM: Human rhinovirus 29

<400> SEQUENCE: 19

Asn Pro Val Glu Asn Tyr Val Asp Glu Val Leu Asn Glu Val Leu Val
1               5                   10                  15

Val Pro Asn Ile Arg Glu Ser His Pro Ser Thr Ser Asn Ser Ala Pro
            20                  25                  30

Ile Leu Asp Ala Ala Glu Thr Gly His Thr Ser Asn Val Gln Pro Glu
        35                  40                  45

Asp Thr Ile Glu Thr Arg Tyr Val Gln Thr Ser His Thr Arg Asp Glu
    50                  55                  60

Met Ser Ile Glu Ser Phe Leu Gly Arg Ser Gly Cys Ile His Val Ser
65                  70                  75                  80

Thr Ile Lys Ala Asn Gln Ala His Asp Ala Lys Phe Asp Lys Trp Asn
                85                  90                  95

Val Asn Leu Gln Glu Met Ala Gln Ile Arg Arg Lys Phe Glu Met Phe
            100                 105                 110

Thr Tyr Val Arg Phe Asp Ser Glu Ile Thr Leu Val Pro Cys Ile Ala
        115                 120                 125

Gly Arg Gly Asn Asp Ile Gly His Ile Val Met Gln Tyr Met Tyr Val
    130                 135                 140

Pro Pro Gly Ala Pro Val Pro Asn Asp Arg Asn His Phe Ala Trp Gln
145                 150                 155                 160

Ser Gly Thr Asn Ala Ser Ile Phe Trp Gln His Gly Gln Pro Phe Pro
                165                 170                 175

Arg Phe Ser Leu Pro Phe Leu Ser Val Ala Ser Ala Tyr Tyr Met Phe
            180                 185                 190

Tyr Asp Gly Tyr Asn Gly Gly Asp His Thr Ala Thr Tyr Gly Thr Thr
        195                 200                 205

Val Val Asn Arg Met Gly Thr Leu Cys Val Arg Ile Val Thr Gly Lys
    210                 215                 220

Gln Ala His Asp Val Gln Val Thr Thr Ser Ile Tyr His Lys Ala Lys
225                 230                 235                 240

His Val Lys Ala Trp Cys Pro Arg Pro Arg Val Val Pro Tyr Lys
                245                 250                 255

Tyr Val Gly Leu Thr Asn Tyr Thr Leu Lys Glu Glu Asp Thr Val Val
            260                 265                 270

Glu Ser Arg Pro Ser Leu Met Thr Ala
        275                 280

<210> SEQ ID NO 20
<211> LENGTH: 288
<212> TYPE: PRT
<213> ORGANISM: Human rhinovirus 35
<220> FEATURE:
<221> NAME/KEY: misc_feature
<222> LOCATION: (46)..(46)
<223> OTHER INFORMATION: Xaa can be any naturally occurring amino acid
```

-continued

```
<220> FEATURE:
<221> NAME/KEY: misc_feature
<222> LOCATION: (89)..(89)
<223> OTHER INFORMATION: Xaa can be any naturally occurring amino acid

<400> SEQUENCE: 20

Gly Leu Gly Glu Glu Leu Glu Glu Val Ile Val Glu Lys Thr Lys Gln
1               5                   10                  15

Thr Val Ala Ser Ile Ala Ser Gly Ser Lys His Thr Gln Ser Val Pro
            20                  25                  30

Thr Leu Thr Ala Asn Glu Thr Gly Ala Ser Met Pro Val Xaa Pro Ser
        35                  40                  45

Asp Ser Val Glu Thr Arg Leu Thr Tyr Met His Phe Lys Gly Ser Glu
    50                  55                  60

Thr Asp Val Glu Ser Phe Leu Gly Arg Ala Ala Cys Val His Met Thr
65                  70                  75                  80

Glu Ile Val Asn Lys Asn Pro Ala Xaa Ser Thr Asn Gln Lys Gln Asp
                85                  90                  95

Lys Leu Phe Asn Asp Trp Arg Ile Asn Leu Ser Ser Leu Val Gln Phe
            100                 105                 110

Arg Lys Lys Leu Glu Leu Phe Thr Tyr Val Arg Phe Asp Ser Glu Tyr
        115                 120                 125

Thr Ile Leu Ala Thr Ala Ser Gln Pro Asp Asn Ser Lys Tyr Ser Ser
    130                 135                 140

Asn Leu Thr Val Gln Ala Met Tyr Val Pro Pro Gly Ala Pro Asn Pro
145                 150                 155                 160

Glu Ala Trp Asn Asp Tyr Thr Trp Gln Ser Ala Ser Asn Pro Ser Val
                165                 170                 175

Phe Phe Lys Val Gly Asp Thr Ser Arg Phe Ser Val Pro Phe Val Gly
            180                 185                 190

Leu Ala Ser Ala Tyr Asn Cys Phe Tyr Asp Gly Tyr Ser His Asp Asp
        195                 200                 205

Glu Asn Thr Pro Tyr Gly Ile Thr Val Leu Asn His Met Gly Ser Met
    210                 215                 220

Ala Phe Arg Ile Val Asn Asp His Asp Val His Thr Thr Leu Val Lys
225                 230                 235                 240

Ile Arg Val Tyr His Arg Ala Lys His Val Gln Ala Trp Ile Pro Arg
                245                 250                 255

Ala Pro Arg Ala Leu Pro Tyr Val Ser Ile Gly Arg Ser Asn Tyr Asp
            260                 265                 270

Lys Ser Ala Lys Pro Val Ile Lys Arg Arg Glu Gln Ile Thr Lys Tyr
        275                 280                 285

<210> SEQ ID NO 21
<211> LENGTH: 288
<212> TYPE: PRT
<213> ORGANISM: Human rhinovirus 37

<400> SEQUENCE: 21

Gly Leu Gly Asp Glu Leu Glu Glu Val Ile Val Glu Lys Thr Lys Gln
1               5                   10                  15

Thr Leu Ala Ser Ile Ser Ser Gly Pro Lys His Thr Gln Ser Val Pro
            20                  25                  30

Thr Leu Thr Ala Asn Glu Thr Gly Ala Thr Met Pro Thr Asn Pro Ser
        35                  40                  45
```

Asp Asn Val Glu Thr Arg Thr Thr Tyr Met His Phe Asn Gly Ser Glu
            50                   55                   60

Thr Asp Ile Glu Ser Phe Leu Gly Arg Ala Ala Cys Val His Ile Thr
 65                   70                   75                   80

Glu Ile Glu Asn Lys Asn Ser Thr Gly Ser Val Asn His Lys Ser Asp
                     85                   90                   95

Lys Leu Phe Asn Asp Trp Lys Ile Asn Leu Ser Ser Leu Val Gln Leu
                100                  105                  110

Arg Lys Lys Leu Glu Leu Phe Thr Tyr Val Arg Phe Asp Ser Glu Tyr
            115                  120                  125

Thr Ile Leu Ala Thr Ala Ser Gln Pro Ser Lys Ser Asn Tyr Ala Ser
130                  135                  140

Asn Leu Val Val Gln Ala Met Tyr Val Pro Pro Gly Ala Pro Asn Pro
145                  150                  155                  160

Lys Glu Trp Asn Asp Phe Thr Trp Gln Ser Ala Ser Asn Pro Ser Val
                165                  170                  175

Phe Phe Lys Val Gly Asp Thr Ala Arg Phe Ser Val Pro Phe Val Gly
            180                  185                  190

Leu Ala Ser Ala Tyr Asn Cys Phe Tyr Asp Gly Tyr Ser His Asp Asp
            195                  200                  205

Glu Asn Thr Pro Tyr Gly Ile Thr Val Leu Asn His Met Gly Ser Met
210                  215                  220

Ala Phe Arg Val Val Asn Glu His Asp Ala His Thr Thr Leu Val Lys
225                  230                  235                  240

Ile Arg Val Tyr His Arg Ala Lys His Val Glu Ala Trp Ile Pro Arg
                245                  250                  255

Ala Pro Arg Ala Leu Pro Tyr Glu Ala Ile Gly Lys Thr Asn Tyr Pro
            260                  265                  270

Lys Met Ile Thr Pro Val Ile Lys Lys Arg Asp Asn Ile Thr Thr Tyr
            275                  280                  285

<210> SEQ ID NO 22
<211> LENGTH: 281
<212> TYPE: PRT
<213> ORGANISM: Human rhinovirus 44

<400> SEQUENCE: 22

Asn Pro Val Glu Asn Tyr Val Asp Glu Val Leu Asn Glu Val Leu Val
 1               5                   10                  15

Val Pro Asn Ile Arg Glu Ser His Pro Ser Ile Ser Asn Ser Ala Pro
                20                  25                  30

Ile Leu Asp Ala Ala Glu Thr Gly His Thr Ser Asn Val Gln Pro Glu
            35                  40                  45

Asp Thr Ile Glu Thr Arg Tyr Val Gln Thr Ser Gln Thr Arg Asp Glu
            50                  55                  60

Met Ser Ile Glu Ser Phe Leu Gly Arg Ser Gly Cys Ile His Val Ser
 65                  70                  75                  80

Thr Ile Lys Thr Asn Gln Ala His Asn Thr Lys Phe Asp Lys Trp Asn
                     85                  90                  95

Ile Asn Leu Gln Glu Met Ala Gln Ile Arg Arg Lys Phe Glu Met Phe
                100                  105                  110

Thr Tyr Val Arg Phe Asp Ser Glu Ile Thr Leu Val Pro Cys Ile Ala
            115                  120                  125

Gly Arg Gly Asp Asp Ile Gly His Ile Val Met Gln Tyr Met Tyr Val
130                  135                  140

```
Pro Pro Gly Ala Pro Val Pro Asp Asp Arg Ile His Phe Ala Trp Gln
145                 150                 155                 160

Ser Gly Asn Asn Ala Ser Ile Phe Trp Gln His Gly Gln Pro Phe Pro
                165                 170                 175

Arg Phe Ser Leu Pro Phe Leu Ser Val Ala Ser Ala Tyr Tyr Met Phe
            180                 185                 190

Tyr Asp Gly Tyr Asn Gly Gly Asp His Thr Ala Thr Tyr Gly Thr Thr
        195                 200                 205

Val Val Asn Arg Met Gly Thr Leu Cys Val Arg Ile Val Thr Gly Lys
    210                 215                 220

Gln Ala His Asp Val Gln Val Thr Thr Ser Ile Tyr His Lys Ala Lys
225                 230                 235                 240

His Val Lys Ala Trp Cys Pro Arg Pro Pro Arg Val Val Pro Tyr Lys
                245                 250                 255

Tyr Val Gly Leu Thr Asn Tyr Thr Leu Lys Glu Thr Asp Thr Val Val
            260                 265                 270

Glu Pro Arg His Ser Ile Met Thr Ala
            275                 280

<210> SEQ ID NO 23
<211> LENGTH: 286
<212> TYPE: PRT
<213> ORGANISM: Human rhinovirus 54

<400> SEQUENCE: 23

Asn Pro Val Glu Arg Tyr Val Asp Glu Val Leu Asn Glu Val Leu Val
1               5                   10                  15

Val Pro Asn Ile Arg Glu Ser His Pro Ala Thr Ser Asn Ser Ala Pro
            20                  25                  30

Ala Leu Asp Ala Ala Glu Thr Gly His Thr Ser Gly Ile Gln Pro Glu
        35                  40                  45

Asp Thr Ile Glu Thr Arg Phe Val Gln Thr Ser Gln Thr Arg Asp Glu
    50                  55                  60

Met Ser Ile Glu Ser Phe Leu Gly Arg Ala Gly Cys Ile His Glu Ser
65                  70                  75                  80

Thr Ile Thr Ile Gln Asn Asp Val Glu Tyr Asn Asp His His Phe Lys
                85                  90                  95

Lys Trp Asp Ile Thr Leu Gln Glu Met Ala Gln Ile Arg Arg Lys Phe
            100                 105                 110

Glu Phe Phe Thr Tyr Val Arg Phe Asp Ser Glu Ile Thr Leu Val Pro
        115                 120                 125

Cys Ile Ala Gly Lys Gly Val Asp Ile Gly His Ile Val Met Gln Phe
    130                 135                 140

Met Tyr Val Pro Pro Gly Ala Pro Lys Pro Glu Lys Arg Asn Asp Tyr
145                 150                 155                 160

Thr Trp Glu Ser Ser Thr Asn Pro Ser Ile Phe Trp Gln His Gly Gln
                165                 170                 175

Ala Tyr Pro Arg Phe Ser Leu Pro Phe Leu Ser Ile Ala Ser Ala Tyr
            180                 185                 190

Tyr Met Phe Tyr Asp Gly Tyr Asp Gly Asp Ala Pro Gly Ser Arg Tyr
        195                 200                 205

Gly Thr Ser Val Thr Asn His Met Gly Thr Leu Cys Ser Arg Val Val
    210                 215                 220

Thr Gly Lys Gln Lys His Pro Val Glu Ile Thr Thr Arg Val Tyr His
225                 230                 235                 240
```

Lys Ala Lys His Ile Arg Ala Trp Cys Pro Arg Ala Pro Arg Ala Val
            245                 250                 255

Pro Tyr Thr His Thr Arg Ser Thr Asn Tyr Met Pro Arg Glu Gly Asp
            260                 265                 270

Pro Thr Ile Phe Leu Lys His Arg Thr Asn Leu Val Thr Ala
            275                 280                 285

<210> SEQ ID NO 24
<211> LENGTH: 288
<212> TYPE: PRT
<213> ORGANISM: Human rhinovirus 72

<400> SEQUENCE: 24

Leu Asn Asp Glu Leu Glu Glu Val Ile Val Glu Lys Thr Lys Gln Thr
1               5                   10                  15

Leu Ala Ser Ile Ser Ser Gly Pro Lys Tyr Thr Gln Ser Val Pro Thr
            20                  25                  30

Leu Thr Ala Asn Glu Thr Gly Ala Thr Met Pro Thr Leu Pro Ser Asp
            35                  40                  45

Asn Val Glu Thr Arg Thr Thr Tyr Met His Phe Asn Gly Ser Glu Thr
        50                  55                  60

Asp Ile Glu Cys Phe Leu Gly Arg Ala Ala Cys Val His Val Thr Glu
65                  70                  75                  80

Ile Glu Asn Lys Asn Pro Asn Gly Ile Ser Asn His Lys Ala Glu Lys
                85                  90                  95

Leu Phe Asn Asp Trp Lys Ile Ser Leu Ser Ser Leu Val Gln Leu Arg
            100                 105                 110

Lys Lys Leu Glu Leu Phe Thr Tyr Val Arg Phe Asp Ser Glu Tyr Thr
            115                 120                 125

Ile Leu Ala Thr Ala Ser Gln Pro Asp Thr Ala Asn Tyr Ser Ser Asn
        130                 135                 140

Leu Val Val Gln Ala Met Tyr Val Pro Pro Gly Ala Pro Asn Pro Val
145                 150                 155                 160

Glu Trp Asp Asp Tyr Thr Trp Gln Ser Ala Ser Asn Pro Ser Val Phe
                165                 170                 175

Phe Lys Val Gly Asp Thr Ser Arg Phe Ser Val Pro Tyr Val Gly Leu
            180                 185                 190

Ala Ser Ala Tyr Asn Cys Phe Tyr Asp Gly Tyr Ser His Asp Asp Ala
        195                 200                 205

Glu Thr Gln Tyr Gly Ile Ser Val Leu Asn His Met Gly Ser Met Ala
    210                 215                 220

Phe Arg Ile Val Asn Glu His Asp Thr His Arg Thr Leu Val Lys Ile
225                 230                 235                 240

Arg Val Tyr His Arg Ala Lys His Ile Glu Ala Trp Val Pro Arg Ala
                245                 250                 255

Pro Arg Ala Leu Pro Tyr Thr Ser Ile Gly Arg Thr Asn Tyr Pro Lys
            260                 265                 270

Asn Pro Lys Pro Val Ile Lys Lys Arg Glu Gly Asp Ile Lys Thr Tyr
            275                 280                 285

<210> SEQ ID NO 25
<211> LENGTH: 289
<212> TYPE: PRT
<213> ORGANISM: Human rhinovirus 83

<400> SEQUENCE: 25

```
Gly Leu Asn Asp Glu Leu Glu Glu Val Ile Val Glu Lys Thr Arg Gln
1               5                   10                  15
Thr Leu Ala Ser Val Ala Ser Gly Pro Lys His Thr Gln Ser Val Pro
            20                  25                  30
Ile Leu Thr Ala Asn Glu Thr Gly Ala Thr Met Pro Thr Gln Pro Ser
        35                  40                  45
Asp Asn Val Glu Thr Arg Thr Thr Tyr Met His Phe Asn Gly Ser Glu
50                  55                  60
Thr Asp Ile Glu Ser Phe Leu Gly Arg Ala Ala Cys Val His Met Val
65                  70                  75                  80
Glu Ile Val Asn Lys Asn Pro Leu Asn Ile Lys Asn Gln Lys Arg Glu
                85                  90                  95
Lys Leu Phe Asn Glu Trp Arg Ile Asn Leu Ser Ser Leu Val Gln Leu
            100                 105                 110
Arg Lys Lys Leu Glu Leu Phe Thr Tyr Ala Arg Phe Asp Ser Glu Tyr
        115                 120                 125
Thr Ile Leu Ala Thr Ala Ser Gln Pro Thr Asn Ser Ser Tyr Ser Ser
130                 135                 140
Asp Leu Thr Val Gln Ala Met Tyr Val Pro Pro Gly Ala Pro Asn Pro
145                 150                 155                 160
Thr Lys Trp Asp Asp Tyr Thr Trp Gln Ser Ala Ser Asn Pro Ser Val
                165                 170                 175
Phe Phe Lys Val Gly Asp Thr Ala Arg Phe Ser Val Pro Phe Val Gly
            180                 185                 190
Leu Ala Ser Ala Tyr Asn Cys Phe Tyr Asp Gly Tyr Ser His Asp Asp
        195                 200                 205
Glu Asp Thr Pro Tyr Gly Ile Thr Val Leu Asn His Met Gly Ser Met
210                 215                 220
Ala Phe Arg Val Val Asn Glu His Asp Ala His Thr Thr Glu Val Lys
225                 230                 235                 240
Ile Arg Val Tyr His Arg Ala Lys His Val Gln Val Trp Val Pro Arg
                245                 250                 255
Ala Pro Arg Ala Leu Pro Tyr Val Ser Ile Gly Arg Thr Asn Tyr Glu
            260                 265                 270
Arg Gln Asn Ile Lys Pro Val Ile Glu Lys Arg Thr Ser Ile Lys Gln
        275                 280                 285
Tyr
```

<210> SEQ ID NO 26
<211> LENGTH: 287
<212> TYPE: PRT
<213> ORGANISM: Human rhinovirus 86

<400> SEQUENCE: 26

```
Leu Gly Asp Glu Leu Glu Glu Val Ile Val Glu Lys Thr Lys Gln Thr
1               5                   10                  15
Leu Ala Ser Val Ala Thr Gly Ser Lys Tyr Thr Gln Lys Val Pro Ser
            20                  25                  30
Leu Ser Ala Asn Glu Thr Gly Ala Thr Met Pro Thr Val Pro Ser Asp
        35                  40                  45
Asn Ile Glu Thr Arg Thr Thr Tyr Met Asn Phe Thr Gly Ser Glu Thr
50                  55                  60
```

-continued

```
Asp Val Glu Cys Phe Leu Gly Arg Ala Ala Cys Val His Ile Thr Glu
 65                  70                  75                  80

Ile Glu Asn Lys Asp Pro Thr Asp Ile Glu Asn Gln Lys Glu Ala Lys
                 85                  90                  95

Leu Phe Asn Asp Trp Lys Ile Asn Leu Ser Ser Leu Val Gln Leu Arg
            100                 105                 110

Lys Lys Leu Glu Leu Phe Thr Tyr Val Arg Phe Asp Ser Glu Tyr Thr
        115                 120                 125

Ile Leu Ala Thr Ala Ser Gln Pro Thr Gln Ser Ser Tyr Ser Ser Asn
    130                 135                 140

Leu Thr Val Gln Ala Met Tyr Val Pro Pro Gly Ala Pro Asn Pro Lys
145                 150                 155                 160

Thr Trp Asn Asp Tyr Thr Trp Gln Ser Ala Ser Asn Pro Ser Val Phe
                165                 170                 175

Phe Lys Val Gly Asp Thr Ala Arg Phe Ser Val Pro Phe Val Gly Leu
            180                 185                 190

Ala Ser Ala Tyr Ser Cys Phe Tyr Asp Gly Tyr Ser His Asp Asn Glu
        195                 200                 205

Asp Thr Pro Tyr Gly Ile Thr Val Leu Asn His Met Gly Ser Ile Ala
    210                 215                 220

Phe Arg Val Val Asn Asp His Asp Leu His Lys Thr Val Val Lys Ile
225                 230                 235                 240

Arg Val Tyr His Arg Ala Lys His Ile Gln Thr Trp Ile Pro Arg Ala
                245                 250                 255

Pro Arg Ala Leu Pro Tyr Glu Thr Ile Gly Arg Thr Asn Phe Pro Arg
            260                 265                 270

Asn Pro Pro Lys Ile Ile Lys Lys Arg Asp Thr Ile Asn Thr Tyr
        275                 280                 285

<210> SEQ ID NO 27
<211> LENGTH: 292
<212> TYPE: PRT
<213> ORGANISM: Human rhinovirus 89

<400> SEQUENCE: 27

Asn Pro Val Glu Asn Tyr Ile Asp Ser Val Leu Asn Glu Val Leu Val
  1               5                  10                  15

Val Pro Asn Ile Gln Pro Ser Thr Ser Val Ser Ser His Ala Ala Pro
             20                  25                  30

Ala Leu Asp Ala Ala Glu Thr Gly His Thr Ser Ser Val Gln Pro Glu
         35                  40                  45

Asp Met Ile Glu Thr Arg Tyr Val Ile Thr Asp Gln Thr Arg Asp Glu
     50                  55                  60

Thr Ser Ile Glu Ser Phe Leu Gly Arg Ser Gly Cys Ile Ala Met Ile
 65                  70                  75                  80

Glu Phe Asn Thr Ser Ser Asp Lys Thr Glu His Asp Lys Ile Gly Lys
                 85                  90                  95

Gly Phe Lys Thr Trp Lys Val Ser Leu Gln Glu Met Ala Gln Ile Arg
            100                 105                 110

Arg Lys Tyr Glu Leu Phe Thr Tyr Thr Arg Phe Asp Ser Glu Ile Thr
        115                 120                 125

Ile Val Thr Ala Ala Ala Ala Gln Gly Asn Asp Ser Gly His Ile Val
    130                 135                 140

Leu Gln Phe Met Tyr Val Pro Pro Gly Ala Pro Val Pro Glu Lys Arg
145                 150                 155                 160
```

Asp Asp Tyr Thr Trp Gln Ser Gly Thr Asn Ala Ser Val Phe Trp Gln
                165                 170                 175

Glu Gly Gln Pro Tyr Pro Arg Phe Thr Ile Pro Phe Met Ser Ile Ala
            180                 185                 190

Ser Ala Tyr Tyr Met Phe Tyr Asp Gly Tyr Asp Gly Asp Ser Ala Ala
            195                 200                 205

Ser Lys Tyr Gly Ser Val Val Thr Asn Asp Met Gly Thr Ile Cys Val
        210                 215                 220

Arg Ile Val Thr Ser Asn Gln Lys His Asp Leu Asn Ile Val Cys Arg
225                 230                 235                 240

Ile Tyr His Lys Ala Lys His Ile Lys Ala Trp Cys Pro Arg Pro Pro
                245                 250                 255

Arg Ala Val Ala Tyr Gln His Thr His Ser Thr Asn Tyr Ile Pro Ser
            260                 265                 270

Asn Gly Glu Ala Thr Thr Gln Ile Lys Thr Arg Pro Asp Val Phe Thr
        275                 280                 285

Val Thr Asn Val
    290

<210> SEQ ID NO 28
<211> LENGTH: 289
<212> TYPE: PRT
<213> ORGANISM: Human rhinovirus 92

<400> SEQUENCE: 28

Gly Leu Asn Asp Glu Leu Glu Glu Val Ile Val Glu Lys Thr Lys Gln
1               5                   10                  15

Thr Leu Ala Ser Ile Thr Ser Gly Pro Lys His Thr Gln Ser Val Pro
            20                  25                  30

Thr Leu Thr Ala Asn Glu Thr Gly Ala Thr Met Pro Thr Gln Pro Ser
        35                  40                  45

Asp Asn Val Glu Thr Arg Thr Thr Tyr Met His Phe Asn Gly Ser Glu
    50                  55                  60

Thr Asp Val Glu Asn Phe Leu Gly Arg Ala Ala Cys Val His Met Val
65                  70                  75                  80

Glu Ile Val Asn Lys Asn Pro Glu Gly Leu Glu Asn Gln Lys Glu His
                85                  90                  95

Lys Leu Phe Asn Asp Trp Arg Ile Asn Leu Ser Ser Leu Val Gln Leu
            100                 105                 110

Arg Lys Lys Leu Glu Leu Phe Thr Tyr Val Arg Phe Asp Ser Glu Tyr
        115                 120                 125

Thr Ile Leu Ala Thr Ala Ser Gln Pro Thr Ser Ser Lys Tyr Ser Ser
    130                 135                 140

Ser Leu Thr Val Gln Ala Met Tyr Val Pro Pro Gly Ala Pro Asn Pro
145                 150                 155                 160

Thr Lys Trp Asp Asp Tyr Thr Trp Gln Ser Ala Ser Asn Pro Ser Val
                165                 170                 175

Phe Phe Lys Val Gly Asp Thr Ala Arg Phe Ser Val Pro Phe Val Gly
            180                 185                 190

Leu Ala Ser Ala Tyr Asn Cys Phe Tyr Asp Gly Tyr Ser His Asp Asp
        195                 200                 205

Glu Asp Thr Pro Tyr Gly Ile Thr Val Leu Asn His Met Gly Ser Met
    210                 215                 220

Ala Phe Arg Ile Val Asn Glu His Asp Ala His Thr Thr Glu Val Lys
225                 230                 235                 240

```
Ile Arg Val Tyr His Arg Ala Lys His Val Glu Ala Trp Ile Pro Arg
                245                 250                 255
Ala Pro Arg Ala Leu Pro Tyr Val Ser Ile Gly Arg Thr Asn Tyr Asn
            260                 265                 270
Lys Gln Ala Ile Val Pro Val Ile Lys Lys Arg Ser Leu Ile Thr Asn
        275                 280                 285
Tyr

<210> SEQ ID NO 29
<211> LENGTH: 238
<212> TYPE: PRT
<213> ORGANISM: Human rhinovirus C

<400> SEQUENCE: 29

Asn Pro Val Glu Gln Phe Val Asp Asn Val Leu Glu Glu Val Leu Val
1               5                   10                  15
Val Pro Asn Thr Gln Pro Ser Gly Pro Ile His Thr Thr Lys Pro Thr
            20                  25                  30
Ala Leu Ser Ala Met Glu Ile Gly Ala Ser Ser Asp Val Lys Pro Glu
        35                  40                  45
Asp Met Ile Glu Thr Arg Tyr Val Val Asn Ser Arg Thr Asn Asp Glu
    50                  55                  60
Ala Thr Ile Glu Asn Phe Leu Gly Arg Ser Ala Leu Trp Ala Asn Val
65                  70                  75                  80
Asn Met Thr Asp Gly Tyr Ala Thr Trp Ser Ile Thr Tyr Gln Gly Asn
                85                  90                  95
Ala Gln Ile Arg Lys Lys Leu Glu Leu Phe Thr Tyr Val Arg Phe Asp
            100                 105                 110
Leu Glu Ile Thr Ile Ile Thr Ser Ser Ser Asp Leu Ile Gln Ile Met
        115                 120                 125
Tyr Val Pro Pro Gly Ala Asn Thr Pro Arg Ser Asn Asn Ala Thr Glu
    130                 135                 140
Trp Asn Thr Ala Ser Asn Pro Ser Ile Phe Phe Gln Pro Gly Asn Gly
145                 150                 155                 160
Phe Pro Arg Phe Thr Ile Pro Phe Thr Gly Leu Gly Ser Ala Tyr Tyr
                165                 170                 175
Met Phe Tyr Asp Gly Tyr Asp Ile Val Ser His Glu Asn Gly Ile Tyr
            180                 185                 190
Gly Ile Ser Thr Thr Asn Asp Met Gly Ser Leu Cys Phe Arg Thr Pro
        195                 200                 205
Asn Asn Ser Ser Gly Thr Glu Ile Ile Arg Val Phe Gly Lys Pro Lys
    210                 215                 220
His Thr Arg Ala Trp Ile Pro Arg Pro Arg Ala Thr Gly
225                 230                 235

<210> SEQ ID NO 30
<211> LENGTH: 882
<212> TYPE: DNA
<213> ORGANISM: Human rhinovirus 89

<400> SEQUENCE: 30
atgaacccgg tggaaaacta tattgatagc gtgctgaacg aagtgctggt ggtgccgaac      60
attcagccga gcaccagcgt gagcagccat gcggcgccgg cgctggatgc ggcggaaacc     120
ggccatacca gcagcgtgca gccggaagat atgattgaaa cccgttatgt gattaccgat     180
cagacccgtg atgaaaccag cattgaaagc tttctgggcc gtagcggctg cattgcgatg     240
```

```
attgaattta acaccagcag cgataaaacc gaacatgata aaattggcaa aggctttaaa    300
acctggaaaa ttagcctgca ggaaatggcg cagattcgtc gtaaatatga actgtttacc    360 tataccgtt ttgatagcga aattaccatt gtgaccgcgg cggcggcgca gggcgatgat    420
agcggccata ttgtgctgca gtttatgtat gtgccgccgg gcgcgccggt gccggaaaaa    480
cgtgatgatt atacctggca gagcggcacc aacgcgagcg tgttttggca ggaaggccag    540
ccgtatccgc gttttaccat tccgtttatg agcattgcga gcgcgtatta tatgttttat    600
gatggctatg atggcgatag cgcggcgagc aaatatggca gcgtggtgac caacgatatg    660
ggcaccattt gcgtgcgtat tgtgaccagc aaccagaaac atgatctgaa cattgtgtgc    720
cgtatttatc ataaagcgaa acatattaaa gcgtggtgcc cgcgtccgcc gcgtgcggtg    780
gcgtatcagc ataccatag caccaactat attccgagca acggcgaagc gaccacccag    840
attaaaaccc gtccggatgt gtttaccggc accaacgtgt aa                      882

<210> SEQ ID NO 31
<211> LENGTH: 807
<212> TYPE: DNA
<213> ORGANISM: Human rhinovirus 89

<400> SEQUENCE: 31
atgagcccaa ccgtggaagc gtgcggttac agcgaccgtc tgatccagat tacccgtggt    60
gacagtacta ttacttctca ggatacggcg aacgcggttg ttgcatacgg tgtttggccg    120
agctatctga cgccggatga tgctactgca attgataaac ctacccagcc tgatactagc    180
agcaaccgtt tctataccct ggactctcgc agctggacga gtgccagcag cgggtggtgg    240
tggaaactgc cagacgcact gaagaatatg ggtatctttg gtgaaaatat gttttatcat    300
tttctgggtc gttctggcta tacgatccac gtacagtgca atagcagcaa atttcatcag    360
ggcctgctga tcgtggcggc tattccggag catcagctgg ccagcgctac cagcggtaat    420
gtaagcgtgg gttacaatca tacacatcca ggtgaacagg gccgcgaggt agtgccgtct    480
cgcaccagta gtgataacaa gcgtccgtct gatgattctt ggctgaattt tgatggcacg    540
ctgctgggca acctgccaat ttacccgcac cagtatatca atctgcgcac caacaacagc    600
gccacactga tcctgcctta tgtcaacgcc gtgcctatgg actctatgct cgccacaac    660 aattggtctc tggtgattat cccgatttgt ccgctgcaag ttcaaccagg tggcacacaa    720
tctattccga tcaccgtttc tattagtccg atgttcagtg agttcagtgg cccacgtagt    780
aaggtcgtct tcagtacaac ccaataa                                       807

<210> SEQ ID NO 32
<211> LENGTH: 267
<212> TYPE: PRT
<213> ORGANISM: Human rhinovirus 89

<400> SEQUENCE: 32

Ser Pro Thr Val Glu Ala Cys Gly Tyr Ser Asp Arg Leu Ile Gln Ile
1               5                   10                  15

Thr Arg Gly Asp Ser Thr Ile Thr Ser Gln Asp Thr Ala Asn Ala Val
            20                  25                  30

Val Ala Tyr Gly Val Trp Pro Ser Tyr Leu Thr Pro Asp Asp Ala Thr
        35                  40                  45

Ala Ile Asp Lys Pro Thr Gln Pro Asp Thr Ser Ser Asn Arg Phe Tyr
    50                  55                  60
```

-continued

```
Thr Leu Asp Ser Arg Ser Trp Thr Ser Ala Ser Ser Gly Trp Trp Trp
 65                  70                  75                  80
Lys Leu Pro Asp Ala Leu Lys Asn Met Gly Ile Phe Gly Glu Asn Met
                 85                  90                  95
Phe Tyr His Phe Leu Gly Arg Ser Gly Tyr Thr Ile His Val Gln Cys
            100                 105                 110
Asn Ser Ser Lys Phe His Gln Gly Leu Leu Ile Val Ala Ala Ile Pro
        115                 120                 125
Glu His Gln Leu Ala Ser Ala Thr Ser Gly Asn Val Ser Val Gly Tyr
    130                 135                 140
Asn His Thr His Pro Gly Glu Gln Gly Arg Glu Val Val Pro Ser Arg
145                 150                 155                 160
Thr Ser Ser Asp Asn Lys Arg Pro Ser Asp Asp Ser Trp Leu Asn Phe
                165                 170                 175
Asp Gly Thr Leu Leu Gly Asn Leu Pro Ile Tyr Pro His Gln Tyr Ile
            180                 185                 190
Asn Leu Arg Thr Asn Asn Ser Ala Thr Leu Ile Leu Pro Tyr Val Asn
        195                 200                 205
Ala Val Pro Met Asp Ser Met Leu Arg His Asn Asn Trp Ser Leu Val
    210                 215                 220
Ile Ile Pro Ile Cys Pro Leu Gln Val Gln Pro Gly Gly Thr Gln Ser
225                 230                 235                 240
Ile Pro Ile Thr Val Ser Ile Ser Pro Met Phe Ser Glu Phe Ser Gly
                245                 250                 255
Pro Arg Ser Lys Val Val Phe Ser Thr Thr Gln
            260                 265
```

<210> SEQ ID NO 33
<211> LENGTH: 720
<212> TYPE: DNA
<213> ORGANISM: Human rhinovirus 89

<400> SEQUENCE: 33

```
atgggcctgc cagtgatgct gacaccgggg agtggtcagt tcctgacgac agacgatacc    60
caaagcccga gtgcattccc gtattttcat ccaacaaagg aaatcttat tccggggcag     120
gttcgtaacc tgattgagat gtgtcaagta gacactctga tcccggtgaa caacactcag    180
gaaaacgtgc gcagcgtgaa tatgtacacg gtcgatctgc gcactcaggt agacctggca    240
aaggaggtgt ctctctatcc ggtggatatt gcgagccaac cactggcgac gaccctgatc    300
ggcgaactgg cgagctatta cactcattgg acgggtagtc tgcgttttag tttcatgttt    360
tgtggctctg caagtagcac tctgaaactg ctgattgcgt acacccgcc gggtgtcggt    420
aaaccaaaga gccgccgcga agctatgctg ggtacgcatc tggtgtggga tgtaggcctg    480
caaagtacgg cttctctggt agtcccttgg gtctctgcga gccactttcg tttcaccaca    540
ccggacacct attcttctgc cggctatatt acctgttggt atcagaccaa ttttgtggtt    600
cctgatagca cccctgataa tgccaaaatg gtttgcatgg ttagcgcctg caaagatttc    660
tgcctgcgtc tggcccgtga caccaatctg cacacacagg aaggcgttct gacccaataa    720
```

<210> SEQ ID NO 34
<211> LENGTH: 238
<212> TYPE: PRT
<213> ORGANISM: Human rhinovirus 89

-continued

<400> SEQUENCE: 34

Gly Leu Pro Val Met Leu Thr Pro Gly Ser Gly Gln Phe Leu Thr Thr
1               5                   10                  15

Asp Asp Thr Gln Ser Pro Ser Ala Phe Pro Tyr Phe His Pro Thr Lys
            20                  25                  30

Glu Ile Phe Ile Pro Gly Gln Val Arg Asn Leu Ile Glu Met Cys Gln
        35                  40                  45

Val Asp Thr Leu Ile Pro Val Asn Asn Thr Gln Glu Asn Val Arg Ser
    50                  55                  60

Val Asn Met Tyr Thr Val Asp Leu Arg Thr Gln Val Asp Leu Ala Lys
65                  70                  75                  80

Glu Val Phe Ser Ile Pro Val Asp Ile Ala Ser Gln Pro Leu Ala Thr
                85                  90                  95

Thr Leu Ile Gly Glu Leu Ala Ser Tyr Tyr Thr His Trp Thr Gly Ser
            100                 105                 110

Leu Arg Phe Ser Phe Met Phe Cys Gly Ser Ala Ser Ser Thr Leu Lys
        115                 120                 125

Leu Leu Ile Ala Tyr Thr Pro Pro Gly Val Gly Lys Pro Lys Ser Arg
    130                 135                 140

Arg Glu Ala Met Leu Gly Thr His Leu Val Trp Asp Val Gly Leu Gln
145                 150                 155                 160

Ser Thr Ala Ser Leu Val Val Pro Trp Val Ser Ala Ser His Phe Arg
                165                 170                 175

Phe Thr Thr Pro Asp Thr Tyr Ser Ser Ala Gly Tyr Ile Thr Cys Trp
            180                 185                 190

Tyr Gln Thr Asn Phe Val Val Pro Asp Ser Thr Pro Asp Asn Ala Lys
        195                 200                 205

Met Val Cys Met Val Ser Ala Cys Lys Asp Phe Cys Leu Arg Leu Ala
    210                 215                 220

Arg Asp Thr Asn Leu His Thr Gln Glu Gly Val Leu Thr Gln
225                 230                 235

<210> SEQ ID NO 35
<211> LENGTH: 50
<212> TYPE: DNA
<213> ORGANISM: Artificial Sequence
<220> FEATURE:
<223> OTHER INFORMATION: Primer

<400> SEQUENCE: 35
cggaattccc atgggcttag gtgatgaatt agaagaagtc atcgttgaga            50

<210> SEQ ID NO 36
<211> LENGTH: 48
<212> TYPE: DNA
<213> ORGANISM: Artificial Sequence
<220> FEATURE:
<223> OTHER INFORMATION: Primer

<400> SEQUENCE: 36
gatggaattc tcagtggtgg tggtggtggt gataggattt aatgtcac              48

<210> SEQ ID NO 37
<211> LENGTH: 50
<212> TYPE: DNA
<213> ORGANISM: Artificial Sequence
<220> FEATURE:
<223> OTHER INFORMATION: Primer

<400> SEQUENCE: 37
cggaattcat taatatgaac ccagttgaaa attatataga tagtgtatta            50

<210> SEQ ID NO 38
<211> LENGTH: 46
<212> TYPE: DNA
<213> ORGANISM: Artificial Sequence
<220> FEATURE:
<223> OTHER INFORMATION: Primer

<400> SEQUENCE: 38
cgattaattc agtggtggtg gtggtggtgg acgtttgtaa cggtaa                46

<210> SEQ ID NO 39
<211> LENGTH: 17
<212> TYPE: PRT
<213> ORGANISM: Artificial Sequence
<220> FEATURE:
<223> OTHER INFORMATION: HRV14-derived peptide

<400> SEQUENCE: 39

Val Val Gln Ala Met Tyr Val Pro Pro Gly Ala Pro Asn Pro Lys Glu
1               5                   10                  15

Cys

<210> SEQ ID NO 40
<211> LENGTH: 35
<212> TYPE: PRT
<213> ORGANISM: Artificial Sequence
<220> FEATURE:
<223> OTHER INFORMATION: HRV14-derived peptide

<400> SEQUENCE: 40

Cys Arg Ala Pro Arg Ala Leu Pro Tyr Thr Ser Ile Gly Arg Thr Asn
1               5                   10                  15

Tyr Pro Lys Asn Thr Glu Pro Val Ile Lys Lys Arg Lys Gly Asp Ile
            20                  25                  30

Lys Ser Tyr
        35

<210> SEQ ID NO 41
<211> LENGTH: 17
<212> TYPE: PRT
<213> ORGANISM: Artificial Sequence
<220> FEATURE:
<223> OTHER INFORMATION: HRV14-derived peptide

<400> SEQUENCE: 41

Lys Leu Ile Leu Ala Tyr Thr Pro Pro Gly Ala Arg Gly Pro Gln Asp
1               5                   10                  15

Cys

<210> SEQ ID NO 42
<211> LENGTH: 32
<212> TYPE: PRT
<213> ORGANISM: Artificial Sequence
<220> FEATURE:
<223> OTHER INFORMATION: VP1-derived epitope Ep_1a

```
<400> SEQUENCE: 42

Met Asn Pro Val Glu Asn Tyr Ile Asp Ser Val Leu Asn Glu Val Leu
1               5                   10                  15

Val Val Pro Asn Ile Gln Pro Ser Thr Ser Val Ser Ser His Ala Ala
            20                  25                  30

<210> SEQ ID NO 43
<211> LENGTH: 34
<212> TYPE: PRT
<213> ORGANISM: Artificial Sequence
<220> FEATURE:
<223> OTHER INFORMATION: VP1-derived epitope Ep 1b

<400> SEQUENCE: 43

Pro Ala Leu Asp Ala Ala Glu Thr Gly His Thr Ser Ser Val Gln Pro
1               5                   10                  15

Glu Asp Met Ile Glu Thr Arg Tyr Val Ile Thr Asp Gln Thr Arg Asp
            20                  25                  30

Glu Thr

<210> SEQ ID NO 44
<211> LENGTH: 34
<212> TYPE: PRT
<213> ORGANISM: Artificial Sequence
<220> FEATURE:
<223> OTHER INFORMATION: VP1-derived epitope Ep 1c

<400> SEQUENCE: 44

Ser Ile Glu Ser Phe Leu Gly Arg Ser Gly Cys Ile Ala Met Ile Glu
1               5                   10                  15

Phe Asn Thr Ser Ser Asp Lys Thr Glu His Asp Lys Ile Gly Lys Gly
            20                  25                  30

Phe Lys

<210> SEQ ID NO 45
<211> LENGTH: 274
<212> TYPE: PRT
<213> ORGANISM: Human rhinovirus C

<400> SEQUENCE: 45

Asn Pro Val Glu Asp Tyr Ile Asp Lys Val Val Asp Thr Val Leu Gln
1               5                   10                  15

Val Pro Asn Thr Gln Pro Ser Gly Pro Gln His Ser Ile Gln Pro Ser
            20                  25                  30

Ala Leu Gly Ala Met Glu Ile Gly Ala Ser Ser Thr Thr Ile Pro Gly
        35                  40                  45

Asp Leu Ile Glu Thr Arg Tyr Val Ile Asn Ser Asn Thr Asn Ser Glu
    50                  55                  60

Ala Leu Ile Glu Asn Phe Met Gly Arg Ser Ala Leu Trp Ala Lys Ile
65                  70                  75                  80

Gln Val Ala Asn Gly Phe Ala Lys Trp Asp Ile Asn Phe Gln Glu His
                85                  90                  95

Ala Gln Val Arg Lys Lys Phe Glu Met Phe Thr Tyr Ala Arg Phe Asp
            100                 105                 110

Met Glu Val Thr Val Val Thr Asn Asn Thr Gly Leu Val Gln Ile Met
        115                 120                 125

Phe Val Pro Pro Gly Ile Asp Ala Pro Asp Ser Ile Asp Ser Arg Leu
    130                 135                 140
```

```
Trp Asp Ser Ala Ser Asn Pro Ser Val Phe Tyr Gln Pro Lys Ser Gly
145                 150                 155                 160

Phe Pro Arg Phe Thr Ile Pro Phe Thr Gly Leu Gly Ser Ala Tyr Tyr
            165                 170                 175

Met Phe Tyr Asp Gly Tyr Asp Val Pro Arg Asn Lys Ser Asn Ala Val
            180                 185                 190

Tyr Gly Ile Thr Ser Thr Asn Asp Met Gly Thr Leu Cys Phe Arg Ala
            195                 200                 205

Met Glu Asp Thr Asn Glu His Ser Ile Arg Val Phe Val Lys Pro Lys
            210                 215                 220

His Thr Ile Ala Trp Ile Pro Arg Pro Arg Ala Thr Gln Tyr Thr
225                 230                 235                 240

His Lys Phe Ser Thr Asn Tyr His Val Lys Lys Pro Asp Asp Thr Thr
            245                 250                 255

Gly Leu Leu Ile Gln Lys His Phe Ile Asn His Arg Thr Asp Ile Lys
            260                 265                 270

Thr Ala

<210> SEQ ID NO 46
<211> LENGTH: 237
<212> TYPE: DNA
<213> ORGANISM: Human rhinovirus 89

<400> SEQUENCE: 46
catatgggcg cccaggtgtc tcgtcagaac gtcggcacgc atagcacgca gaacagtgtg      60
tccaacggct cgtcgctgaa ctacttcaac atcaactatt ttaaagatgc agccagctct    120
ggtgcgagcc gtctggattt tagtcaggac ccgtccaaat tcaccgaccc ggtcaaagat    180
gtcctggaaa aaggtatccc gaccctgcaa caccaccacc accaccacta actccag      237

<210> SEQ ID NO 47
<211> LENGTH: 74
<212> TYPE: PRT
<213> ORGANISM: Artificial Sequence
<220> FEATURE:
<223> OTHER INFORMATION: VP4 of human rhinovirus 89

<400> SEQUENCE: 47

Gly Ala Gln Val Ser Arg Gln Asn Val Gly Thr His Ser Thr Gln Asn
1               5                   10                  15

Ser Val Ser Asn Gly Ser Ser Leu Asn Tyr Phe Asn Ile Asn Tyr Phe
            20                  25                  30

Lys Asp Ala Ala Ser Ser Gly Ala Ser Arg Leu Asp Phe Ser Gln Asp
            35                  40                  45

Pro Ser Lys Phe Thr Asp Pro Val Lys Asp Val Leu Glu Lys Gly Ile
        50                  55                  60

Pro Thr Leu Gln His His His His His His
65                  70

<210> SEQ ID NO 48
<211> LENGTH: 31
<212> TYPE: PRT
<213> ORGANISM: Artificial Sequence
<220> FEATURE:
<223> OTHER INFORMATION: Human Rhinoviurs VP1 fragment

```
<400> SEQUENCE: 48

Asn Pro Val Glu Asn Tyr Ile Asp Ser Val Leu Asn Glu Val Leu Val
1               5                  10                  15

Val Pro Asn Ile Gln Pro Ser Thr Ser Val Ser Ser His Ala Ala
            20                  25                  30

<210> SEQ ID NO 49
<211> LENGTH: 21
<212> TYPE: PRT
<213> ORGANISM: Artificial Sequence
<220> FEATURE:
<223> OTHER INFORMATION: Human Rhinovirus VP1 fragment

<400> SEQUENCE: 49

Asn Pro Val Glu Asn Tyr Ile Asp Ser Val Leu Asn Glu Val Leu Val
1               5                  10                  15

Val Pro Asn Ile Gln
            20

<210> SEQ ID NO 50
<211> LENGTH: 8
<212> TYPE: PRT
<213> ORGANISM: Artificial Sequence
<220> FEATURE:
<223> OTHER INFORMATION: Human Rhinovirus VP1 fragment

<400> SEQUENCE: 50

Asn Pro Val Glu Asn Tyr Ile Asp
1               5

<210> SEQ ID NO 51
<211> LENGTH: 34
<212> TYPE: PRT
<213> ORGANISM: Artificial Sequence
<220> FEATURE:
<223> OTHER INFORMATION: Human Rhinovirus VP1 fragment

<400> SEQUENCE: 51

Pro Ala Leu Asp Ala Ala Glu Thr Gly His Thr Ser Ser Val Gln Pro
1               5                  10                  15

Glu Asp Met Ile Glu Thr Arg Tyr Val Ile Thr Asp Gln Thr Arg Asp
            20                  25                  30

Glu Thr

<210> SEQ ID NO 52
<211> LENGTH: 34
<212> TYPE: PRT
<213> ORGANISM: Artificial Sequence
<220> FEATURE:
<223> OTHER INFORMATION: Human Rhinovirus VP1 fragment

<400> SEQUENCE: 52

Ser Ile Glu Ser Phe Leu Gly Arg Ser Gly Cys Ile Ala Met Ile Glu
1               5                  10                  15

Phe Asn Thr

```
<220> FEATURE:
<223> OTHER INFORMATION: Human Rhinovirus VP1 fragment

<400> SEQUENCE: 53

Val Val Pro Asn Ile Gln Pro Ser Thr Ser Val Ser Ser His Ala Ala
1               5                   10                  15

Pro Ala Leu Asp
            20

<210> SEQ ID NO 54
<211> LENGTH: 20
<212> TYPE: PRT
<213> ORGANISM: Artificial Sequence
<220> FEATURE:
<223> OTHER INFORMATION: Human Rhinovirus VP1 fragment

<400> SEQUENCE: 54

Ala Pro Ala Leu Asp Ala Ala Glu Thr Gly His Thr Ser Ser Val Gln
1               5                   10                  15

Pro Glu Asp Met
            20

<210> SEQ ID NO 55
<211> LENGTH: 20
<212> TYPE: PRT
<213> ORGANISM: Artificial Sequence
<220> FEATURE:
<223> OTHER INFORMATION: Human Rhinovirus VP1 fragment

<400> SEQUENCE: 55

Gln Pro Glu Asp Met Ile Glu Thr Arg Tyr Val Ile Thr Asp Gln Thr
1               5                   10                  15

Arg Asp Glu Thr
            20

<210> SEQ ID NO 56
<211> LENGTH: 20
<212> TYPE: PRT
<213> ORGANISM: Artificial Sequence
<220> FEATURE:
<223> OTHER INFORMATION: Human Rhinovirus VP1 fragment

<400> SEQUENCE: 56

Thr Arg Asp Glu Thr Ser Ile Glu Ser Phe Leu Gly Arg Ser Gly Cys
1               5                   10                  15

Ile Ala Met Ile
            20

<210> SEQ ID NO 57
<211> LENGTH: 20
<212> TYPE: PRT
<213> ORGANISM: Artificial Sequence
<220> FEATURE:
<223> OTHER INFORMATION: Human Rhinovirus VP1 fragment

<400> SEQUENCE: 57

Cys Ile Ala Met Ile Glu Phe Asn Thr Ser Ser Asp Lys Thr Glu His
1               5                   10                  15

Asp Lys Ile Gly
            20
```

<210> SEQ ID NO 58
<211> LENGTH: 20
<212> TYPE: PRT
<213> ORGANISM: Artificial Sequence
<220> FEATURE:
<223> OTHER INFORMATION: Human Rhinovirus VP1 fragment

<400> SEQUENCE: 58

His Asp Lys Ile Gly Lys Gly Phe Lys Thr Trp Lys Ile Ser Leu Gln
1               5                   10                  15

Glu Met Ala Gln
            20

<210> SEQ ID NO 59
<211> LENGTH: 292
<212> TYPE: PRT
<213> ORGANISM: Human rhinovirus 89

<400> SEQUENCE: 59

Asn Pro Val Glu Asn Tyr Ile Asp Ser Val Leu Asn Glu Val Leu Val
1               5                   10                  15

Val Pro Asn Ile Gln Pro Ser Thr Ser Val Ser Ser His Ala Ala Pro
            20                  25                  30

Ala Leu Asp Ala Ala Glu Thr Gly His Thr Ser Ser Val Gln Pro Glu
        35                  40                  45

Asp Met Ile Glu Thr Arg Tyr Val Ile Thr Asp Gln Thr Arg Asp Glu
    50                  55                  60

Thr Ser Ile Glu Ser Phe Leu Gly Arg Ser Gly Cys Ile Ala Met Ile
65                  70                  75                  80

Glu Phe Asn Thr Ser Ser Asp Lys Thr Glu His Asp Lys Ile Gly Lys
                85                  90                  95

Gly Phe Lys Thr Trp Lys Ile Ser Leu Gln Glu Met Ala Gln Ile Arg
            100                 105                 110

Arg Lys Tyr Glu Leu Phe Thr Tyr Thr Arg Phe Asp Ser Glu Ile Thr
        115                 120                 125

Ile Val Thr Ala Ala Ala Ala Gln Gly Asp Asp Ser Gly His Ile Val
    130                 135                 140

Leu Gln Phe Met Tyr Val Pro Pro Gly Ala Pro Val Pro Glu Lys Arg
145                 150                 155                 160

Asp Asp Tyr Thr Trp Gln Ser Gly Thr Asn Ala Ser Val Phe Trp Gln
                165                 170                 175

Glu Gly Gln Pro Tyr Pro Arg Phe Thr Ile Pro Phe Met Ser Ile Ala
            180                 185                 190

Ser Ala Tyr Tyr Met Phe Tyr Asp Gly Tyr Asp Gly Asp Ser Ala Ala
        195                 200                 205

Ser Lys Tyr Gly Ser Val Val Thr Asn Asp Met Gly Thr Ile Cys Val
    210                 215                 220

Arg Ile Val Thr Ser Asn Gln Lys His Asp Leu Asn Ile Val Cys Arg
225                 230                 235                 240

Ile Tyr His Lys Ala Lys His Ile Lys Ala Trp Cys Pro Arg Pro Pro
                245                 250                 255

Arg Ala Val Ala Tyr Gln His Thr His Ser Thr Asn Tyr Ile Pro Ser
            260                 265                 270

```
Asn Gly Glu Ala Thr Thr Gln Ile Lys Thr Arg Pro Asp Val Phe Thr
        275                 280                 285

Gly Thr Asn Val
        290
```